US012653586B2

(12) United States Patent　　　　(10) Patent No.:　US 12,653,586 B2

Gray et al.　　　　　　　　　　　　(45) Date of Patent:　　Jun. 16, 2026

(54) LARGE FRAGMENT PLATES AND INSTRUMENTS

(71) Applicant: GLOBUS MEDICAL, INC., Audubon, PA (US)

(72) Inventors: Rebecca Gray, Spring City, PA (US); Jean Bordeaux, West Chester, PA (US); Anna Kedzierska, Conshohocken, PA (US)

(73) Assignee: Globus Medical, Inc., Audubon, PA (US)

( * ) Notice: Subject to any disclaimer, the term of this patent is extended or adjusted under 35 U.S.C. 154(b) by 139 days.

(21) Appl. No.: 18/515,480

(22) Filed: Nov. 21, 2023

(65) Prior Publication Data

US 2025/0160910 A1　　May 22, 2025

(51) Int. Cl.
*A61B 17/80*　　　　(2006.01)
*A61B 17/56*　　　　(2006.01)

(52) U.S. Cl.
CPC .......... *A61B 17/8057* (2013.01); *A61B 17/56* (2013.01); *A61B 17/8061* (2013.01); *A61B 2017/564* (2013.01); *A61B 17/8004* (2013.01); *A61B 17/8014* (2013.01); *A61B 17/8019* (2013.01); *A61B 17/8052* (2013.01); *A61B 17/808* (2013.01)

(58) Field of Classification Search
CPC . A61B 17/8019; A61B 17/56; A61B 17/8014; A61B 17/8057; A61B 17/8061; A61B 17/808; A61B 17/80; A61B 17/8004; A61B 17/8052; A61B 17/68; A61B 17/681; A61B 17/685; A61B 17/58; A61B 17/846; A61B 2017/564

USPC ........ 606/280, 86 B, 902, 915, 86 R, 87, 71, 606/281, 282, 286, 291, 105
See application file for complete search history.

(56) References Cited

U.S. PATENT DOCUMENTS

| | | | |
|---|---|---|---|
| 3,386,437 A | | 6/1968 | Treace |
| 4,102,339 A | * | 7/1978 | Weber ................ A61B 17/8019 |
| | | | 606/105 |
| 6,716,218 B2 | | 4/2004 | Holmes et al. |
| 7,776,076 B2 | | 8/2010 | Grady, Jr. et al. |
| 8,167,891 B2 | | 5/2012 | Terres et al. |
| 8,740,915 B2 | | 6/2014 | Niederberger et al. |
| 8,753,348 B2 | | 6/2014 | DiDomenico et al. |
| 8,936,615 B2 | | 1/2015 | Pappalardo et al. |
| 9,011,507 B2 | | 4/2015 | Schelling |
| 9,023,052 B2 | | 5/2015 | Lietz et al. |
| 9,113,969 B2 | | 8/2015 | Niederberger et al. |
| 9,351,773 B2 | | 5/2016 | DiDomenico et al. |
| 9,402,665 B2 | | 8/2016 | Medoff et al. |

(Continued)

FOREIGN PATENT DOCUMENTS

| | | | |
|---|---|---|---|
| BR | 102014003223 A2 | 12/2015 | |
| CN | 103598912 A | 2/2014 | |

(Continued)

*Primary Examiner* — Marcela I. Shirsat

(57) ABSTRACT

Devices, systems, instruments, and methods for promoting healing and stability for bone fractures. Large fragment plating systems with a variety of plate styles allow for reduction of the fracture to achieve primary bone healing. Compression and/or distraction may be applied to the bone fragments during the procedure with an external instrument, such as a fracture reduction instrument configured to restore the fracture while implanting the plate.

6 Claims, 48 Drawing Sheets

(56)        References Cited

U.S. PATENT DOCUMENTS

| | | |
|---|---|---|
| 9,468,479 B2 | 10/2016 | Marotta et al. |
| 9,597,130 B2 | 3/2017 | Pappalardo et al. |
| 11,083,505 B1 | 8/2021 | Patterson |
| 11,642,156 B2 | 5/2023 | Bennett et al. |
| 2007/0270849 A1 | 11/2007 | Orbay et al. |
| 2009/0182345 A1* | 7/2009 | Medoff .............. A61B 17/8019 |
| | | 606/86 R |
| 2018/0168811 A1 | 6/2018 | Ranganathan et al. |
| 2019/0076174 A1* | 3/2019 | Tiongson ............. A61B 17/846 |
| 2022/0395303 A1 | 12/2022 | Rakes et al. |
| 2023/0142959 A1 | 5/2023 | Zysk et al. |
| 2023/0200871 A1 | 6/2023 | Rakes et al. |

FOREIGN PATENT DOCUMENTS

| | | |
|---|---|---|
| CN | 106037912 A | 10/2016 |
| CN | 113197638 A | 8/2021 |
| CN | 113197640 A | 8/2021 |
| DE | 1880848 | 7/1963 |
| DE | 1962581 | 6/1971 |
| DE | 7315277 U | 8/1973 |
| EP | 0207884 A2 | 1/1987 |
| EP | 3184061 A1 | 6/2017 |
| GB | 1118773 A | 7/1968 |
| KR | 102004365 B1 | 7/2019 |
| WO | 2021262128 A1 | 12/2021 |

* cited by examiner 10
(a)
(b)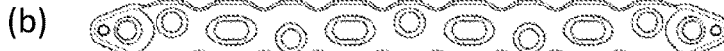
(c)
(d)
(e)
(f)
FIG. 1

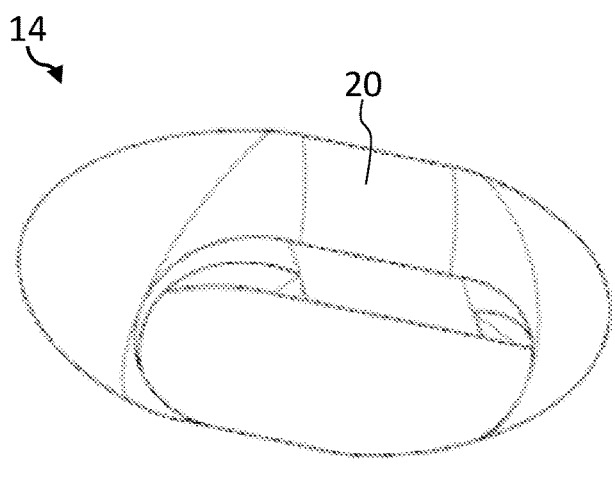
FIG. 2A
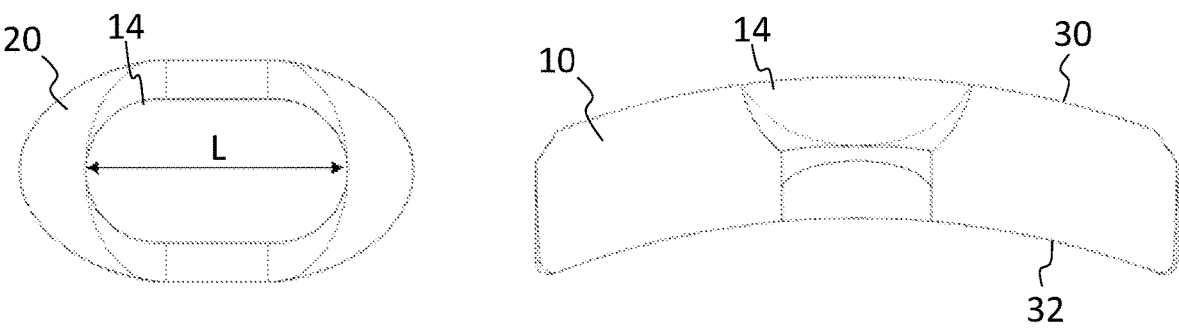
FIG. 2B
FIG. 2C
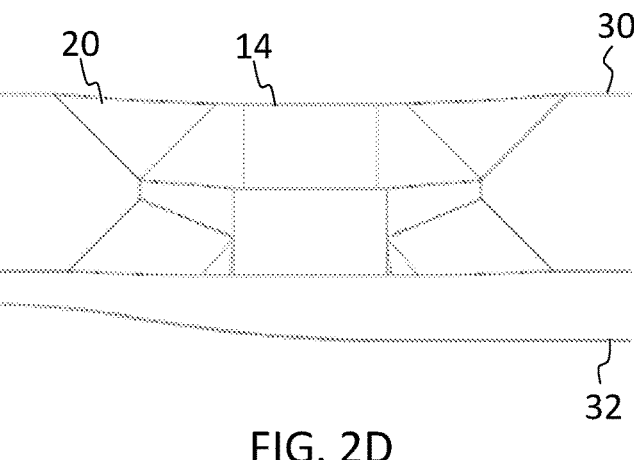
FIG. 2D

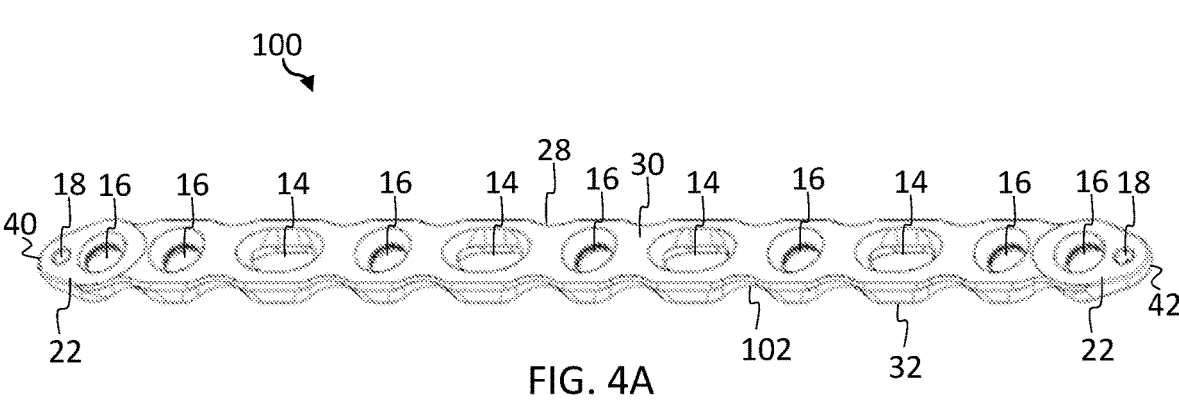
FIG. 4A
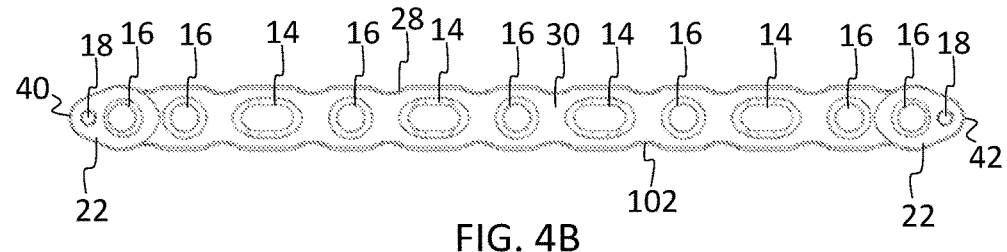
FIG. 4B
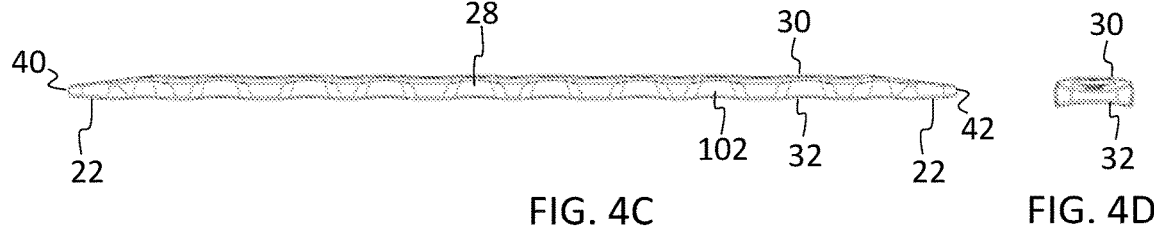
FIG. 4C
FIG. 4D
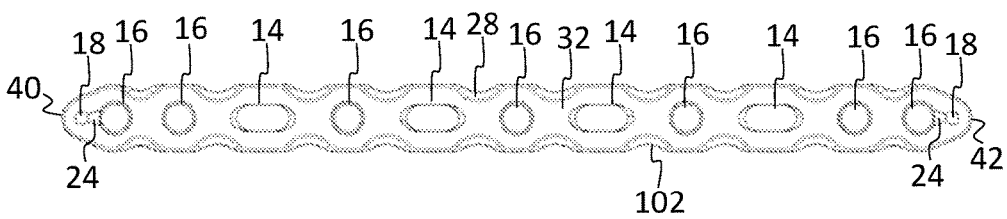
FIG. 4E

200

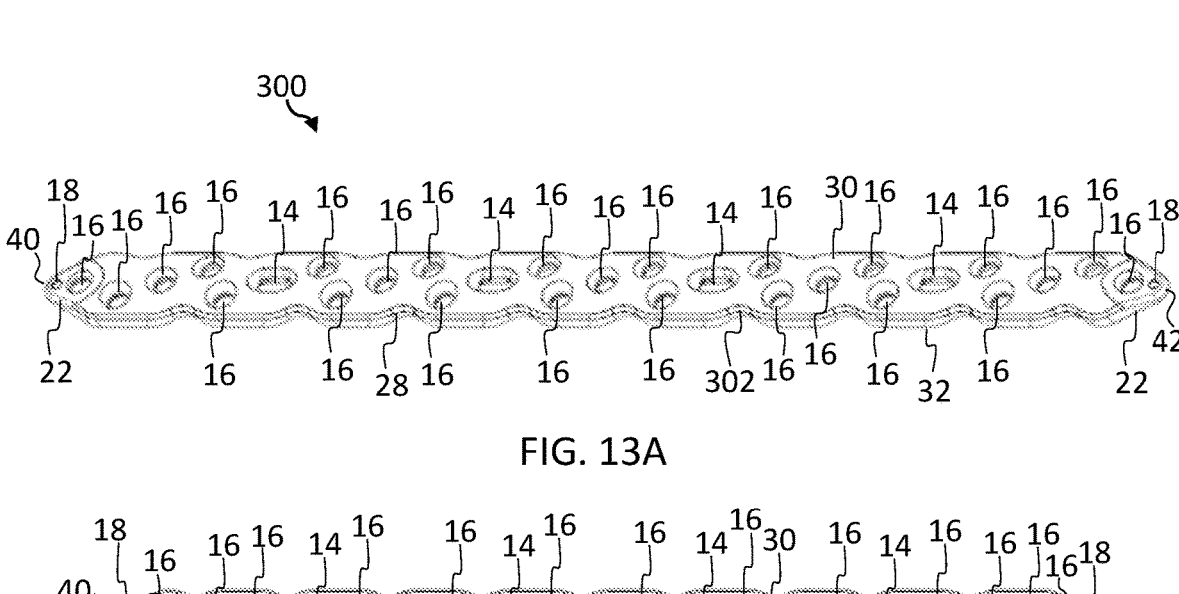
FIG. 13A
FIG. 13B
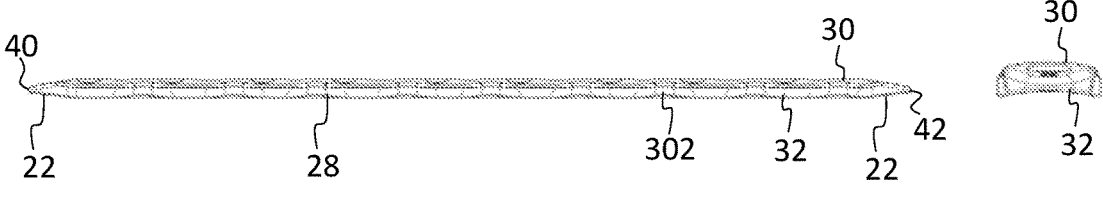
FIG. 13C
FIG. 13D
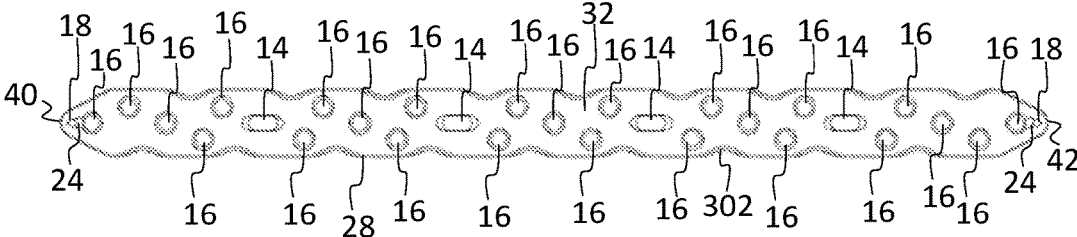
FIG. 13E

300

300

300

400

500

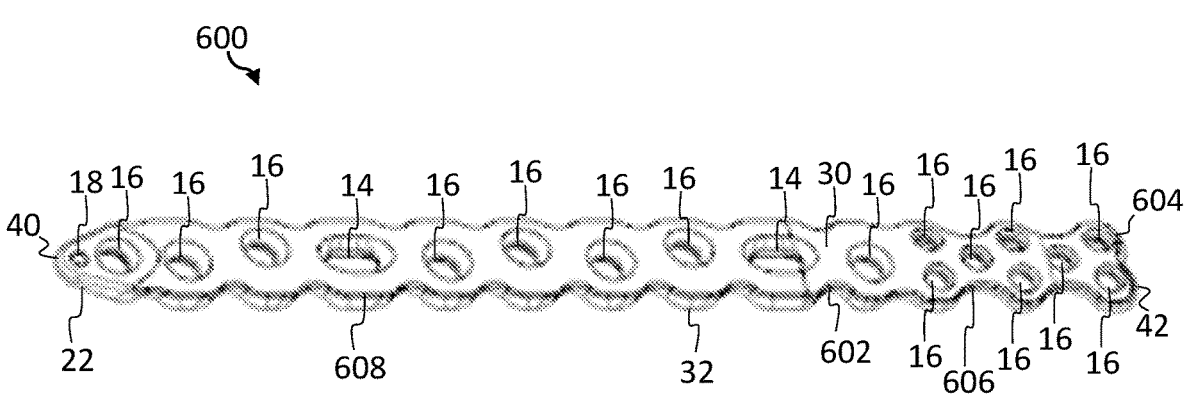
FIG. 25A
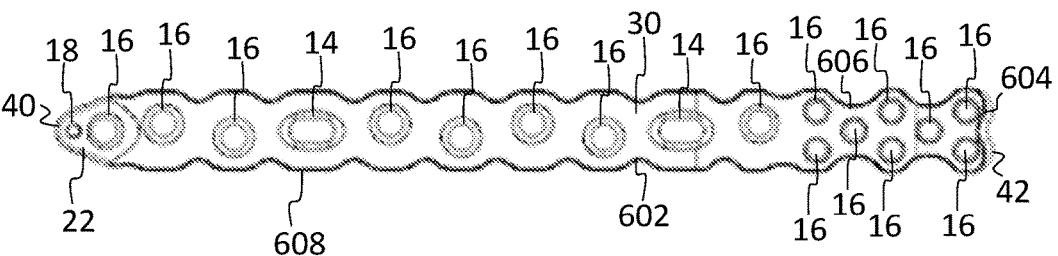
FIG. 25B
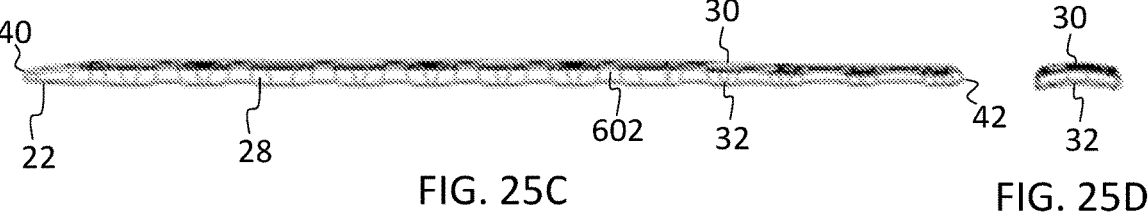
FIG. 25C
FIG. 25D
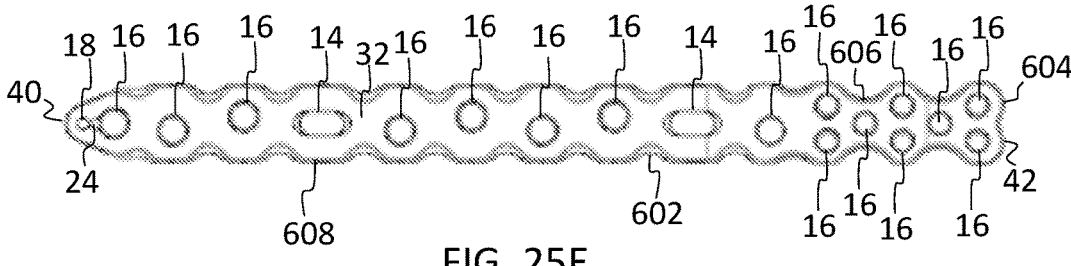
FIG. 25E

600

700

710    744    714

748    746

720

706

722

738    740

730    732

702    704

734    736

716

708    770    772    718

719

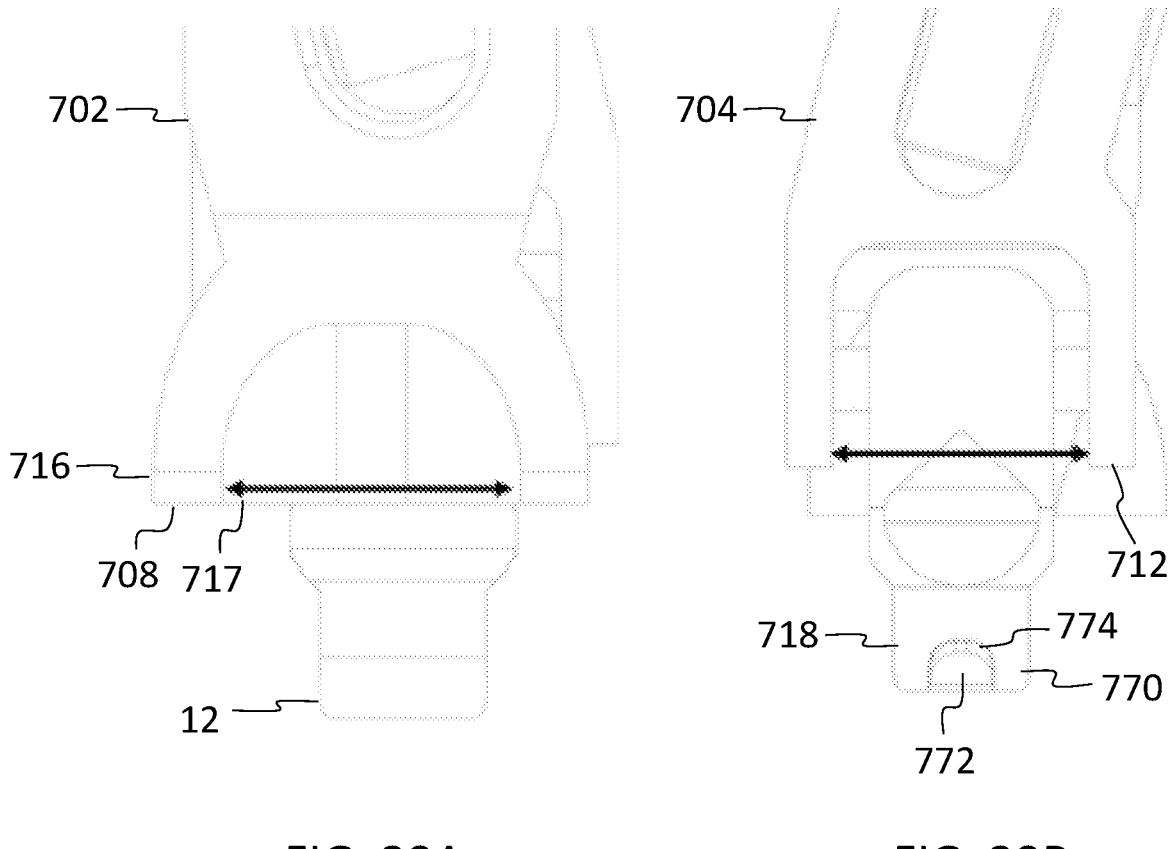
FIG. 29A                              FIG. 29B

LARGE FRAGMENT PLATES AND INSTRUMENTS

FIELD OF THE INVENTION

The present disclosure relates to surgical devices, and more particularly, to stabilization systems, for example, for trauma applications.

BACKGROUND OF THE INVENTION

Bone fractures of long bones may be treated by fixation of the bone to stabilize and align the fractured bone, facilitating the healing process. Large fragment plates may include, for example, non-anatomically contoured plates that are indicated for large, long bones including the femur, humerus, and tibia, as well as anatomically contoured plates that are indicated for the distal femur, periprosthetic femur, and pelvic fractures. Frequently, these plates are used to treat extra-articular fractures. In treating extra-articular transverse, oblique, and spiral fractures, adequate compression of the fracture is needed to achieve primary bone healing. Current compression methods, such as direct reduction with clamps, using a lag screw, and using an articulating tensioning device for simple extra-articular fractures are not ideal. Thus, there remains a need for improved plating systems and compression methods that provide appropriate stabilization to the bone.

SUMMARY OF THE INVENTION

To meet this and other needs, and in view of its purposes, the present application provides devices, systems, instruments, and methods for promoting healing and stability for bone fractures. In particular, large fragment plating systems with a variety of plate styles may be used to treat a wide range of fractures. The plates allow for reduction of the fracture to achieve primary bone healing. Compression and/or distraction may be applied to the bone fragments during the procedure with an external instrument, such as a fracture reduction instrument. The fracture reduction instrument may be configured to restore the fracture while implanting the plate to provide compression and/or distraction of the fracture.

According to one embodiment, a bone stabilization system for reducing a fracture between two bone fragments includes a bone plate and a fracture reduction instrument. The bone plate may have an elongate body extending between two ends. The bone plate has a shaft portion and a tapered region decreasing in thickness from the shaft to one end. A plurality of fastener openings are defined therethrough including one polyaxial opening extending through the tapered region, and polyaxial openings and compression slots extending through the shaft portion. The fracture reduction instrument has a translation arm and a hook arm pivotably coupled together. The translation arm has a screw engaging projection configured to engage a bone screw and the hook arm has a hook configured to engage the bone plate. The fracture reduction instrument is configured to apply compression or distraction by translation of the bone plate to reduce or distract the fracture.

The bone stabilization system may include one or more of the following features. The bone plates may include large fragment bone plates, such as narrow straight plates, standard straight plates, broad straight plates, standard curved plates, broad curved plates, and metaphyseal straight plates. When the bone screw is positioned through the compression slot and the screw engaging projection of the instrument applies a force to the bone screw towards the fracture site, compression is applied to the fracture. When the bone screw is positioned outside of the bone plate and the screw engaging projection of the instrument applies a force to the bone screw, distraction is applied to the fracture. A guide wire hole may be defined through the tapered region, and a swept cut may connect the polyaxial opening to the guide wire hole on an underside of the bone plate. The fastener openings defined through the shaft portion may form a mirrored repeating pattern about a central transverse plane of the bone plate. The fastener openings defined through the shaft portion may form a repeating three-hole pattern arranged on a slope. The compression slots may be aligned along a central longitudinal axis, and the polyaxial openings may be aligned along first and second offset axes located above and below the central longitudinal axis, respectively. The bone plate may include a metaphyseal portion having a thin plate thickness, a diaphyseal portion having a thick plate thickness, and a transition region between the metaphyseal portion and the diaphyseal portion. The metaphyseal portion and the transition region may have polyaxial openings with a diameter smaller than the polyaxial openings in the diaphyseal portion.

According to one embodiment, a fracture reduction instrument for reducing a bone fracture includes first and second pivoting arms extending from a proximal end to a distal end. The first and second pivoting arms have handles near the proximal ends. The first pivoting arm has a screw engaging projection and the second pivoting arm has a plate engaging hook at the respective distal ends. A locking member is positioned between the proximal ends of the first and second pivoting arms. The locking member includes a shaft with a buttress thread positionable through a pivoting locking assembly having a locking ring retained to a central ring and first and second female thread pieces pivotably coupled to the central ring and having teeth engageable with the buttress thread. When the handles are squeezed together, the pivoting locking assembly translates along the shaft in a forward motion and prevents any backward translation, thereby locking the relative position of the first and second pivoting arms.

The fracture reduction instrument may include one or more of the following features. The screw engaging projection may include a U-shaped slot configured to engage a bone screw, and the U-shaped slot may have a width greater than a diameter of the bone screw to permit translation of the bone screw along the width of the slot. The plate engaging hook may include a hook having an L-shaped body attached to the second pivoting arm with a pair of cross pins, and the hook may be permitted to translate along the cross pins. The pivoting locking assembly may be attached to the second pivoting arm with a pin to ensure a central axis of the locking ring is coincident to a central axis of the buttress thread. The locking ring may be retained to the central ring with pins allowing for translation of the locking ring relative to the central ring. The first and second female thread pieces may have an L-shaped body including an outer base and an inwardly projecting arm defining the teeth configured to engage the buttress thread. The locking ring may be a cylindrical ring defining a reduced inner diameter section, a stepped section, a ramped edge section, and an enlarged inner diameter section. In a resting engaged position, the locking ring and central ring may be overlapping, causing the first and second female thread pieces to sit in the reduced inner diameter section of the locking ring with the teeth engaging the buttress thread. In a translated position when the handles are squeezed, the locking ring may translate outward and away from the central ring, and the first and second female thread pieces may withdraw from the reduced inner diameter section and enter the enlarged inner diameter section of the locking ring with the teeth engaging the buttress thread. In a disengaged position when the handles are squeezed further, the first and second female thread pieces may disengage from the buttress thread and act as a ratcheting mechanism to translate along the length of the shaft.

According to one embodiment, a method for reducing a fracture may include one or more of the following steps in any suitable order, including: providing a fracture reduction instrument configured to temporarily attach to a bone plate and temporarily engage a bone screw to apply compression and/or distraction to the fracture; and either: (a) compressing the fracture or (b) distracting the fracture.

Compressing the fracture (a) may include: (a1) positioning the bone plate against an exterior surface of a long bone and across a fracture; (a2) securing the bone plate to a bone fragment on one end of the fracture by attaching a first fastener through a polyaxial opening in the bone plate; (a3) hooking the fracture reduction instrument under a screw hole on the opposite side of the fracture; (a4) inserting a second fastener into a compression slot nearest to the instrument at a location that is closer to the fracture site than the hook; (a5) manipulating the instrument to translate the un-fixed side of the bone plate; (a6) fixing the compression generated through the instrument by inserting a third fastener into any of the hole on the same side of the fracture as the instrument; (a7) removing the instrument; (a8) optionally removing the second fastener in the compression slot or fully seating the second fastener into bone.

Distracting the fracture (b) may include: (b1) positioning the bone plate against an exterior surface of a long bone and across a fracture; (b2) securing the bone plate to a bone fragment on one end of the fracture by attaching a first fastener through a polyaxial opening in the bone plate; (b3) hooking the fracture reduction instrument under a screw hole on the far end of the bone plate on the opposite side of the fracture; (b4) inserting a second fastener into the bone outside of the plate; (b5) manipulating the instrument to translate the bone, thereby distracting the fracture; (b6) fixing the distraction generated by inserting a third fastener into any of the holes on the same side of the fracture as the instrument; (b7) removing the instrument; and (b8) optionally removing the second fastener, fully seating the second fastener into the bone, or replacing the second fastener with a shorter screw. The amount of compression or distraction may be advanced continuously and locked by a pivoting locking assembly on the fracture reduction instrument. The fracture reduction instrument may provide for increased visibility of the incision site and bone plate by including an offset angle between arms of the instrument and the plate.

Also provided are kits for the stabilization systems including bone plates of varying sizes and orientations, fasteners including locking fasteners, non-locking, compression fasteners, polyaxial fasteners, fixed angle fasteners, or any other suitable fasteners, fracture reduction instruments, drill guides, k-wires, sutures, and other instruments and components for installing the same.

BRIEF DESCRIPTION OF THE DRAWINGS

A more complete understanding of the present invention, and the attendant advantages and features thereof, will be more readily understood by reference to the following detailed description when considered in conjunction with the accompanying drawings, wherein:

FIG. 1 shows a collection of large fragment plate styles configured for fixation of fractures and fragments of the long bones;

FIGS. 2A-2D show a perspective view, top view, left view cross section, and front view cross section, respectively, of a dynamic compression slot according to one embodiment;

FIGS. 4A-4E show a perspective view, top view, front view, right view, and bottom view, respectively, of a narrow straight plate according to one embodiment;

FIGS. 13A-13E show a perspective view, top view, front view, right view, and bottom view, respectively, of a broad straight plate according to one embodiment;

FIGS. 25A-25E show a perspective view, top view, front view, right view, and bottom view, respectively, of a metaphyseal plate according to one embodiment;

FIGS. 29A-29B show embodiments of the distal tips of the translation arm and hook arm, thereby providing offset to the screw and hook, respectively;

DETAILED DESCRIPTION OF THE INVENTION

Figures 3A, 3B:
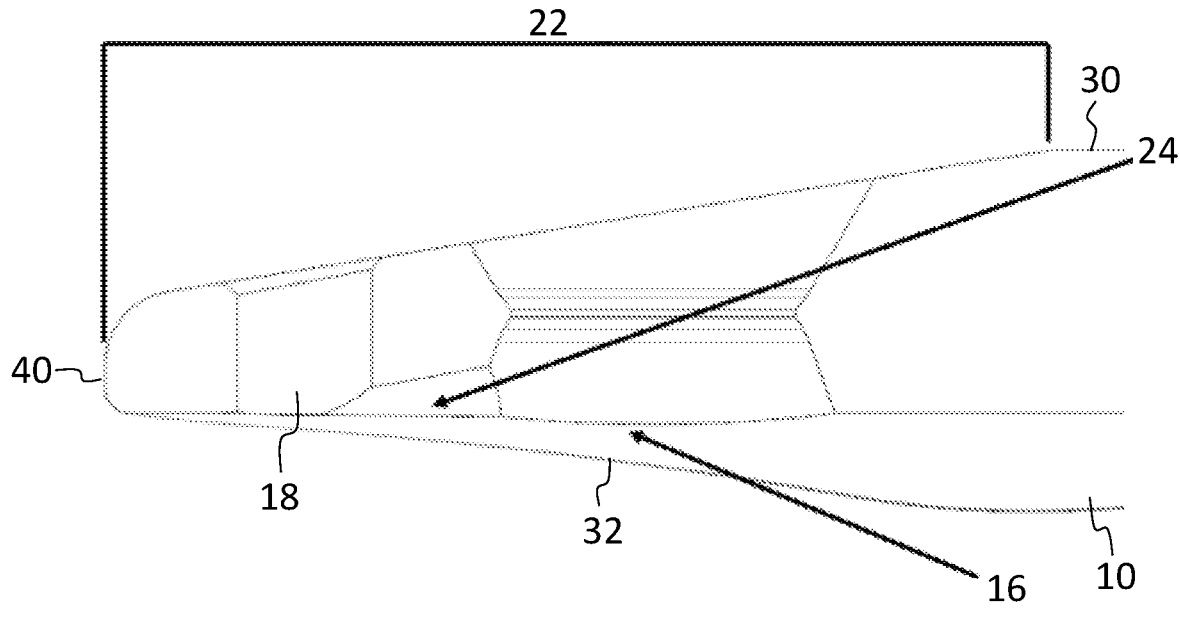
FIGS. 3A-3B show cross section and bottom perspective views, respectively, of the tapered end of the diaphyseal section of large fragment plates according to one embodiment.

Embodiments of the disclosure are generally directed to devices, systems, instruments, and methods for promoting healing and stability for bone fractures. The plates may include a comprehensive offering of plate styles for the stabilization of bone fractures, such as extra-articular fractures. The bone plates may be used to create a very rigid construct with permanent fixation to promote primary healing and stability.

A series of trauma plates may be used for the fixation of fractures and fragments in large, long bones, such as the femur, humerus, and tibia. The plates may be used in the fixation of extra-articular fractures, peri-prosthetic fractures, osteopenic bone, and fixation of nonunions and malunions in adult patients, for example. The fracture plates may be used to address fractures, such as extra-articular transverse, oblique, and spiral fractures, to ensure proper alignment and facilitating healing. The plates may be configured to interface with an external fracture reduction instrument to apply compression and/or distraction, thereby pressing the bone fragments together and reducing the fracture. The plates may provide absolute fracture stability and prevent interfragmentary motion. Although the collection of plates is generally described with reference to stabilizing long bones, it will be appreciated that the stabilization systems described herein may be used or adapted to be used for the fixation of other areas or other bones as well including the spine, pelvis, clavicle, fibula, ulna, radius, bones of the hand, bone of the foot, or other suitable bone(s) or joint(s). The systems may be adapted to secure small or large bone fragments, single or multiple bone fragments, or otherwise secure one or more fractures or joints.

Referring now to FIG. 1, a large fragment plating portfolio 10 is shown according to one embodiment. Six different plate styles may be used in the treatment of various fractures including: (a) narrow straight plate; (b) standard straight plate; (c) broad straight plate; (d) standard curved plate; (e) broad curved plate; and (f) metaphyseal straight plate. Each of the straight plates have no curve when viewed in the top plane because these plates are configured to be implanted on straight bones including the humerus and tibia. The user may bend the plate as needed for their application. The curved plates may have a constant radius of curvature, for example, to match the majority of femora curves in the lateral plane. The curved plates may have any suitable radius of curvature for its intended application.

Each bone plate 10 is configured to be positioned against an outside face of a bone, for example, of a long bone, such as the femur, humerus, and tibia. The bone plate 10 spans the bone fracture(s) to hold the bone fragments together, allowing the bone to heal in the correct alignment. These plates 10 may be provided in a number of variations in a surgical tray, which include for example various types, sizes, and configurations. The tray selection may allow for the surgeon to select a desired plate during surgery after opening the wound area and considering the plating needs for the patient. The bone plates 10 may be available in a variety of lengths, widths, and styles based on the anatomy of the patient and types of fractures.

The bone plates 10 have an elongate body extending from a first end 40 to a second end 42 along a central longitudinal axis A1. The first end 40 may be configured to be the diaphyseal end of the plate 10 and the second end 42 may be configured to be the epiphyseal end of the plate 10. The ends 40, 42 may be each disposed on a diaphyseal portion of the bone. Ends 40, 42 may be situated such that one end is at a diaphyseal portion and one end is at a epiphyseal portion. Although it will be understood that the ends may be reversed or oriented along the bone in any suitable manner. The plate 10 includes a top surface 30 and an opposite, bottom surface 32 configured to contact adjacent bone. The top and bottom surfaces 30, 32 are connected by opposite side surfaces extending from the first to second ends 40, 42 of the plate 10. The bone plates 10 may have a shaft portion 28 with beveled or tapered regions 22 on one or both ends of the shaft 28. Although the plates 10 are shown having a generally longitudinal body, it will be appreciated that any suitable shape and contouring of the plate 10 may be provided depending on the location and type of fracture to be plated.

The elongate body defines one or more through openings 14, 16 each configured to receive a bone fastener 12 therethrough. The fastener openings 14, 16 extend through the body of the plate 10 from a top surface 30 to a bottom surface 32. The fastener openings 14, 16 may include cylindrical openings, conical openings, elongated openings, threaded openings, textured openings, non-threaded and/or non-textured openings, and the like. The openings 14, 16 may allow for locking of the fastener 12 to the plate 10 or may allow for movement and dynamic compression of the bone.

The openings 14, 16 extending through the plates 10 are configured to accept locking fasteners, non-locking fasteners, or a combination of both locking and non-locking fasteners that are able to dynamically compress the bone and/or affix the plate 10 to the bone. For example, a first opening type may include an elongated opening or dynamic compression slot 14, which allows for insertion of non-locking screws 12 into the bone and/or compression along the bone. A second opening type may include a polyaxial locking hole 16 with a textured or threaded portion configured to engage a head portion of the locking fastener 12. The locking screw 12 may include threads or a textured area configured to deform and/or engage with the locking hole 16, thereby locking the fastener 12 to the plate 10. A third opening type may include a K-wire or guide wire hole 18, which is configured to receive a guide wire of K-wire therethrough. Additional details on these and other types of openings are provided in further detail in U.S. Pat. No. 11,432,857, which is incorporated by reference herein in its entirety for all purposes. The plates 10 may comprise any suitable number of openings 14, 16, 18 in any suitable configuration. These openings 14, 16, 18 allow surgeons flexibility for fastener placement, based on preference, anatomy, and fracture location.

With further emphasis on FIGS. 2A-2D, a dynamic compression slot 14 is shown in more detail. The dynamic compression slot 14 allows motion of the plate 10 relative to the bone 2. For example, a fracture may separate bone into two or more bone fragments. In order to move the bone fragments toward one another and minimize the fracture, plate 10 may be secured to bone 2 using a non-locking fastener, for example. When a force is applied, the plate 10 is able to move, resulting in compression of the bone fracture. The dynamic compression slot 14 may be elongated with a ramp 20 milled into the top surface 30 of the plate 10. The ramp 20 may span along the entire upper perimeter of the elongated slot 14. An upper portion of the hole 14 may be tapered, for example, to form the ramp 20 or a portion thereof, a lower portion of hole 14 may further be tapered, and at the intersection between the upper tapered portion and the lower tapered portion a narrowed central portion may be configured to receive the head portion of the non-locking fastener. The compression slots 14 allow for non-locking screws 12 to translate within the length L of the slot 14. For example, the length L of the slot 14 may be 10.2 mm to allow for up to 5.7 mm of compression or distraction of the fracture. The length L and position of the compression slots 14 along the length of the plate 10 may vary with the style and length of the plate 10.

As shown in FIGS. 3A-3B, the large fragment plates 10 may have a shaft portion 28 with beveled or tapered regions 22 on one or both ends of the plate 10. For example, the tapered region 22 may decrease in thickness from the shaft 28 toward the diaphyseal end 40 of the plate 10. The tapered region 22 may also decrease in width from the shaft 28 toward the end 40, 42, thereby forming a pointed nose or tip. A polyaxial hole 16 extends through the tapered region 22. A wire hole 18 may also extend through the tapered region 22 between the polyaxial hole 16 and the end 40 of the plate 10. The polyaxial hole 16 on the diaphyseal tapered end 22 may be able to accept locking screws (e.g., a 4.5 mm locking screw), non-locking screws (e.g., a 4.5 mm non-locking screw), cancellous screws (e.g., a 5.5 mm cancellous screw), an articulated tension device (ATD), or other instruments. As best seen in FIG. 3B, an underside of the polyaxial hole 16 through the tapered end 22 may define a recess or swept cut 24. A hook of an articulating tensioning device (not shown) or other instrument may be received in the hole 16 due to the swept cut 24 on the underside of the hole 16. The swept cut 24 may be a cavity in the bottom surface 32 of the plate 10 between the polyaxial hole 16 and the guide wire hole 18. The swept cut 24 may be angled or sloping downward toward the guide wire hole 18.

With regard to the guide wire or K-wire holes 18, all plates may include a K-wire hole 18 on the plate end(s) that have the polyaxial hole 16. The narrow straight plate (a), standard straight plate (b), broad straight plate (c), standard curved plate (d), and broad curved plate (e) may each include two K-wire holes 18, one on either end 40, 42 of the plate 10. The metaphyseal straight plate (f) may have only one K-wire hole 18 on the diaphyseal end 40 of the plate 10. The K-wire holes 18 have a diameter smaller than the diameter of the polyaxial holes 16 and are sized and dimensioned to receive a K-wire or other guide wire (e.g., 2.7 mm K-wire hole).

The plate 10 may be configured to receive bone fasteners 12. The fasteners 12 may include locking fasteners, non-locking fasteners, or any other fasteners known in the art. The fasteners 12 may comprise bone screws or the like. The fasteners 12 may be cannulated such that they may be guided into place over guide wires. The fasteners 12 may also include other fasteners or anchors configured to be secured or engaged with bone, such as nails, spikes, staples, pegs, barbs, hooks, or the like. In some embodiments, the fasteners 12 may include fixed and/or variable angle bone screws. The fastener 12 may include a head portion and a threaded shaft portion configured to engage bone. In the case of a locking fastener 12, the head portion may include a textured area, such as threads, around its outer surface sized and configured to engage with the polyaxial opening 16, for example, with corresponding threads in the opening 16 in order to lock the fastener 12 to the plate 10. In the alternative, for a non-locking fastener 12, the head portion may be substantially smooth and rounded to allow for dynamic compression of the bone 2. The fasteners 12 may have a threaded shaft portion configured to engage bone and secure the fastener 12 to bone.

The bone plates 10 may be available in a variety of lengths, widths, and styles based on the anatomy of the patient. The plates 10 may be configured in both left and right designs, in a mirrored configuration, in order to address the anatomy of both the left and right sides of the patient. In particular, the systems may include a series of trauma plates 10 and screws 12 designed for the fixation of fractures and fragments in diaphyseal, metaphyseal, and epiphyseal bone. Different systems may be used to treat various types and locations of fractures.

The bone plate 10 may be comprised of titanium, stainless steel, cobalt chrome, carbon composite, plastic or polymer-such as polyetheretherketone (PEEK), polyethylene, ultra high molecular weight polyethylene (UHMWPE), resorb-able polylactic acid (PLA), polyglycolic acid (PGA), com-binations or alloys of such materials or any other appropriate material that has sufficient strength to be secured to and hold bone, while also having sufficient biocompatibility to be implanted into a body. Similarly, the fasteners 12 may be comprised of titanium, cobalt chrome, cobalt-chrome-mo-lybdenum, stainless steel, tungsten carbide, combinations or alloys of such materials or other appropriate biocompatible materials. Although the above list of materials includes many typical materials out of which bone plates and bone fasteners are made, it should be understood that the bone plates and fasteners comprised of any appropriate material are contemplated.

Turning now to FIGS. 4A-7B, several embodiments of narrow straight plates 100 are shown in more detail. The narrow straight plates 100 are straight and slender in profile for the fixation of various straight bones, such as the humerus and tibia. The straight plates 100 have no curve when viewed in the top plane but may be contoured by the surgeon if desired.

As best seen in FIGS. 4A-4E, the narrow straight plates 100 may have a wavy profile with scalloped edges 102 configured to preserve the periosteum and offer a more consistent strength across the length of the plate 10. As best seen in FIG. 4E, the scalloped edges 102 may also cut into the bottom side 32 of the plate 10 to form relief cuts. Narrowed portions of the scalloped edges 102 may coincide with locations between the compression slots 14 and polyaxial holes 16. In this manner, the outer edges of the plate 100 may be scalloped or wavy to follow the hole pattern, minimizing potential soft tissue irritation. The scal-loped areas 102 may act to limit contact between the plate 100 and the bone to preserve the anatomy.

Figure 5A:
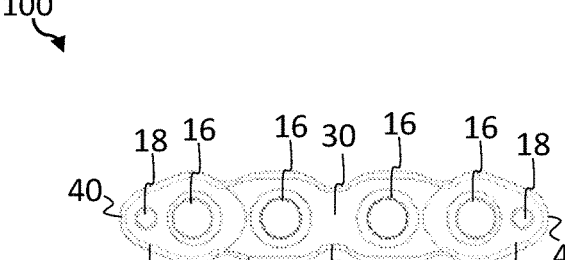
FIGS. 5A-5C show 4-hole, 7-hole, and 11-hole versions, respectively, of the narrow straight plates.
Figure 5B:
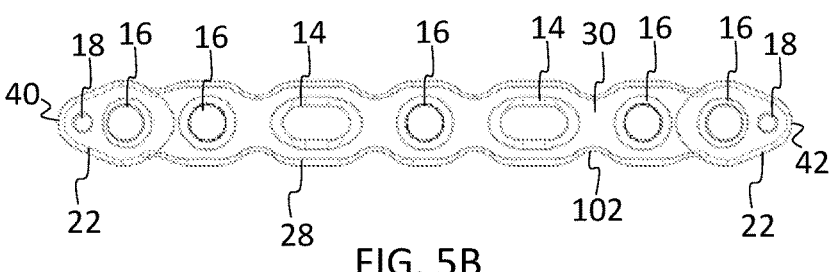
Figure 5C:
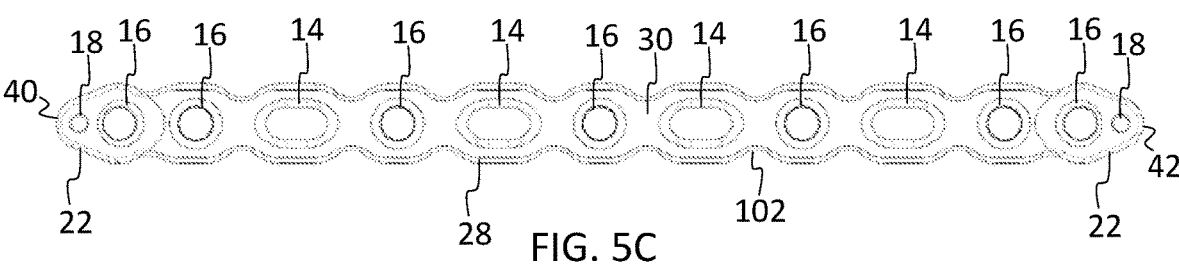

As shown in FIG. 5A-5C, the number of compression slots 14 and polyaxial holes 16 may vary as well as the length of the plate 100. The narrow straight plate 100 may have no compression slots 14 (as shown in FIG. 5A), two compression slots 14 (as shown in FIG. 5B), or four com-pression slots 14 (as shown in FIG. 5C) depending on the plate length. As shown in FIG. 5A, narrow straight plates 100 with less than six fastener holes may only have polyaxial holes 16 (e.g., 4.5 mm polyaxial holes). As shown in FIG. 5B, narrow straight plates 100 with six to ten fastener holes may have two compression slots 14 while the remaining holes are polyaxial holes 16. As shown in FIG. 5C, narrow straight plates 100 with greater than ten fastener holes may have four compression slots 14 while the remain-ing holes are polyaxial holes 16.

Figure 6A:
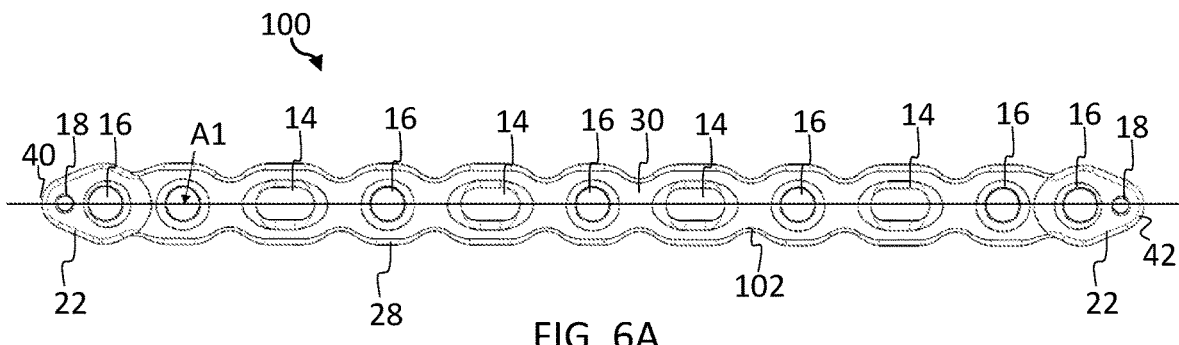
FIGS. 6A-6C show positions of the polyaxial locking holes and compressions slots for various straight plates.
Figure 6B:
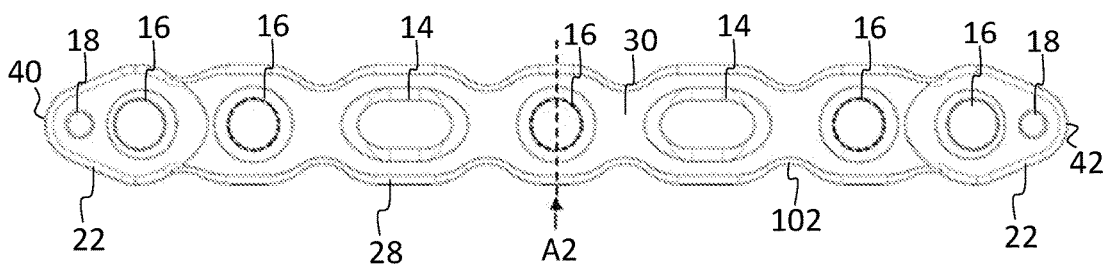
Figure 6C:
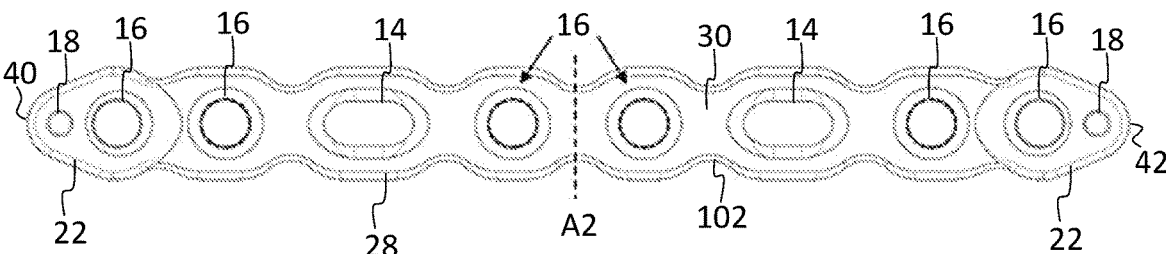

With further emphasis on FIGS. 6A-6C, the holes 14, 16 may form a repeating pattern or mirrored pattern about a center axis or transverse plane A2. As shown in FIG. 6A, all holes 14, 16, 18 in the narrow straight plate 100 may be coincident with the long axis A1 of the plate 100. Narrow straight plates 100 with at least six fastener holes 14, 16 may have two compression slots 14 positioned one or two holes offset from the transverse plane A2 of the plate 100, depend-ing if there is an even or odd number of holes 14, 16. As best seen in FIG. 6B, an odd number of fastener holes 14, 16 (e.g., seven holes) result in a middle polyaxial locking hole 16. The middle polyaxial hole 16 is centered on the trans-verse plane A2 and compression slots 14 are located on either side of the middle locking hole 16. As best seen in FIG. 6C, an even number of fastener holes 14, 16 (e.g., eight holes) results in two middle locking holes 16. The two middle holes 16 are mirrored over the transverse plane A2 and compression slots 14 are positioned on opposite sides adjacent to those two middle locking holes 16. In each case, the compression slots 14 may be symmetric about the transverse plane A2 of the plate 100.

Figures 7A, 7B:
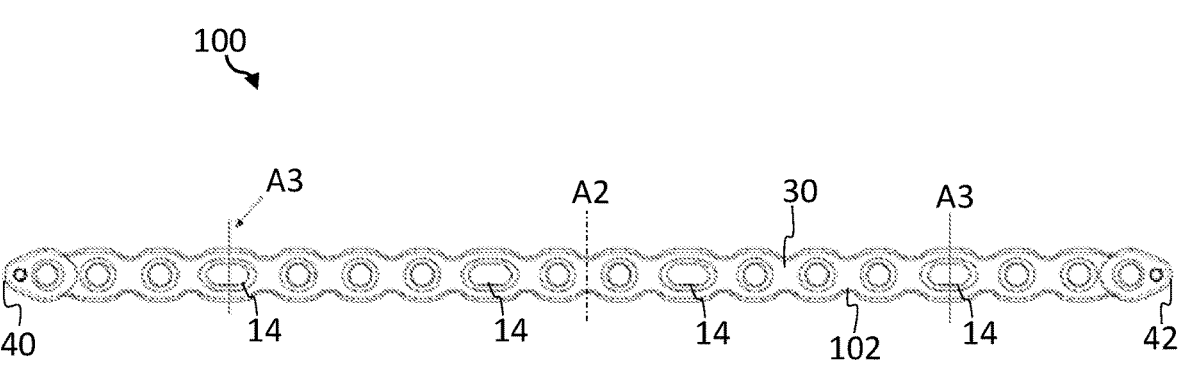
FIGS. 7A-7B show locations for additional compression slots for some longer narrow straight plates.
Figures 8A, 8B, 8C, 8D, 8E:
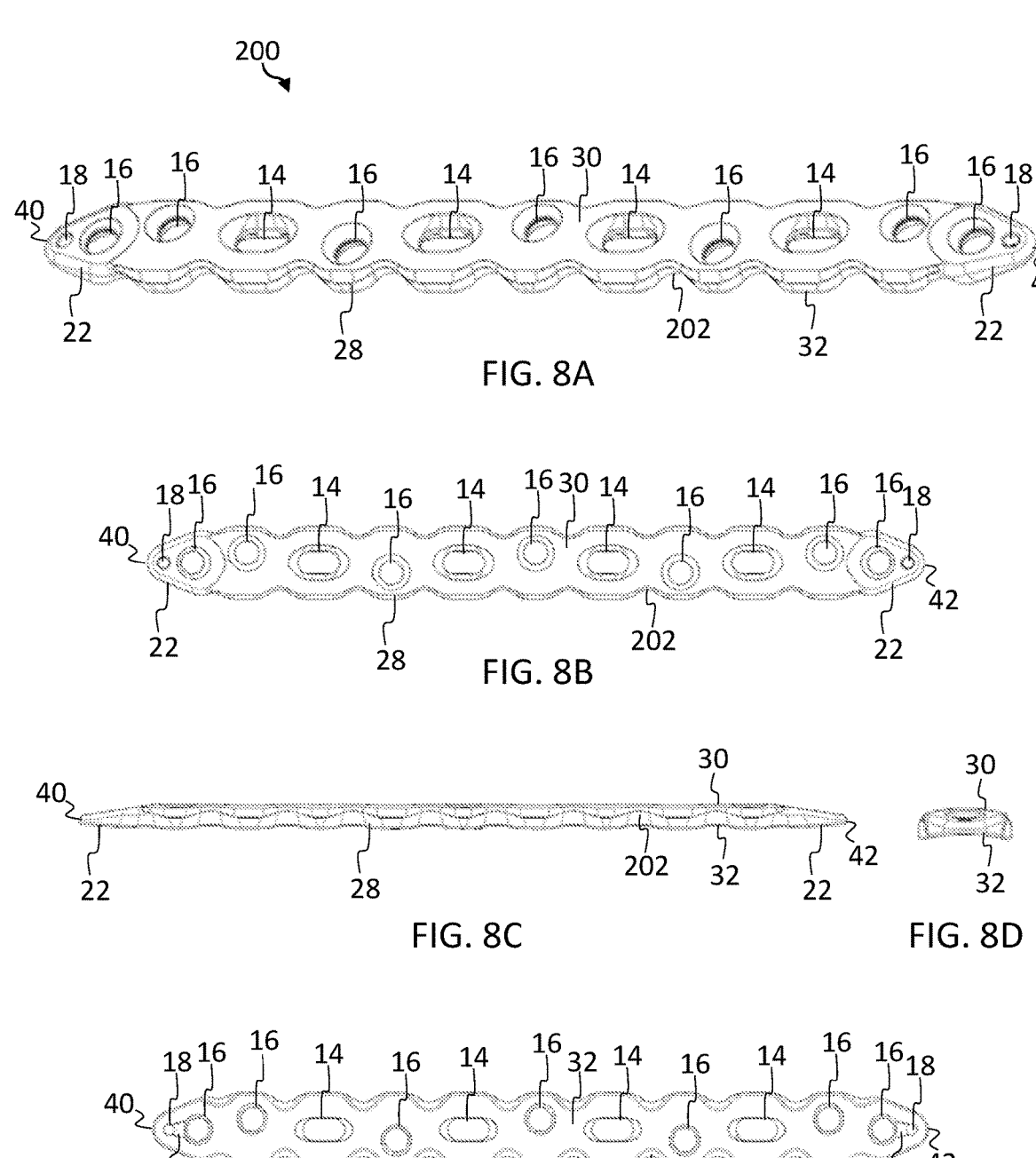
FIGS. 8A-8E show a perspective view, top view, front view, right view, and bottom view, respectively, of a standard straight plate according to one embodiment.

With further emphasis on FIGS. 7A-7B, narrow straight plates 100 between ten and eighteen fastener holes 14, 16 may have an additional two compression slots 14. As shown in FIG. 7A, additional compression slots 14 may be posi-tioned at a location halfway A3 between the central com-pression slots 14 and the ends 40, 42 of the plate 100. The compression slot 14 may be positioned nearest to the half-way point A3 between the middle compression slot 14 and the end 40, 42 of the plate 100, closest to the transverse plane A2 of the plate 100. The two sides of plate 100 about transverse plane A2 may be mirror images of one another. Narrow straight plates 100 with greater than eighteen fas-tener holes may also have an additional two compression slots 14. As shown in FIG. 7B, these additional slots 14 may be positioned four fastener holes 14, 16 from each end 40, 42 of the plate 100.

Turning now to FIGS. 8A-12C, several embodiments of standard straight plates 200 are shown in more detail. The standard straight plates 200 are similar to the narrow straight plates 100 with a broader profile where some fastener holes 14, 16 are offset from the center axis A1. The standard straight plates 200 are suitable for the fixation of various straight bones, such as the humerus and tibia. The straight plates 200 have no curve when viewed in the top plane but may be contoured by the surgeon if desired.

As shown in FIGS. 8A-8E, the standard straight plates 200 include scalloped edges 202 consistent with the narrow straight plates 100 to preserve the periosteum and offer a more consistent strength across the length of the plate 200. The spacing between scallops 202 surrounding dynamic compression slots 14 may be greater than the spacing between scallops 202 surrounding locking holes 16 due to the added length L in the large fragment dynamic compres-sion slots 14.

Figure 9A:
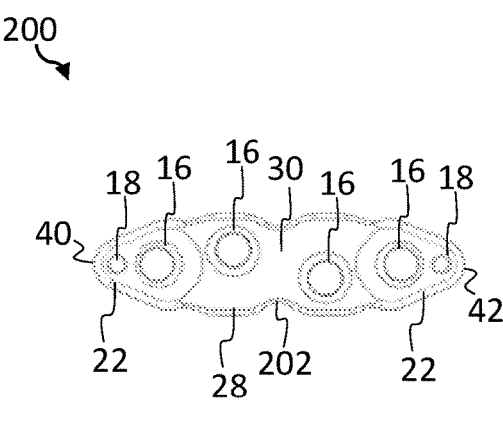
FIGS. 9A-9C show 4-hole, 7-hole, and 11-hole versions, respectively, of the standard straight plates.
Figure 9B:
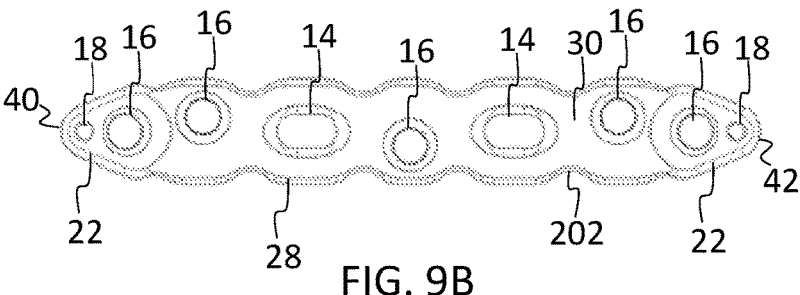
Figure 9C:
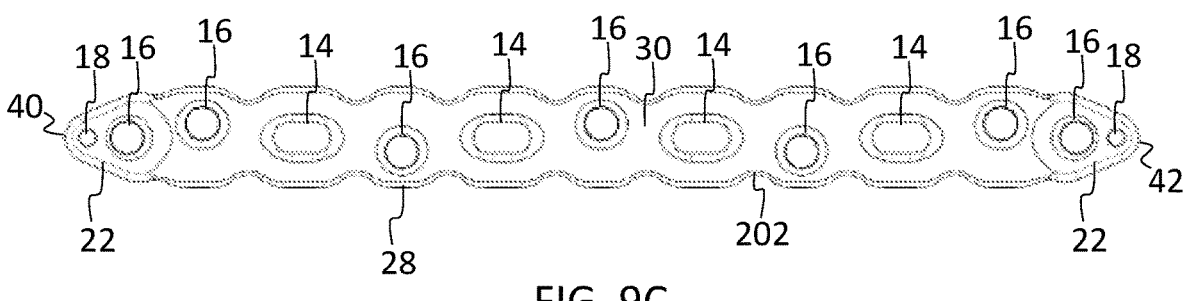

FIGS. 9A-9C show versions of the 4-hole, 7-hole, and 11-hole standard straight plates 200. The standard straight plates 200 may have no compression slots 14, two compres-sion slots 14, or four compression slots 14 depending on the plate length. As shown in FIG. 9A, standard straight plates 200 with less than six fastener holes may have only polyaxial holes 16 (e.g., 4.5 mm polyaxial holes). As shown in FIG. 9B, standard straight plates 200 with six to ten fastener holes may have two compression slots 14 while the remaining holes are polyaxial holes 16. As shown in FIG. 9C, standard straight plates 200 with greater than ten fas-tener holes may have four compression slots 14 while the remaining holes are polyaxial holes 16.

Figure 10A:
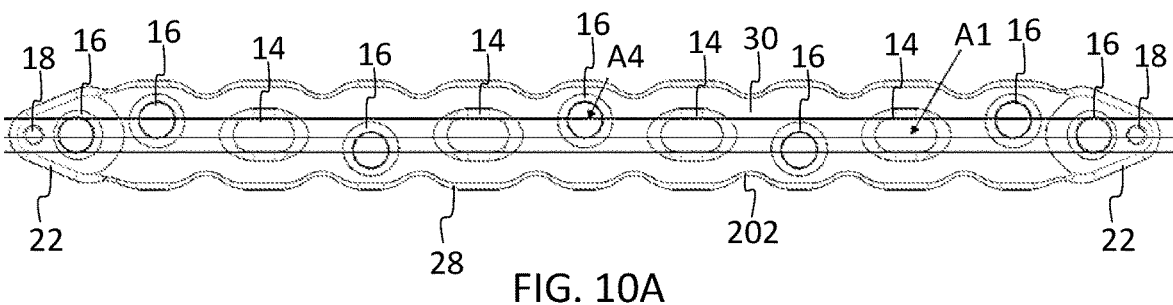
FIGS. 10A-10B show locations for polyaxial holes and compression slots for various standard straight plates.
Figure 10B:
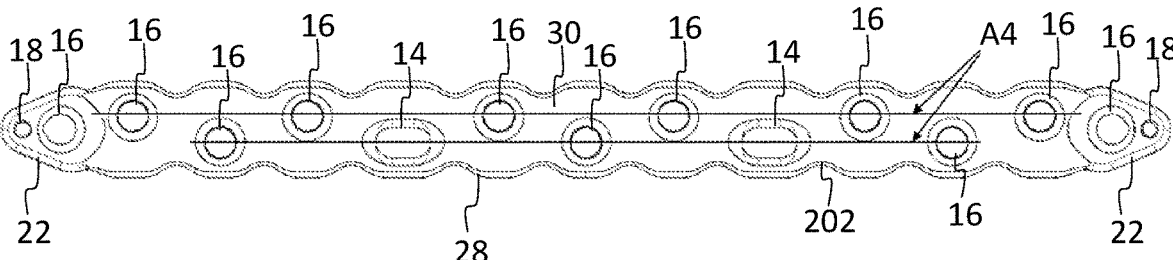

FIGS. 10A-10B show positions of shaft holes 14, 16 in some standard straight plates 200. The shaft 28 of the standard straight plates 200 may have polyaxial locking holes 16 that are all offset from the central axis A1 of the plate 200. An offset axis A4 may be aligned parallel to axis A1 but offset above or below A1. As shown in FIG. 10A, some of the polyaxial openings 16 (e.g., three upper polyaxial holes) are aligned with a first offset axis A4 and some of the polyaxial openings 16 (e.g., two lower polyaxial holes) are aligned with a second offset axis A4. The compression slots 14 (e.g., four compression slots) may be provided coincident with the central axis A1 of the plate 200. The polyaxial holes 16 and K-wire holes 18 in the beveled or tapered ends 22 are aligned with the central axis A1. Alternatively, as shown in FIG. 10B, all shaft holes 14, 16 may be offset from the central axis A1 of the plate 200. Polyaxial holes 16 (e.g., six upper polyaxial holes) are aligned with the first offset axis A4 and compression slots 14 and polyaxial holes 16 (e.g., two lower compression slots and three lower polyaxial holes) are aligned with second offset axis A4. The polyaxial holes 16 and K-wire holes 18 in the beveled or tapered ends 22 are aligned with the central axis A1. It will be appreciated that any number and configuration of shaft holes 14, 16 may be provided.

Figure 11A:
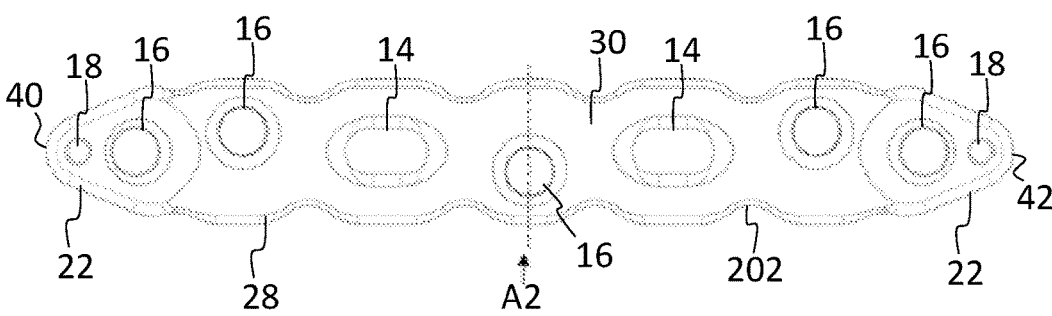
FIGS. 11A-11B show one or more middle polyaxial locking holes for plates with even or odd numbers of fastener openings in some standard straight plates.
Figure 11B:
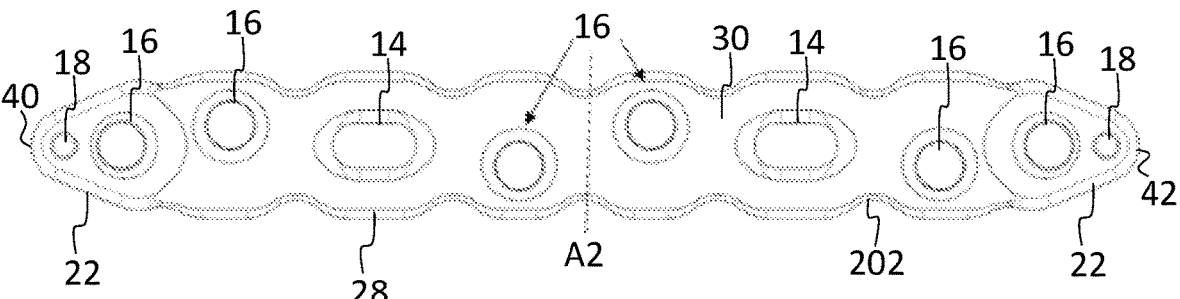

As shown in FIGS. 11A-11B, standard straight plates 200 with at least six fastener holes 14, 16 may have two compression slots 14 positioned one or two holes 14, 16 from the transverse plane A2 of the plate 200, depending if there is an even or odd number of holes 14, 16. As shown in FIG. 11A, an odd number of holes 14, 16 may result in a middle polyaxial locking hole 16 with compression slots 14 on either side of the middle locking hole 16. As shown in FIG. 11B, an even number of fastener holes 14, 16 may result in two middle locking holes 16 and compression slots 14 adjacent to the middle locking holes 16. Compression slots 14 are symmetric about the transverse plane A2 of the plate 200.

Figure 12A:
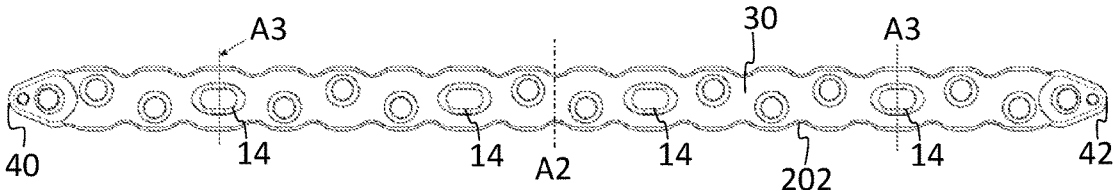
FIGS. 12A-12C show locations for additional compression slots for some longer standard straight plates.
Figure 12B:
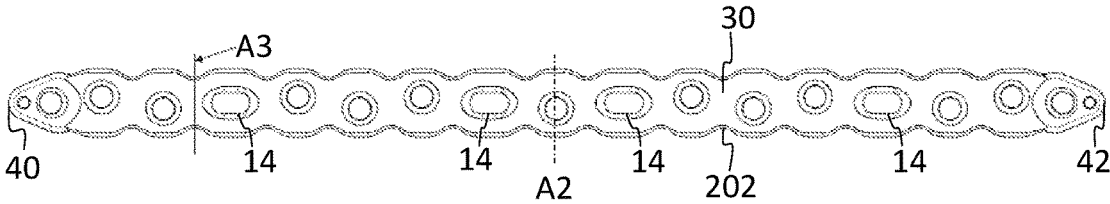
Figure 12C:
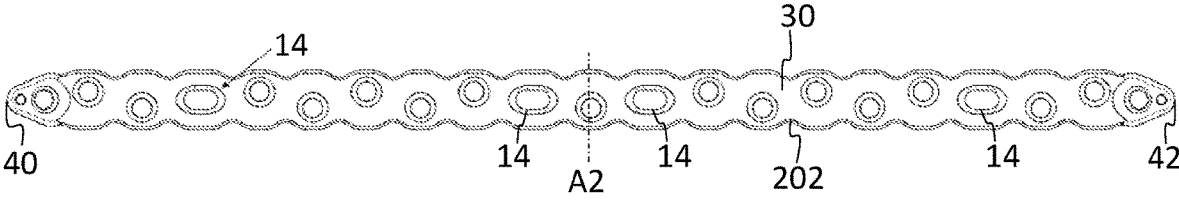

As shown in FIGS. 12A-12C, standard straight plates 200 between ten and eighteen fastener holes 14, 16 may have an additional two compression slots 14. As shown in FIG. 12A, for plates 200 with an even number of fastener openings 14, 16, the additional compression slots 14 may be positioned at the halfway point A3 between the middle compression slot 14 and the end 40, 42 of the plate 200. As shown in FIG. 12B, for plates 200 with an odd number of fastener openings 14, 16, the compression slots 14 may be positioned nearest to the halfway point A3 between the middle compression slot 14 and the end 40, 42 of the plate 200, closest to the transverse plane A2 of the plate 200. As shown in FIG. 12C, standard straight plates 200 with greater than eighteen fastener holes may have a second set of compression slots 14 positioned four holes from the end 40, 42 of the plate 200.

Turning now to FIGS. 13A-17C, several embodiments of broad straight plates 300 are shown in more detail. The broad straight plates 300 are similar to the narrow and standard straight plates 100, 200 with a broader profile where some fastener holes 14, 16 repeat in a 3-hole pattern 304 or other repeating pattern. The broad straight plates 300 are suitable for the fixation of various straight bones, such as the humerus and tibia. The broad straight plates 300 have no curve when viewed in the top plane but may be contoured by the surgeon if desired.

As shown in FIGS. 13A-13E, the broad straight plates 300 may include scalloped edges 302 similar to the narrow and standard straight plates 100, 200. The spacing between scallops 302 surrounding the dynamic compression slots 14 may be greater than the spacing between scallops 302 surrounding the locking holes 16 due to the added length L in the large fragment dynamic compression slots 14. As best seen in FIG. 15B, the broad straight plates 300 may have a scalloped pattern 302 that is offset with respect to the central hole in the 3-hole pattern 304 to preserve the periosteum and offer a more consistent strength across the length of the plate 300. The staggered scallops 302 may allow for greater strength in the cross sections with holes therethrough.

Figure 14A:
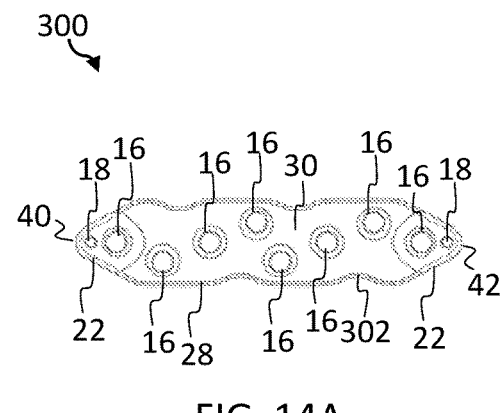
FIGS. 14A-14C show 8-hole, 11-hole, and 29-hole versions, respectively, of the broad straight plates.
Figure 14B:
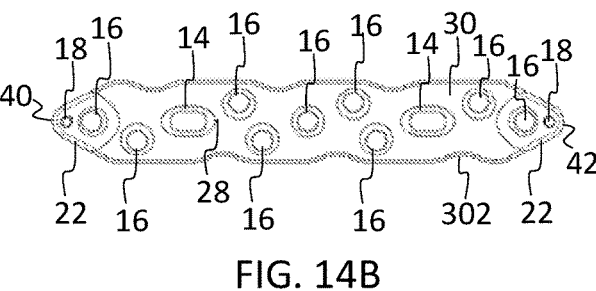
Figure 14C:
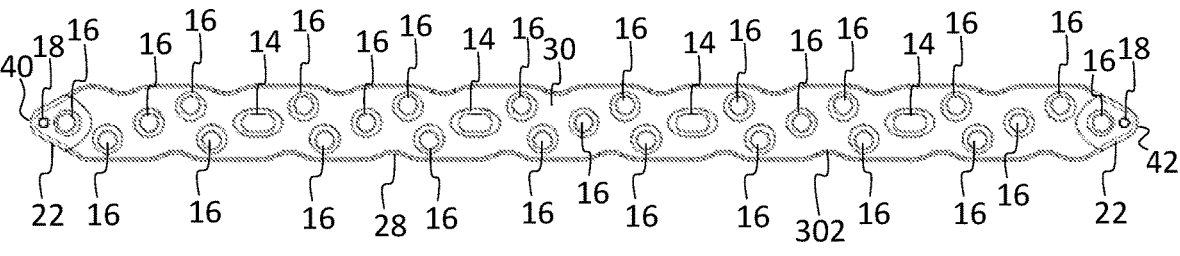

FIGS. 14A-14C show versions of the 4-hole, 7-hole, and 11-hole broad straight plates 300. The broad straight plates

300 may have no compression slots 14, two compression slots 14, or four compression slots 14 depending on the plate length. As shown in FIG. 14A, broad straight plates 300 with less than eight fastener holes 14, 16 may only have polyaxial holes 16. As shown in FIG. 14B, broad straight plates 300 with eleven to twenty-six fastener holes 14, 16 may have two compression slots 14 while the remaining holes are polyaxial holes 16. As shown in FIG. 14C, broad straight plates 300 with greater than twenty-six fastener holes 14, 16 may have four compression slots 14 while the remaining holes are polyaxial holes 16.

Figure 15A:
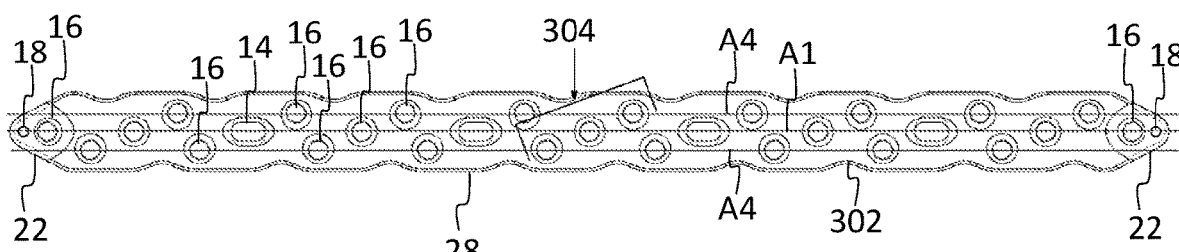
FIGS. 15A-15B show a 3-hole repeating pattern with offset scallops according to one embodiment.
Figure 15B:
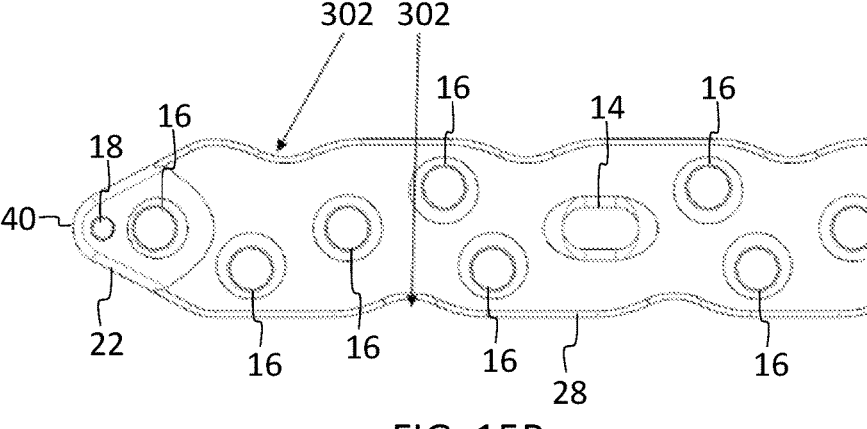
Figure 16A:
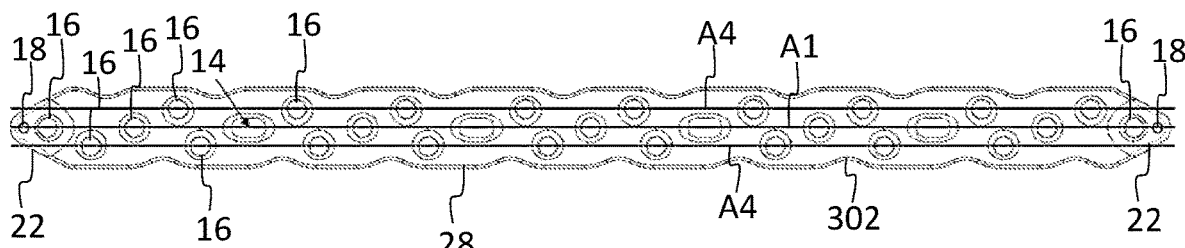
FIGS. 16A-16B show versions of the broad straight plates having central compression slots and offset compression slots, respectively.

FIG. 15A shows positioning of the shaft holes 14, 16 in the broad plates 300 according to one embodiment. The broad straight plates 300 may include 3-hole patterns 304 in which compression slots 14 are coincident with the central axis A1 of the plate 300. Each 3-hole pattern 304 may be arranged on a slope or angle. The 3-hole pattern 304 may include a series of three polyaxial holes 16 and/or a series including a first polyaxial hole 16, a central compression slot 14, and a second polyaxial hole 16. In this embodiment shown, these two types of 3-hole patterns 304 are also repeated along the length of the shaft 28. The central axis A1 may define alternating polyaxial holes 16 and compression slots 14. As shown in FIG. 16A, the shaft 28 of the broad straight plates 300 may have compression slots 14 that are all coincident to the central axis A1 of the plate 300. Some of the polyaxial openings 16 in the series (e.g., upper polyaxial holes) are aligned with a first offset axis A4 and some of the polyaxial openings 16 (e.g., lower polyaxial holes) are aligned with a second offset axis A4. The polyaxial holes 16 and K-wire holes 18 in the beveled or tapered ends 22 are aligned with the central axis A1.

Figure 16B:
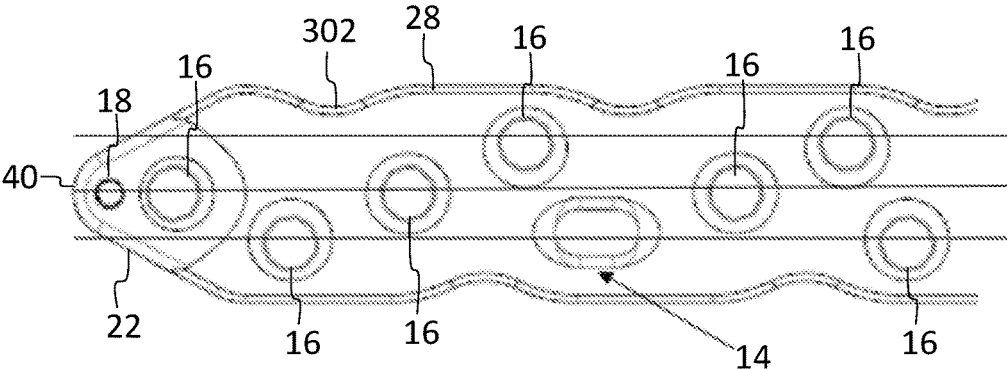

In an alternative embodiment shown in FIG. 16B, the shaft 28 of the broad straight plates 300 may also have compression holes 14 that are offset from the central axis A1 of the plate 300. In this embodiment, the 3-hole repeating pattern has been modified to include a first series of polyaxial holes 16 followed by a series with compression slot 14 and two polyaxial holes 16. The holes 14, 16 may also deviate with respect to the offset axes A4.

Figure 17A:
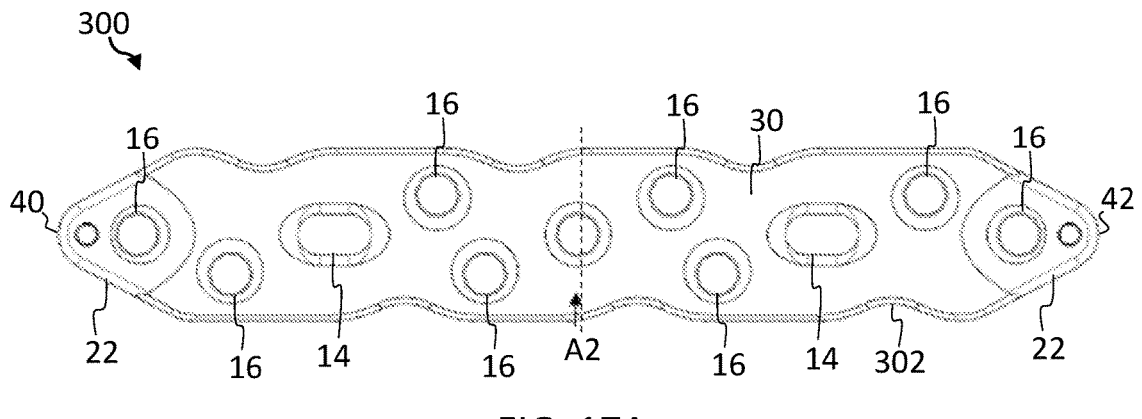
FIGS. 17A-17C show examples of the broad straight plates with central locking holes and compression slot locations for plates with even and odd numbers of fastener holes.
Figure 17B:
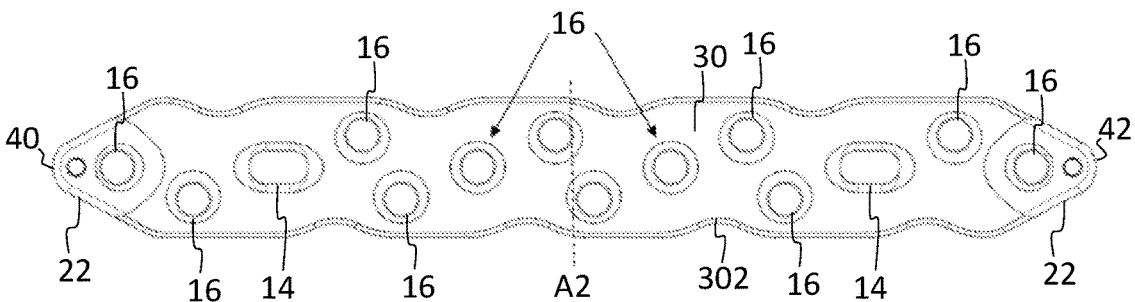
Figure 17C:
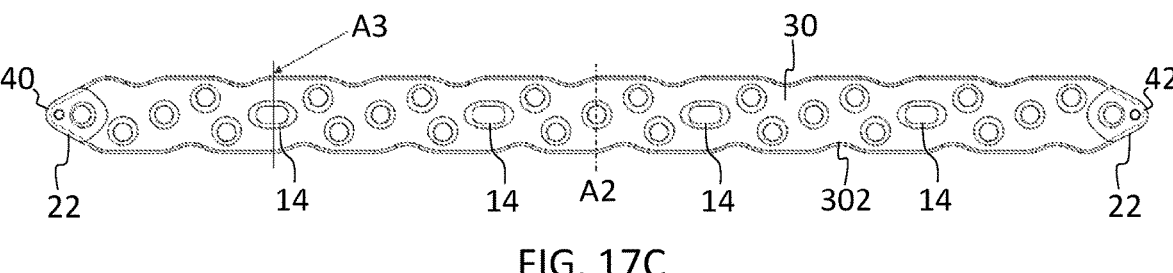
Figure 18A:
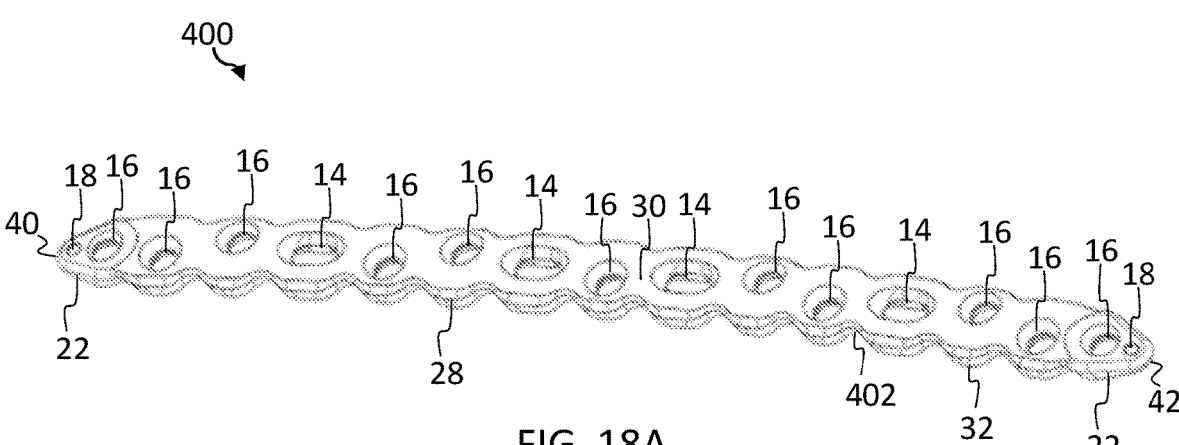
FIGS. 18A-18E show a perspective view, top view, front view, right view, and bottom view, respectively, of a standard curved plate according to one embodiment.
Figure 18B:
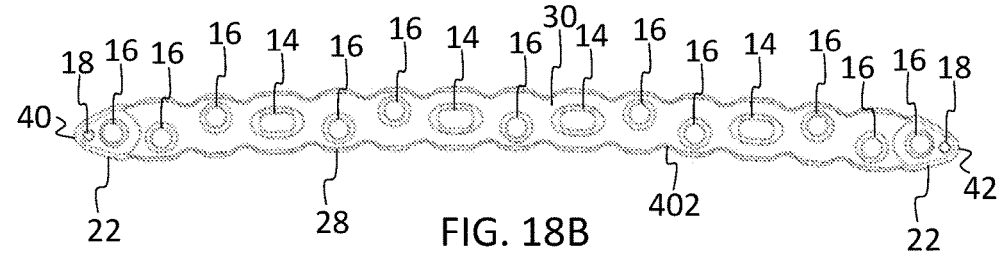
Figures 18C, 18D:
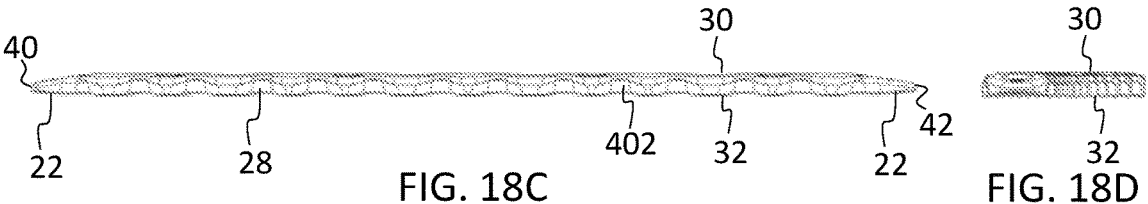
Figure 18E:
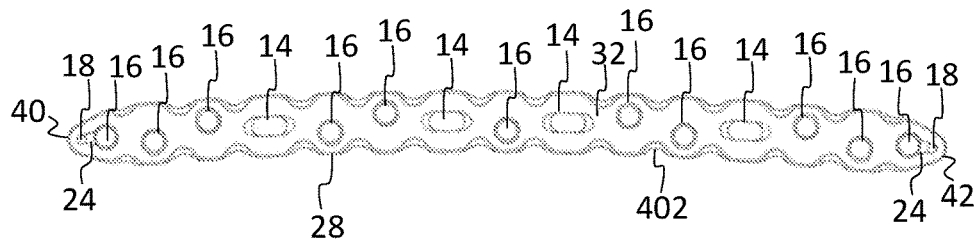

Turning now to FIGS. 17A-17B, broad straight plates 300 with at least eight fastener holes 14, 16 may have two middle compression slots 14 positioned one or two central holes 14, 16 from the transverse plane A2 of the plate 300, depending if there is an even or odd number of central holes. As shown in FIG. 17A, an odd number of central holes 14, 16 may result in a middle polyaxial locking hole 16 and middle compression slots 14 one central hole 16 away from the transverse plane A2. As shown in FIG. 17B, an even number of central holes 14, 16 may result in two middle locking holes 16 and middle compression slots 14 adjacent to those central locking holes 16. Compression slots 14 may be symmetric about the transverse plane A2 of the plate 300. As shown in FIG. 17C, broad straight plates 300 with more than twenty-six screw holes 14, 16 may have an additional two compression slots 14. These slots 14 may be positioned on central holes that are halfway A3 between the middle compression slot 14 and the end 40, 42 of the plate 300.

Turning now to FIGS. 18A-20E, several embodiments of standard curved plates 400 are shown in more detail. The standard curved plates 400 are similar to the standard straight plates 200 but with a curved profile. The standard curved plates 400 are suitable for the fixation of various long bones, such as the femur. The curved plates 400 may have a radius of curvature to match a patient's femora curve in the lateral plane or other suitable curvature. For example, the central axis A1 may follow a constant radius of curvature having the same radius throughout its entire length between ends 40, 42. Alternatively, the central axis A1 may have varying radii of curvature where the curve may be sharper in some areas or broader in others.

As shown in FIGS. 18A-18E, the standard curved plates 400 may include scalloped edges 402, similar to the standard straight plates 200, to preserve the periosteum and offer a more consistent strength across the length of the plate 400. The distance between the center axis of a locking hole 16 and dynamic compression slot 14 may be larger to account for the added length L of the dynamic compression slots 14. Similarly, the spacing between scallops 402 surrounding dynamic compression slots 14 may be greater than the spacing between scallops 402 surrounding locking holes 16 due to the added length L of the dynamic compression slots 14.

Figure 19A:
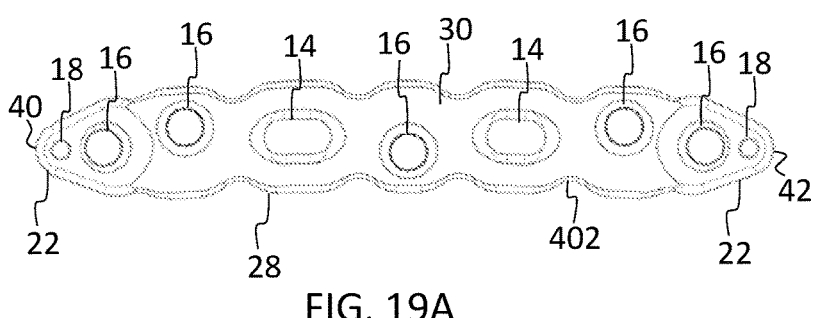
FIGS. 19A-19B show 11-hole and 15-hole versions, respectively, of the standard curved plates.
Figure 19B:
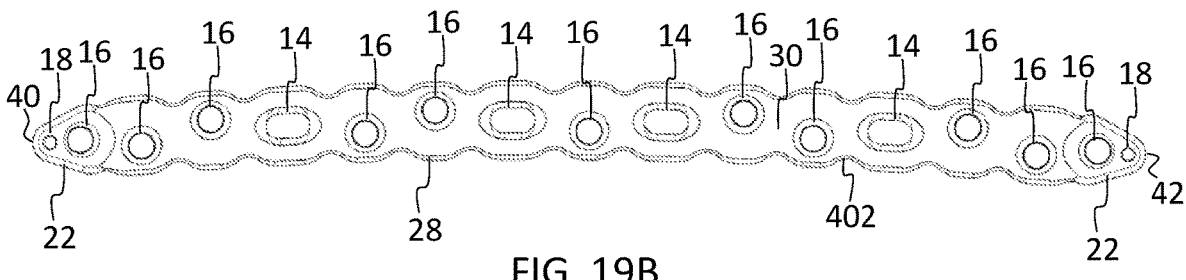

As shown in FIGS. 19A-19B, the standard curved plates 400 may have two compression slots 14 or four compression slots 14 depending on the plate length. Standard curved plates 400 with nine to ten fastener holes 14, 16 may have two compression slots 14 while the remaining holes are polyaxial holes 16 (e.g., 4.5 mm polyaxial holes). Standard curved plates 400 with greater than ten fastener holes 14, 16 may have four compression slots 14 while the remaining holes are polyaxial holes 16.

Figure 20A:
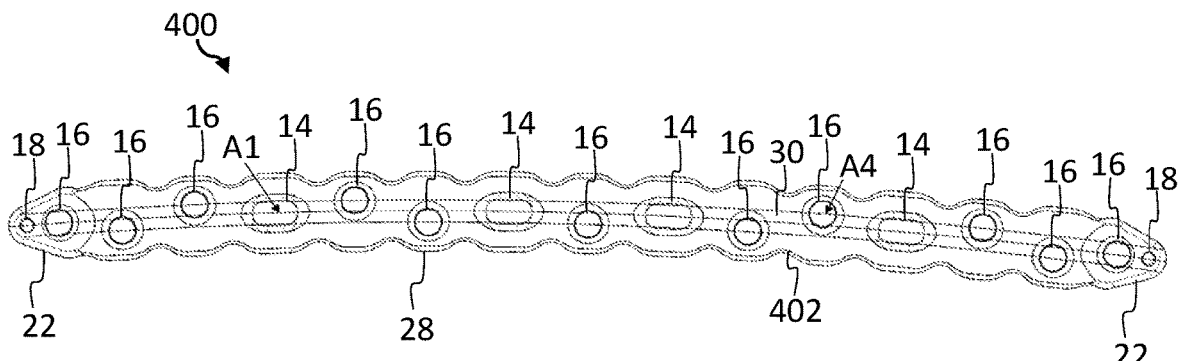
FIGS. 20A-20E show examples of the standard curved plates with central locking holes and compression slot locations for even and odd holes.

As shown in FIG. 20A, the shaft 28 of the standard curved plates 400 may have polyaxial locking holes 16 that are all offset from the central axis A1 of the plate 400, while the compression slots 14 are coincident with the central axis A1 of the plate 400. The offset axis A4 may be aligned parallel to axis A1, following the same curvature and maintaining a consistent distance from one another throughout their lengths, but offset relative to central axis A1. As shown in FIG. 20A, some of the polyaxial openings 16 (e.g., four upper polyaxial holes) are aligned with a first offset axis A4 and some of the polyaxial openings 16 (e.g., five lower polyaxial holes) are aligned with a second offset axis A4. The compression slots 14 (e.g., four compression slots) may be provided coincident with the central axis A1 of the plate 200. The polyaxial holes 16 and K-wire holes 18 in the beveled or tapered ends 22 are aligned with the central axis A1. Alternatively, the standard curved plates 400 may have all shaft holes offset from the central axis A1 of the plate, similar to the embodiment shown in FIG. 10B.

Figure 20B:
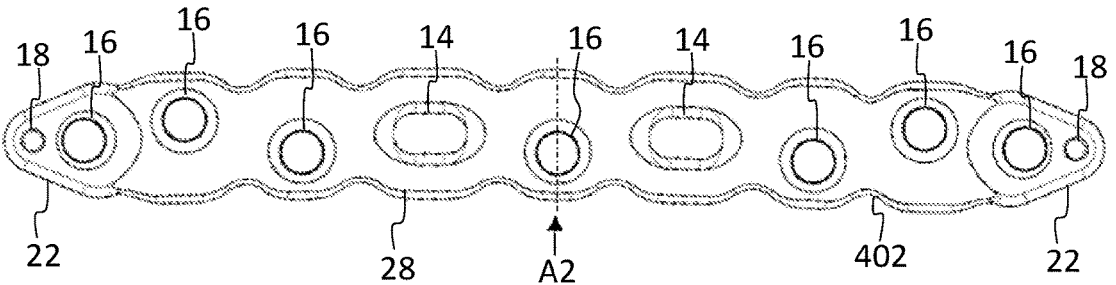
Figure 20C:
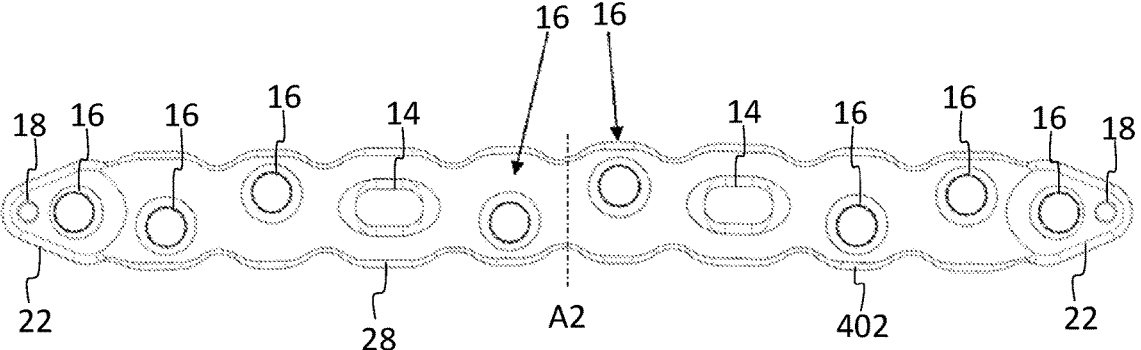

With emphasis on FIGS. 20B-20C, the standard curved plates 400 may have two compression slots 14 positioned one or two holes offset from the transverse plane A2 of the plate 400, depending if there is an even or odd number of fastener holes 14, 16. As shown in FIG. 20B, an odd number of holes 14, 16 may result in a single middle polyaxial locking hole 16 with compression slots 14 on either side of the middle locking hole 16. As shown in FIG. 20C, an even number of holes 14, 16 may result in two middle locking holes 16 with compression slots 14 adjacent to those middle locking holes 16. The compression slots 14 may be symmetric about the transverse plane A2 of the plate 400.

Figure 20D:
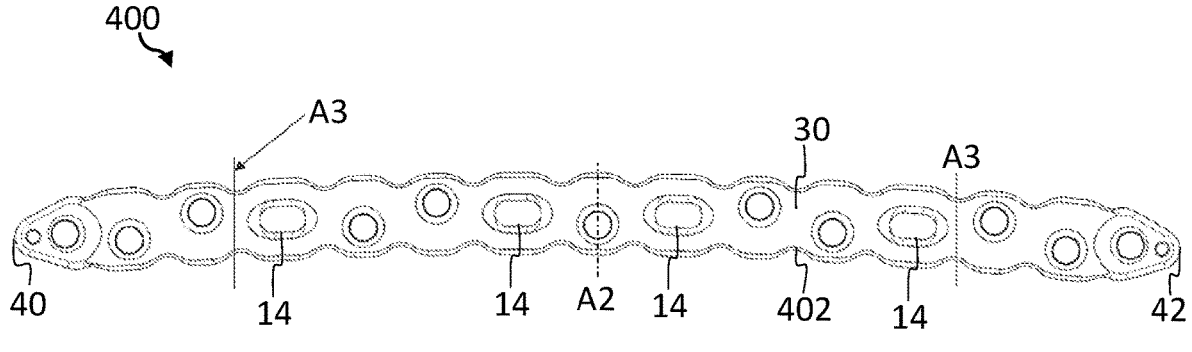
Figure 20E:
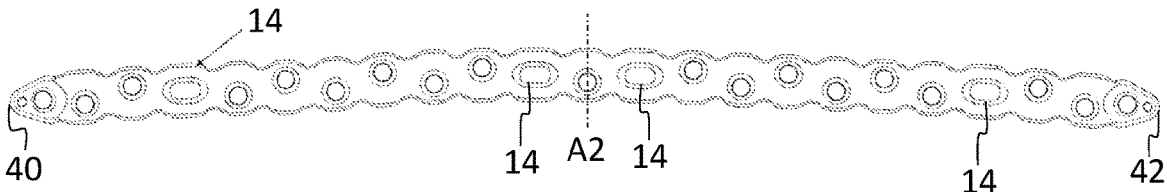
Figures 21A, 21B, 21C, 21D, 21E:
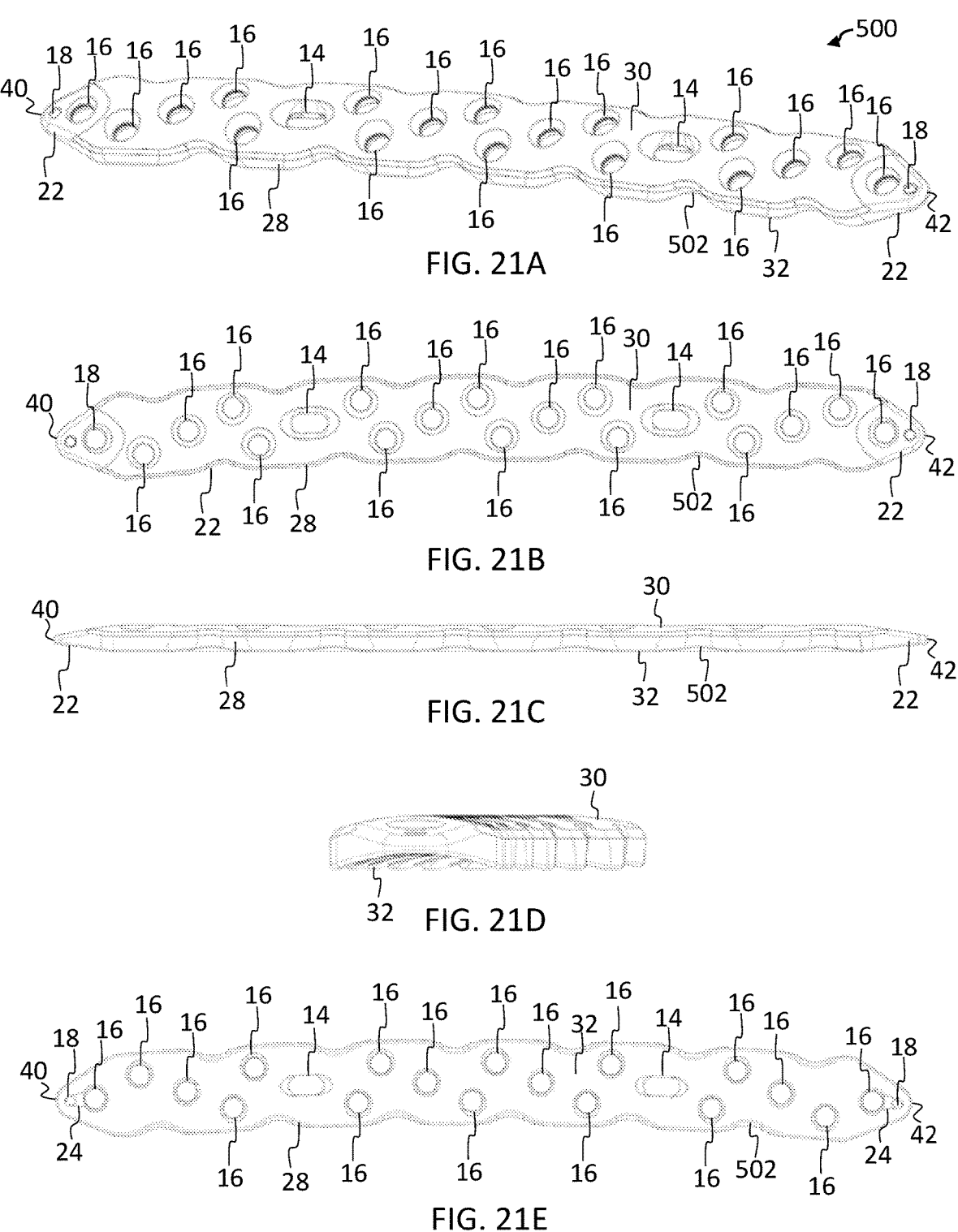
FIGS. 21A-21E show a perspective view, top view, front view, right view, and bottom view, respectively, of a broad curved plate according to one embodiment.

Standard curved plates 400 between ten and eighteen fastener holes may have an additional two compression slots 14. As shown in FIG. 20D, additional slots 14 may be positioned nearest to the halfway point between the middle compression slot 14 and the end 40, 42 of the plate 400, closest to the transverse plane A2 of the plate 400. As shown in FIG. 20E, standard curved plates 400 with greater than eighteen fastener holes may have an additional two compression slots 14 positioned four holes from the end 40, 42 of the plate 400.

Turning now to FIGS. 21A-24D, several embodiments of broad curved plates 500 are shown in more detail. The broad curved plates 500 are similar to the broad straight plates 300 but with a curved profile. The broad curved plates 500 are suitable for the fixation of various long bones, such as the femur. The broad curved plates 500 may have a constant radius of curvature to match a patient's femora curve in the lateral plane or other suitable curvature.

Figure 22A:
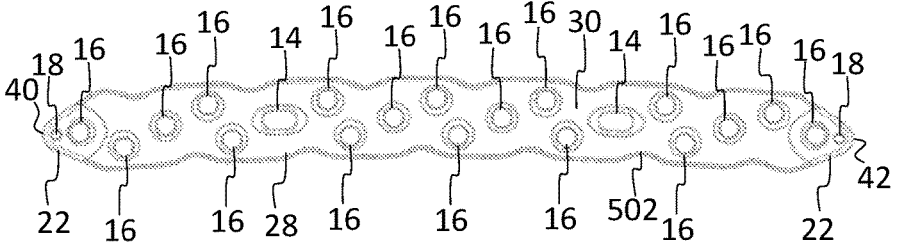
FIGS. 22A-22B show 14-hole and 29-hole versions, respectively, of the broad curved plates.
Figure 22B:
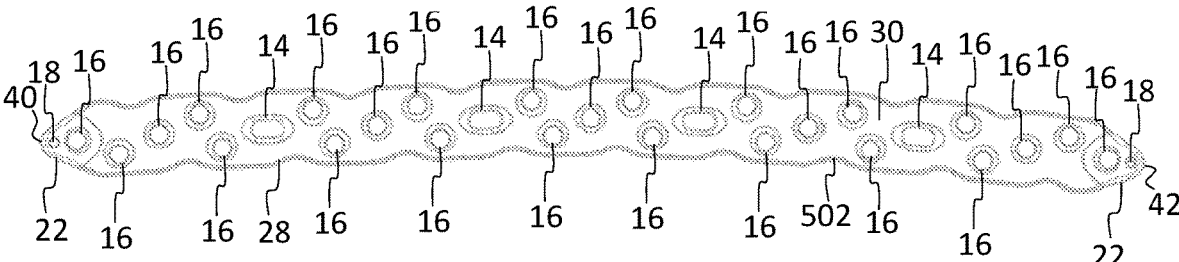

As shown in FIGS. 22A-22B, the broad curved plates 500 may have two compression slots 14 or four compression slots 14 depending on the plate length. As shown in FIG. 22A, broad curved plates 500 with eleven to twenty-six fastener holes may have two compression slots 14 while the remaining holes are polyaxial holes 16. As shown in FIG. 22B, broad curved plates 500 with greater than twenty-six fastener holes may have four compression slots 14 while the remaining holes are polyaxial holes 16.

Figure 23A:
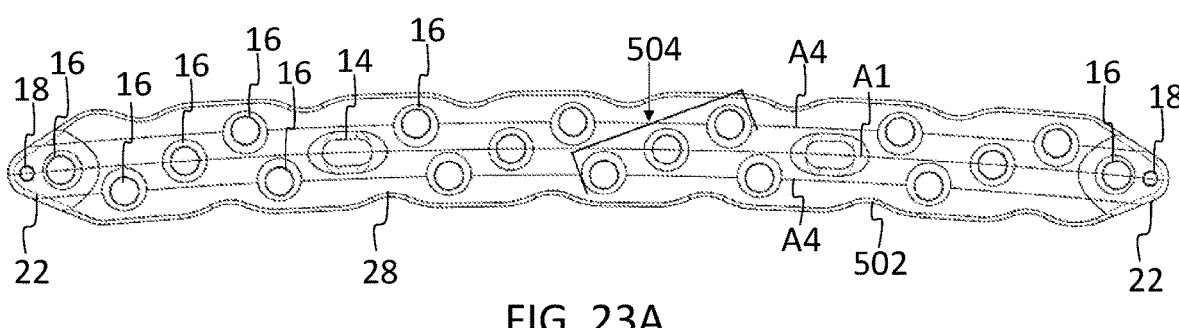
FIGS. 23A-23B show a 3-hole repeating pattern with offset scallops according to one embodiment.

As shown in FIG. 23A, the broad curved plates 500 may include 3-hole repeating patterns 504, similar to patterns 304. Each 3-hole pattern 504 may be arranged on a slope or angle. The 3-hole patterns 504 may include a series of three polyaxial holes 16 and/or a series including a first polyaxial hole 16, a central compression slot 14, and a second polyaxial hole 16. In the embodiment shown, these two types of 3-hole patterns 504 are also repeated along the length of the shaft 28. Depending on the number of holes 14, 16, the central axis A1 may define alternating polyaxial holes 16 and compression slots 14. Some of the polyaxial openings 16 in the series (e.g., upper polyaxial holes) are aligned with a first curved offset axis A4 and some of the polyaxial openings 16 (e.g., lower polyaxial holes) are aligned with a second curved offset axis A4. The polyaxial holes 16 and K-wire holes 18 in the beveled or tapered ends 22 are aligned with the central curved axis A1.

Figure 23B:
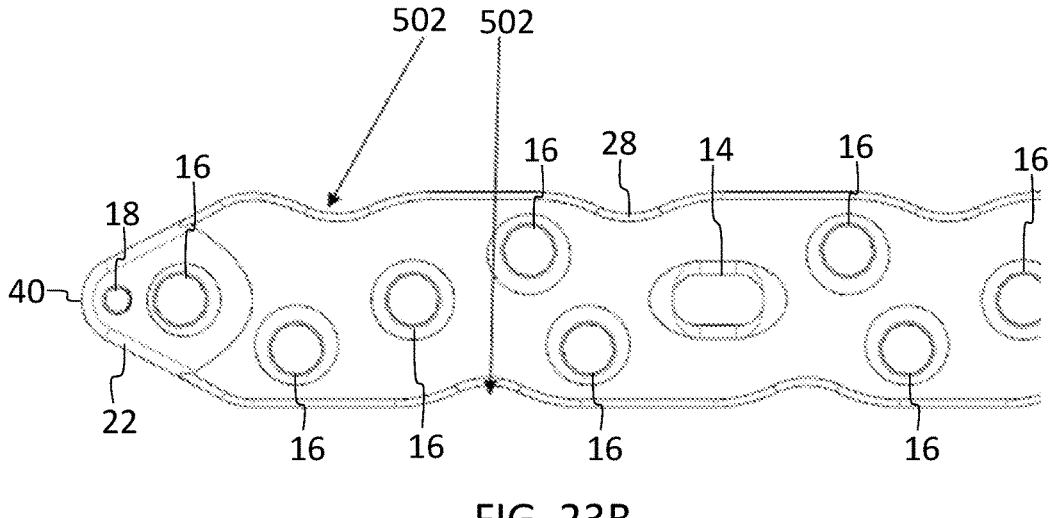

The broad curved plates 500 may include scalloped edges 502, similar to the broad straight plates 300, to preserve the periosteum and offer a more consistent strength across the length of the plate 500. The spacing between scallops 502 surrounding dynamic compression slots 14 may be greater than the spacing between scallops 502 surrounding locking holes 16 due to the length L of the large fragment dynamic compression slots 14. As best seen in FIG. 23B, the broad curved plates 500 may have a scalloped pattern 502 that is offset with respect to the central hole in the 3-hole pattern 504 with the purpose of making the plate 500 stronger at the cross sections of the plate with holes. In particular, the staggered scallops 502 may allow for greater strength in the cross sections with holes therethrough.

Figure 24A:
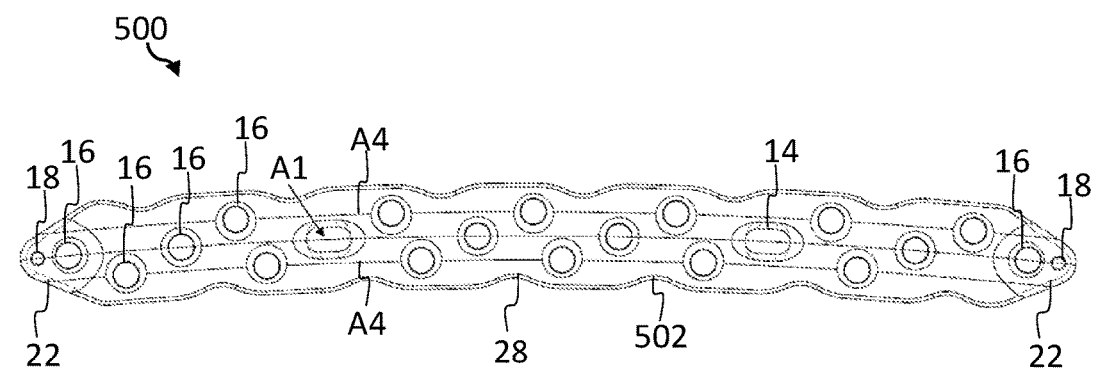
FIGS. 24A-24D show examples of the broad curved plates with central locking holes and compression slot locations for even and odd holes.

The shaft 28 of the broad curved plates 500 may have compression slots 14 that are coincident to the curved central axis A1 of the plate 500 or may have compression slots 14 that are offset from the curved central axis A1 of the plate 500. As shown in FIG. 24A, the compression slots 14 are all coincident with the curved central axis A1 of the plate 500. Alternatively, the shaft 28 of the broad curved plates 500 may also have compression holes 14 that are offset from the central axis A1 of the plate, similar to FIG. 16B.

Figure 24B:
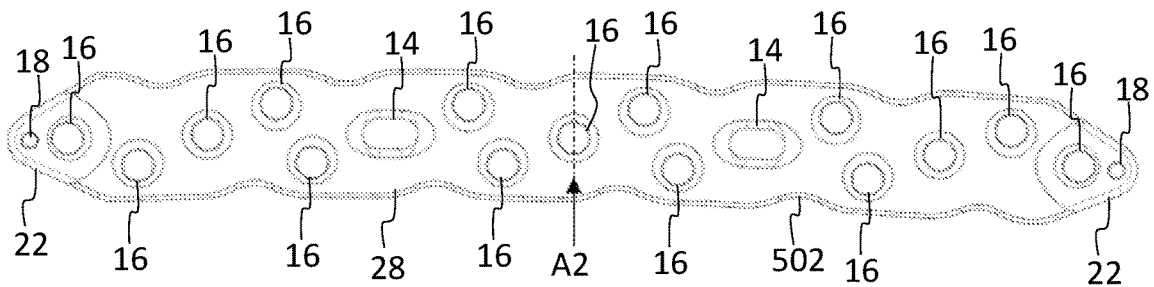
Figure 24C:
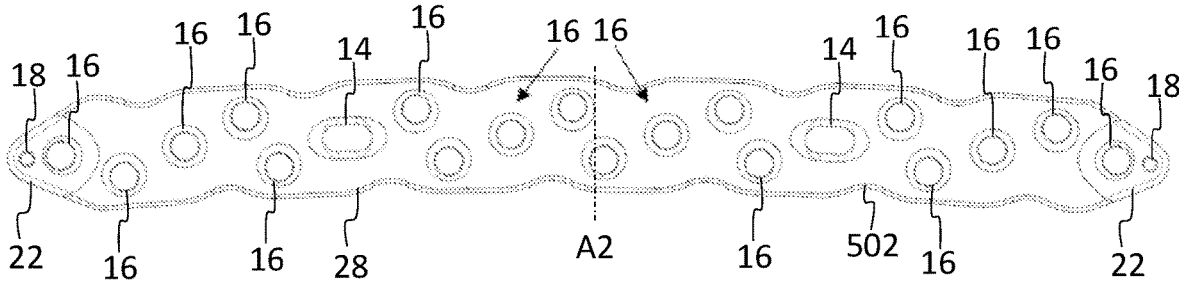
Figure 24D:
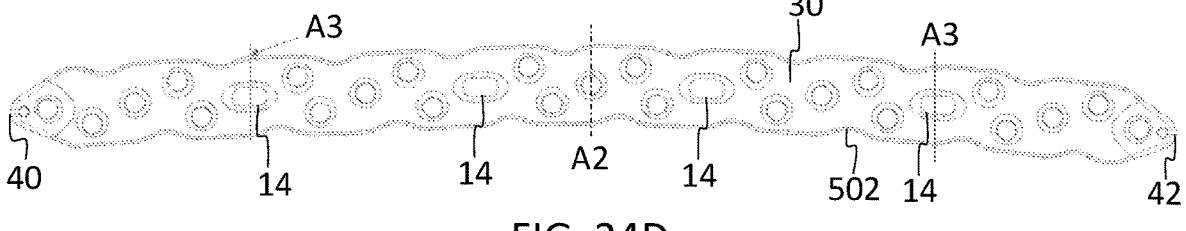

With emphasis on FIGS. 24B-24C, the central holes of the broad curved plates 500 may be polyaxial locking holes 16. The broad curved plates 500 may have two middle compression slots 14 positioned one or two central holes 16 offset from the transverse plane A2 of the plate 500, depending if there is an even or odd number of central holes 16. As shown in FIG. 24B, an odd number of central holes 16 may result in a middle polyaxial locking hole aligned with transverse axis A2. The middle compression slots may be located at least one central hole away from the transverse plane A2. As shown in FIG. 24C, an even number of central holes 16 may result in two middle locking holes 16 adjacent to or intersecting the transverse axis A2. The middle compression slots 14 may be located adjacent to the middle series of locking holes 16. The compression slots 14 may be symmetric about the transverse plane A2 of the plate 500. The broad curved plates 500 with more than twenty-six screw holes 14, 16 may have an additional two compression slots 14. As shown in FIG. 24D, the additional slots 14 may be positioned on central holes 14 that are halfway A3 between the middle compression slot 14 and the end 40, 42 of the plate 500.

Turning now to FIGS. 25A-27D, several embodiments of metaphyseal plates 600 are shown in more detail. In this embodiment, only one end 40 includes tapered end 22 with polyaxial hole 16 and K-wire hole 18 therethrough, the opposite end 42 includes a thin metaphyseal portion 604 and a transition region 606 with smaller diameter polyaxial holes 16 configured to secure the plate 600 to metaphyseal bone. The metaphyseal plates 600 are suitable for the fixation of various long straight bones, such as the humerus and tibia. Metaphyseal plates 600 are configured to sit on both the metaphyseal portion of a long bone and the diaphysis or shaft. The metaphyseal plates may be indicated for extra-articular fractures of the metaphyseal area that extend into the shaft. For example, the plates 600 may include 3.5 mm and 4.5 mm metaphyseal plates indicated for distal tibial and proximal humeral fractures. It will be appreciated that the plate size and suitable placement may be selected by the surgeon.

As shown in FIGS. 25A-25E, the metaphyseal plates may be separated into three segments: a metaphyseal portion 604, a transition region 606, and a diaphyseal portion 608. The diaphyseal portion 608 may be similar to the shaft portion 28 in other embodiments. The metaphyseal plates 600 may have scalloped edges 602 configured to preserve the periosteum and offer a more consistent strength across the length of the plate 600. The spacing between scallops 602 surrounding dynamic compression slots 14 may be greater than the spacing between scallops 602 surrounding locking holes 16 due to the added length L of the large fragment dynamic compression slots 14.

Figure 26A:
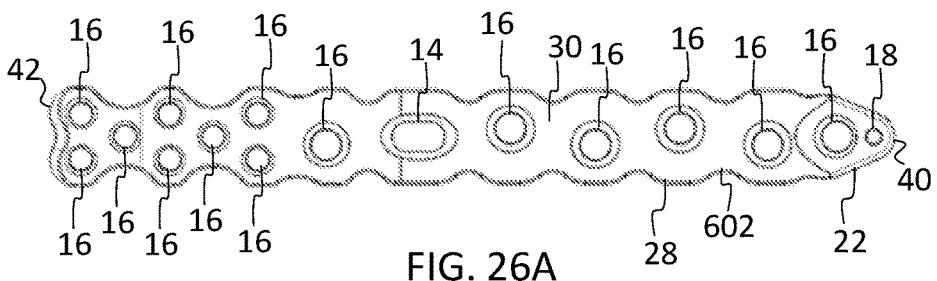
FIGS. 26A-26B show 7-hole and 10-hole versions, respectively, of the metaphyseal plates.
Figure 26B:
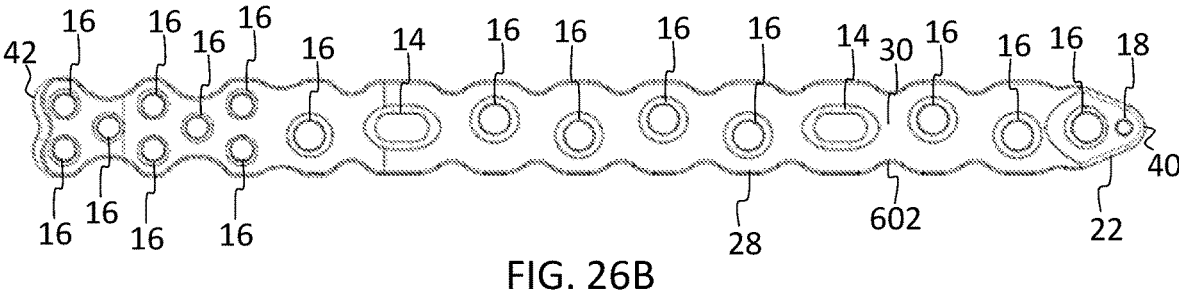

As shown in FIGS. 26A-26B, the metaphyseal plates 600 may have one or two compression slots 14 depending on the plate length. As shown in FIG. 26A, smaller metaphyseal plates 600, for example, with less than eight diaphyseal polyaxial holes 16 (e.g., 4.5 mm holes), may have one compression slot 14 while the remaining holes are polyaxial holes 16. As shown in FIG. 26B, larger metaphyseal plates 600 with at least eight diaphyseal polyaxial holes 16 (e.g., 4.5 mm holes) may have two compression slots 14 while the remaining holes are polyaxial holes 16.

Figure 27A:
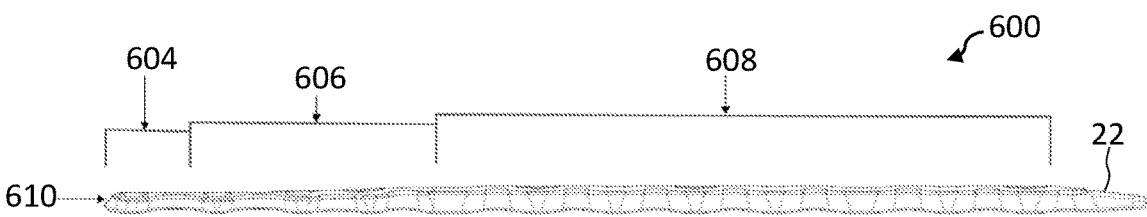
FIGS. 27A-27D show examples of the metaphyseal plates with central compression slots and a tapered plate thickness.
Figure 27B:
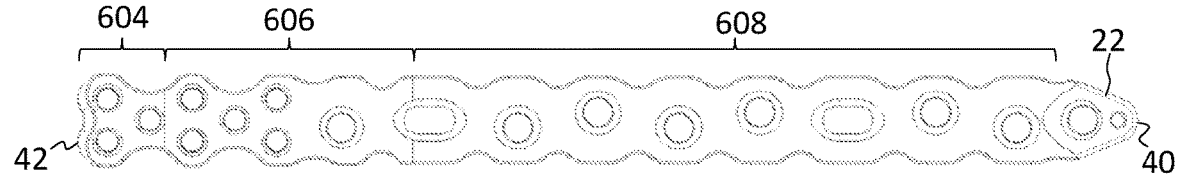

Turning now to FIGS. 27A-27B, the three segments of plate 600 are shown in more detail. The first metaphyseal segment 604 has a thin section to sit on the metaphyseal portion of the bone. The metaphyseal portion 604 may define three polyaxial holes 16 (e.g., 3.5 mm holes) having diameters smaller than the polyaxial holes 16 (e.g., 4.5 mm holes) in the diaphyseal portion 608. The three polyaxial holes 16 may be arranged in a triangular pattern, for example, where the axis of each hole 16 forms the vertices of an equilateral triangle. The tip or edge 610 of the thinnest metaphyseal portion 604 may be tapered or beveled. The tapered edge 610 may help to aid in submuscular implantation of the plate 600.

The second transition segment 606 has a transition in thickness between the thinnest metaphyseal portion 604 and the thickest diaphyseal portion 608. The transition portion 606 may include five polyaxial holes 16 (e.g., 3.5 mm holes) and one locking hole 16 (e.g., 4.5 mm locking hole). The five polyaxial holes 16 may be located closer toward the metaphyseal portion 604 and arranged in an X-like configuration. The small diameter polyaxial holes 16 of the metaphyseal and transition segments 606 may be symmetrical about the central axis A1 of the plate 600. The single larger locking hole 16 may be located closer to the diaphyseal portion 608 and aligned with polyaxial holes 16 in that section 608. The location of the holes 16 in the transition region 606 and length of the transition region 606 may aid in uniform bending.

The third diaphyseal segment 608 has the thickest portion. The diaphyseal portion 608 may be similar to the shaft 28 in the other embodiments. The diaphyseal portion 608 may have a varying number of locking holes 16 (e.g., 4.5 mm holes) and compression slots 14. The end 40 of the diaphyseal portion 608 may include beveled or tapered region 22. The tapered region 22 may decrease in thickness from the shaft toward the diaphyseal end of the plate 10. The tapered region 22 may define polyaxial hole 16 and guide wire hole 18 with a swept cut 24 on the underside of the hole 16.

Figure 27C:
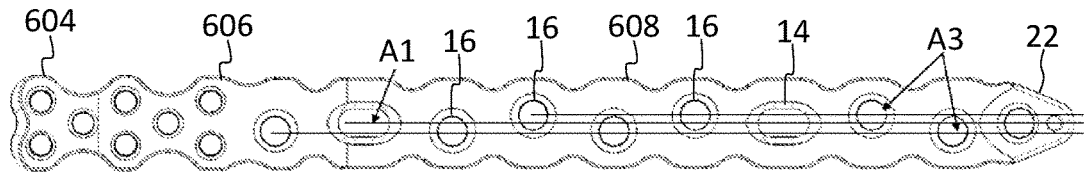

As shown in FIG. 27C, the metaphyseal plates 600 may have a two row hole pattern where the locking shaft holes 16 are offset to one another. The metaphyseal plates 600 may have up to three varying amounts of displacement from the center axis A1 of the plate 600. In one embodiment, the shaft of the diaphyseal section 608 may include polyaxial locking holes 16 that are all offset from the central axis A1 of the plate 600, while the compression slots 14 are coincident with the central axis A1 of the 600. For example, a first set of polyaxial holes 16 may be aligned with offset axis A3 above the center axis A1 and a second set of polyaxial holes 16 may be aligned with offset axis A3 below the center axis A1. Alternatively, the metaphyseal plates 600 may have locking holes 14, 16 that are all offset from the central axis A1 of the plate 600.

Figure 27D:
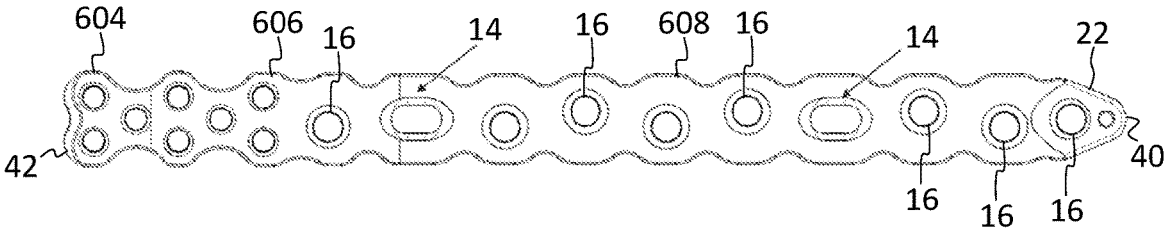

The metaphyseal plates 600 with at least eight diaphyseal holes 16 may have one compression slot 14 positioned two holes 16 or three holes away from the transition region 606. Metaphyseal plates 600 with greater than seven diaphyseal holes 16 may have an additional compression slot 14. As shown in FIG. 27D, the compression slot 14 may be positioned as the fourth hole 14 from the end 40 of the plate 600. It will be appreciated that the openings 14, 16 may be located at suitable locations along the length of the plate 600 to secure the plate 600 to metaphyseal and diaphyseal bone.

The large fragment bone plates described herein may allow for compression of a fracture using an external instrument through the plate within the length of the compression slots. This prevents the need to enlarge the incision past the length of the implant to use an articulating tensioning device, to apply direct reduction with clamps, to use a lag screw as a fracture reduction technique, or other surgical methods where the user must restore the length of the fracture before implanting the plate.

Figure 28A:
FIGS. 28A-28B show perspective views of a fracture reduction instrument in a starting position and ending position, respectively, configured to apply compression and/or distraction according to one embodiment.
Figure 28B:
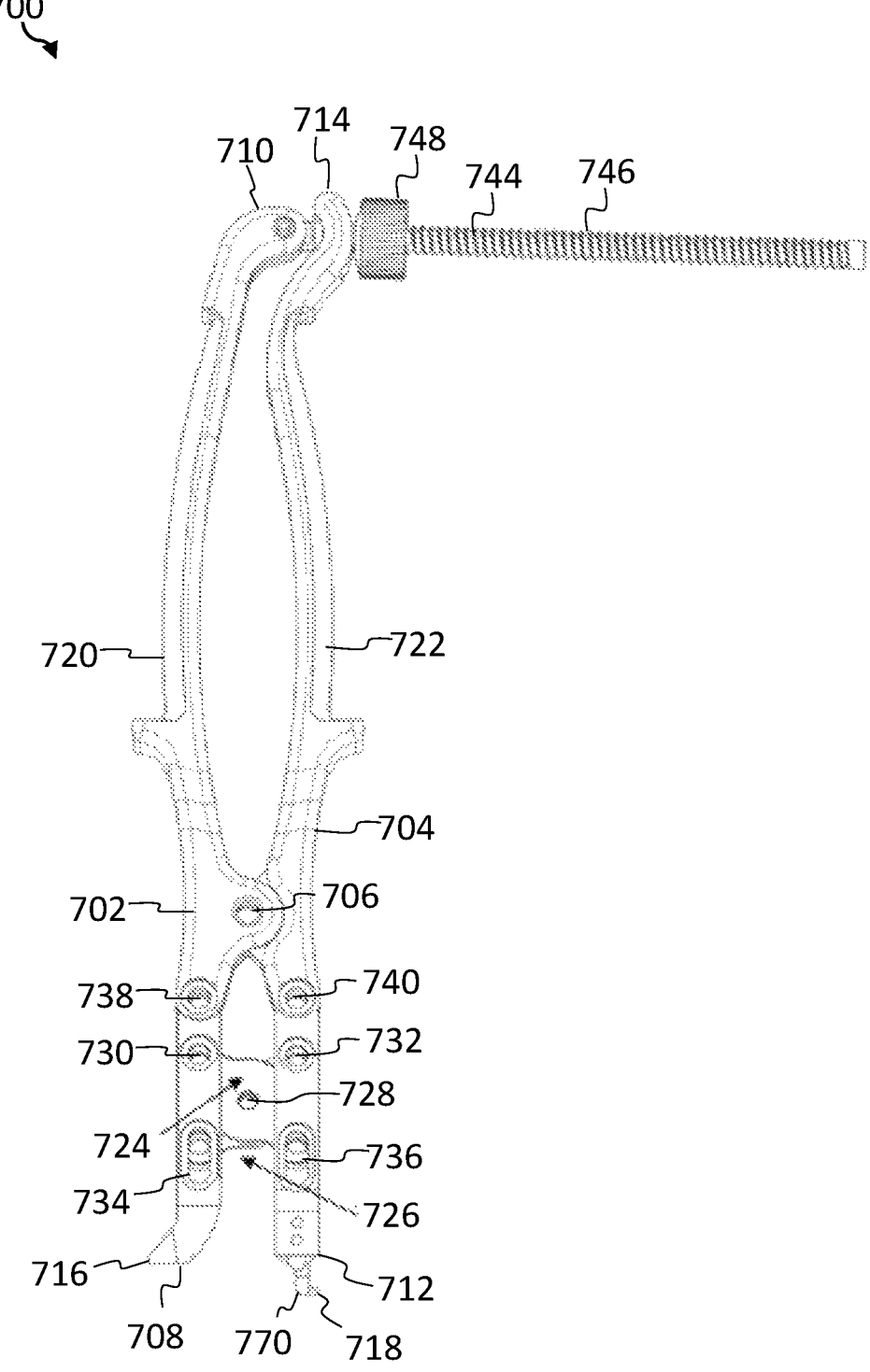

Turning now to FIGS. 28A-28B, a hand-held fracture reduction tool or compression and distraction instrument 700 is shown according to one embodiment. The compression/distraction instrument 700 is configured to provide compression and/or distraction of a fracture through a bone plate. The instrument 700 may permit compression through any plate that defines a compression slot 14 accepting a non-locking screw 12. The instrument 700 may also permit distraction through any plate that includes a polyaxial hole 16 on the tapered end 22 of the plate. The plate may include any of the plate styles 10 described herein or other suitable bone plates. Although generally described with reference to compression and distraction of bone fragments of long bones, such as the femur, humerus, and tibia, it will be appreciated that the instruments and systems described herein may be applied to other orthopedic locations and applications.

The compression/distraction instrument 700 includes a first pivoting arm or translation arm 702 and a second pivoting arm or hook arm 704 coupled at a pivot point 706. The translation arm 702 extends from a first end or distal end 708 to a second end or proximal end 710. Similarly, the hook arm 704 extends from a distal end 712 to a proximal end 714. The distal end 708 of the translation arm 702 includes a screw engaging projection 716. The screw engaging projection 716 may have a curved stem that has an opening or U-shaped slot 717 configured to engage the shaft and/or head of the bone fastener 12. The curved stem of the screw engaging projection 716 may point outward and away from the central axis of the instrument 700. The screw engaging projection 716 may be positioned adjacent to a bone fastener 12, for example, seated against or beneath the head of the fastener 12, thereby temporarily securing the translation arm 702 to the fastener 12.

The distal end 712 of the hook arm 704 includes a plate engaging end or hook 718 configured to engage with the plate 10. The hook 718 may be configured to fit into one hole 16 and hooked under the plate 10, thereby temporarily securing the hook arm 704 to the plate 10. The hook piece 718 may have an L-shaped body with a leg 770 extending longitudinally and distally and then bent into foot 772 extending laterally outward. As best seen in FIG. 29B, the foot 772 may be centered on leg 770 having a width smaller than the width of the leg 770. An upper surface 774 of foot 772 may be rounded with a convex curvature. The upper surface 774 of foot 772 may be sized and dimensioned to fit within the swept cut 24 in the bottom 32 of a plate 10. For example, the hook 718 may be positioned through the polyaxial hole 16 in the tapered end 22 and hooked into swept cut 24 on the underside of the plate 10. The hook 718 may be secured to the distal end 712 of the arm 722 via retention pins or cross pins 719 or other suitable mechanism. The hook 718 and screw engaging projection 716 may point outward and away from one another in opposite directions. The projection 716 and hook 718 form the tip of the instrument 700, which is configured to engage the bone fastener 12 and plate 10, respectively, to impart compression or distraction forces.

FIGS. 29A-29B shows examples of translating distal tips 708, 712 for arms 702, 704, respectively, to accommodate offset distance between the hook 718 and screw 12. The compression/distraction instrument 700 may accommodate offset distance between the hook 718 and the screw 12 due to the ability of translation of the hook piece 718 along the cross pins 719 and the width of the translation arm 702 being wider than the screwhead. As shown in FIG. 29A, the opening or U-shaped slot 717 of the screw engaging projection 716 may have a width greater than the diameter of the screw head. This allow the screw to translate along the width of the slot 717. As shown in FIG. 29B, the hook 718 may be permitted to translate along cross pins 719, thereby allowing the hook 718 to translate within the distal tip 712. The free translation of hook 718 within the hook arm 704 and screw 12 within the translation arm 702 accommodates any offset distance between the hook 718 and screw 12.

The proximal ends 710, 714 of arms 702, 704 are manipulable by a user, such as a surgeon. The translation and hook arms 702, 704 may each define a handle portion 720, 722 with gripping portions, which are configured to be gripped and squeezed by the user. Squeezing the handles 720, 722 together causes the distal ends 708, 712 to spread apart, and spreading the handles 720, 722 in the opposite direction causes the distal ends 708, 712 to come together.

Figures 30A, 30B:
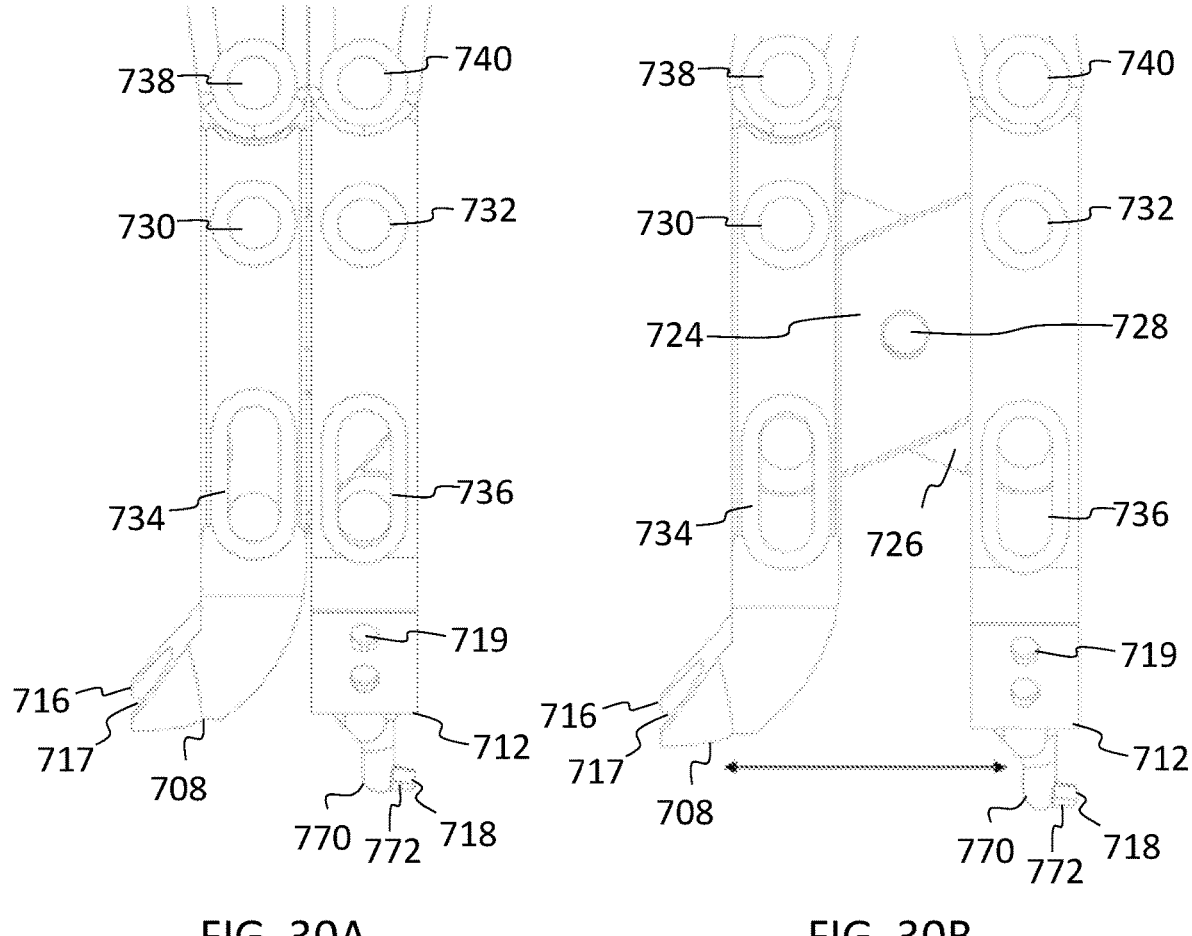
FIGS. 30A-30B show the starting position and ending position, respectively, of the distal tips of the instrument due to a cross-arm linkage system according to one embodiment.

As best seen in FIGS. 30A-30B, the translation and hook arms 702, 704 may be connected together via a cross-arm linkage including first and second cross arms 724, 726 that maintain the arms 702, 704 substantially parallel to one another as they are opened and closed. The first and second cross arms 724, 726 are coupled together at an intermediate pivot point 728 and the ends connect to the respective arms 702, 704 at pivot points 730, 732 and slots 734, 736, respectively. The arms 702, 704 may be segmented at pivot points 738, 740 located between arm pivot point 706 and cross arms 724, 726. In FIG. 30A, the cross arms 724, 726 are folded into one another and retained between the two arms 702, 704. As shown in FIG. 30B, when the handles 720, 722 are squeezed together, the cross arms 724, 726 open with a scissor-type action, forcing pins to slide upward within the slots 734, 736, and thereby spreading the distal ends 708, 712 of arms 702, 704 apart. The compression/distraction instrument 700 is able to produce consistent compression and distraction force due to the parallel motion of the cross-arm linkage system. The first and second cross arms 720, 722 may provide distraction or compression motion that is substantially parallel to the longitudinal axis of the fractured bone, thereby ensuring alignment of the bone fragments.

The fracture reduction instrument 700 may include a locking member 744 positionable between the proximal ends 710, 714 of the arms 702, 704 to maintain a desired distraction or compression force. The locking member 744 may include a spindle or threaded shaft 746 pivotably mounted on the proximal end 710 of arm 702 and passing through the proximal end 714 of arm 704. An internally threaded thumbwheel 748 may rotatably engage with threaded shaft 746 such that movement of the thumbwheel 748 along the threaded shaft 746 fixes a relative position of the arms 702, 704.

FIGS. 31A-31C and 32A-32C show alternative locking members 744 for translation of the fracture reduction instrument 700. The instrument 700 may feature a ratchet 760 or buttress thread 750, 780 for example, to achieve a ratcheting function or threaded function, as opposed to a v-thread that is incorporated in the articulating tensioning device. Both the ratchet 760 and buttress thread 750, 780 provide a quick way to compress the instrument 700. For a one-way ratchet 760, the instrument 700 may only function in one direction and the compression provided increases in discrete increments rather than continuously. The ratchet arm 762 may be easily displaced during operation due to an unintentional upward force on the ratchet arm 762. The advantage of a buttress thread 750, 780 is that threaded advancement can be utilized to provide smaller increments of translation between the hook 718 and screw 12 being leveraged.

Figure 31A:
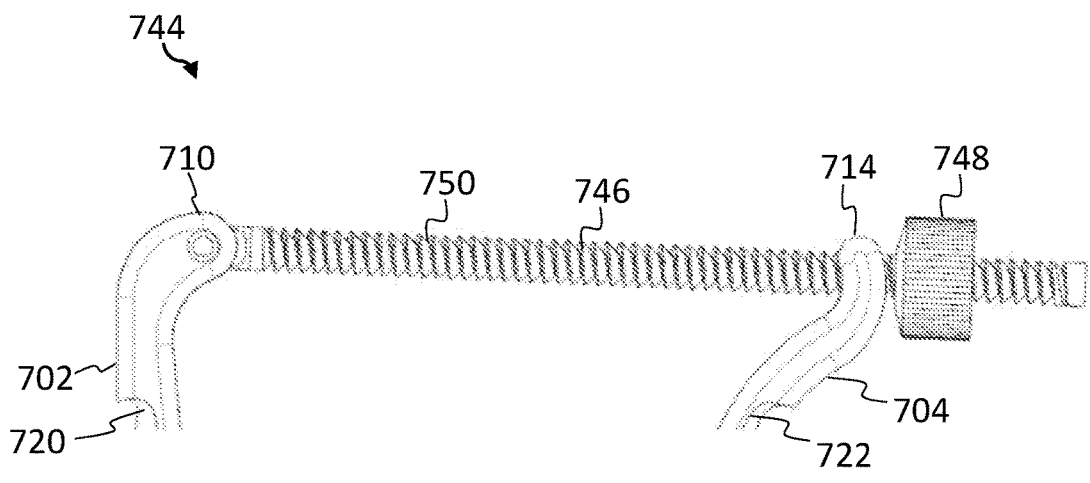
FIGS. 31A-31C show alternative locking members including a buttress thread with thumbwheel, ratchet arm, and buttress thread with a pivoting locking assembly, respectively.
Figure 32A:
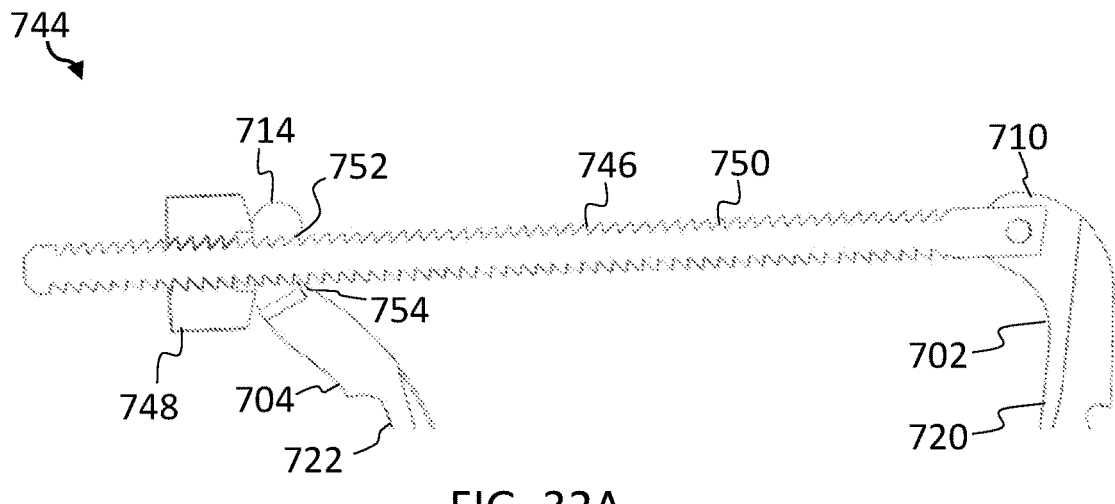
FIGS. 32A-32C show cross sectional views of the alternative locking members shown in FIGS. 31A-31C.

As best seen in FIGS. 31A and 32A, the locking member 744 may include a threaded shaft 746 and thumbwheel 748. The threaded shaft 746 may include a buttress thread 750 with an asymmetric sawtooth profile. A first end of shaft 746 may be coupled to one of the arms 702, 704, for example, via a pivot pin and the free end of the shaft 746 may be positionable through a slot or opening 752 in the body of the other arm 702, 704. The buttress thread 750 may engage with a projection or step 754 within opening 752 in the proximal end 714 of arm 704. The thumbwheel 748 may have outer ridges, knurls, or textured surface graspable by the user or an instrument and an internally threaded through hole. The thumbwheel 748 is positionable on the threaded shaft 746 on the outside of arm 704. As the thumbwheel 748 is rotated, the thumbwheel 748 advances forward, pushing against the outside of arm 704 and closer toward arm 702. The position of thumbwheel 748 along the shaft 746 prevents movement of handle 722 away from handle 720, thereby locking the distal positions of screw engaging projection 716 and hook 718, respectively. The buttress thread 746 with thumbwheel 748 allows the user to squeeze the two handles 720, 722, while the force can be held between the step 754 on the handle 722 and the buttress thread 746. Additionally, the user may use the thumbwheel 748 to provide for finer advancements or overcome large forces. The thumbwheel 748 may also be used in the opposite direction if the amount of translation exceeds their intentions or if there is an intention to go to the starting position of the instrument.

Figure 31B:
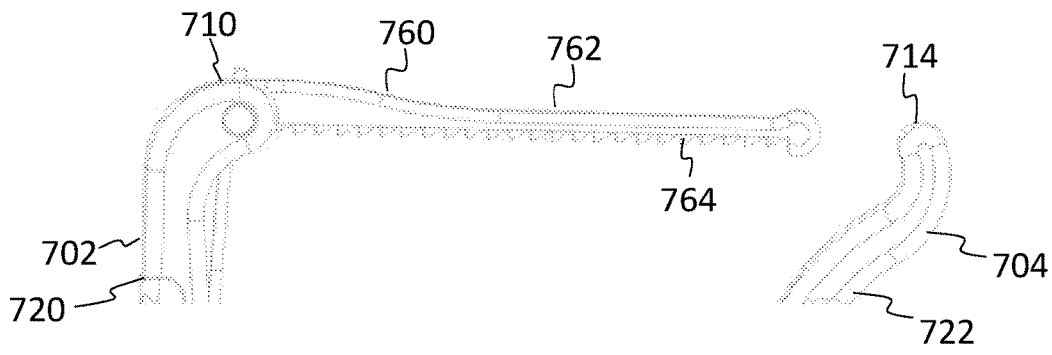
Figure 32B:
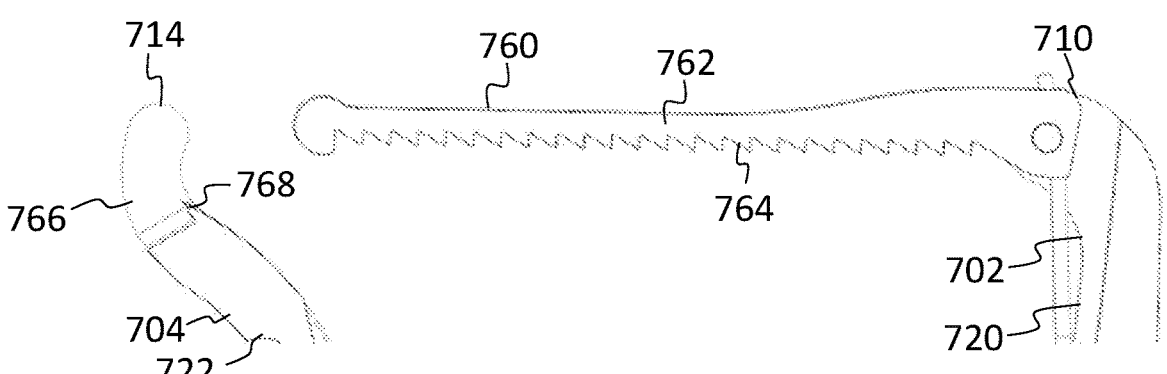

As best seen in FIGS. 31B and 32B, the locking member 744 may include a ratchet 760 having a ratchet arm 762 with ratchet teeth 764 engageable by a pawl 768 on the proximal end 714 of the hook arm 704. The ratchet arm 762 may include a linear rack or rail with a plurality teeth 764 defined along the interior of the ratchet 760. The teeth 764 may include one-way sloped asymmetric teeth that restrict linear motion to one direction. A first end of the ratchet 760 may be coupled to one of the arms 702, 704, for example, via a pivot pin and the opposite end of the ratchet 760 may be positionable through a slot or opening 766 in the body of the other arm 702, 704. As the ratchet 760 moves through the slot 766, the pawl 768 engages the teeth 764 on ratchet arm 762 to incrementally maintain the position of the arms 702, 704 with respect to one another. The ratchet 760 allows the user to provide quick motion, while allowing the advancement to be held in place due to the pawl 768 in handle 722 and angle of the mating ratchet 760. The ratchet arm 762 may also be quickly lifted and released, if desired.

Figure 31C:
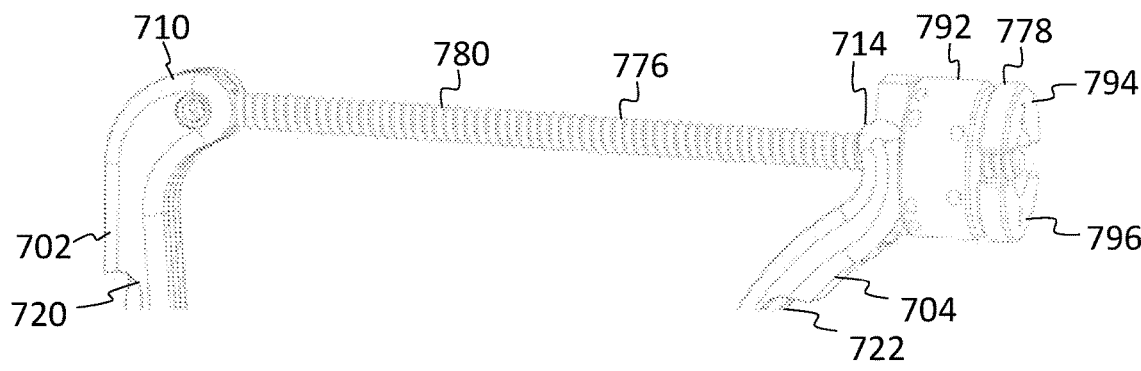
Figure 32C:
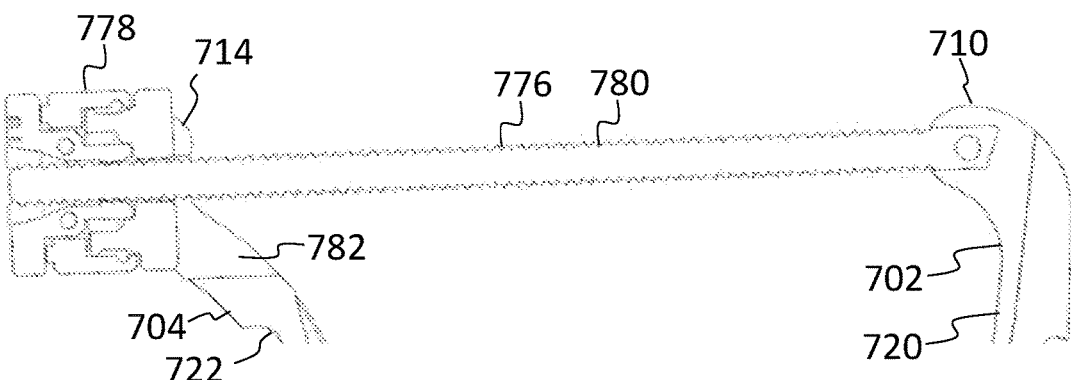

As best seen in FIGS. 31C and 32C, the locking member 744 may include a threaded shaft 776 and a pivoting locking assembly 778. The threaded shaft 776 may include a buttress thread 780 with an asymmetric sawtooth profile. A first end of shaft 776 may be coupled to one of the arms 702, 704, for example, via a pivot pin and the free end of the shaft 776 may be positionable through the pivoting locking assembly 778, which is coupled to the other arm 702, 704. The position of pivoting locking assembly 778 along threaded shaft 776 prevents movement of handle 722 away from handle 720, thereby locking the distal positions of screw engaging projection 716 and hook 718, respectively. The buttress thread 780 with pivoting locking assembly 778 offers the user the speed of a ratchet when the user squeezes the two handles 720, 722 together, while also offering the advantage of a thread to advance the instrument 700 continuously rather than increment by increment.

Figure 33:
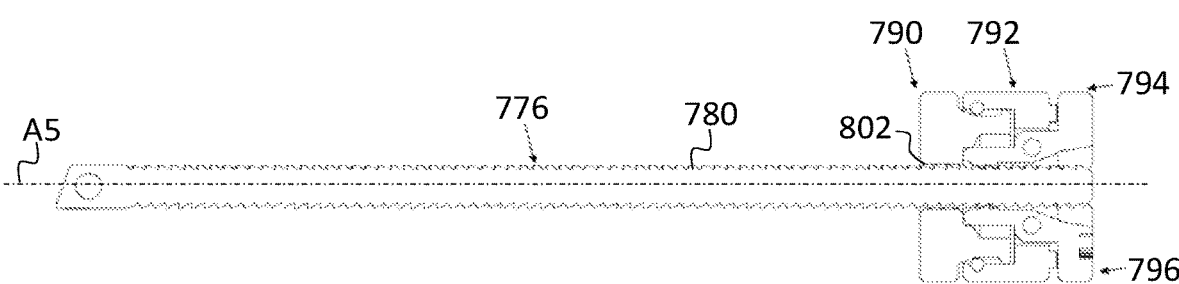
FIG. 33 shows a cross section of the buttress thread with pivoting locking assembly according to one embodiment.

FIGS. 33 and 34A-34C provide further details on the pivoting locking assembly 778. As shown in FIG. 33, the locking member 744 may include shaft 776 with buttress thread 780 positionable through the pivoting locking assembly 778, which are aligned along a central longitudinal axis A5. The pivoting locking assembly 778 may include a locking ring 790, a central ring 792, a first female thread piece 794, and a second female thread piece 796.

Figures 34A, 34B:
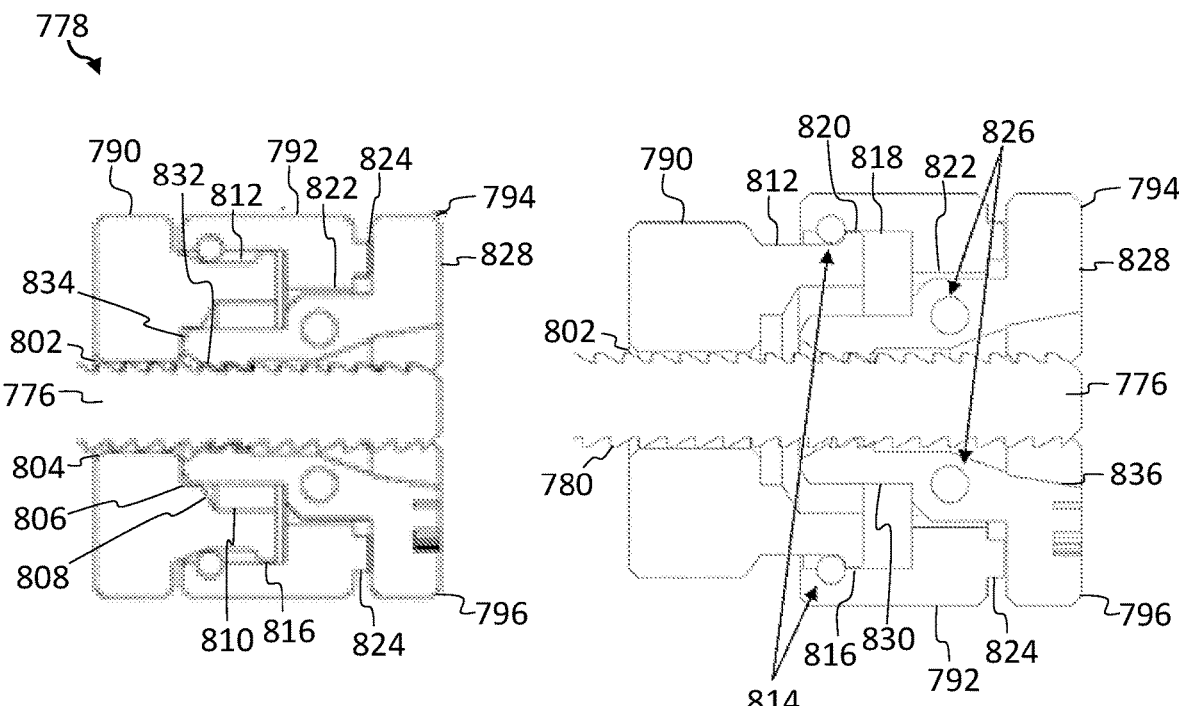
FIGS. 34A-34C show the cross section of the buttress thread with the pivoting locking assembly in a resting engaged position, a translated position, and a pivoted disengaged position, respectively.
Figure 34C:
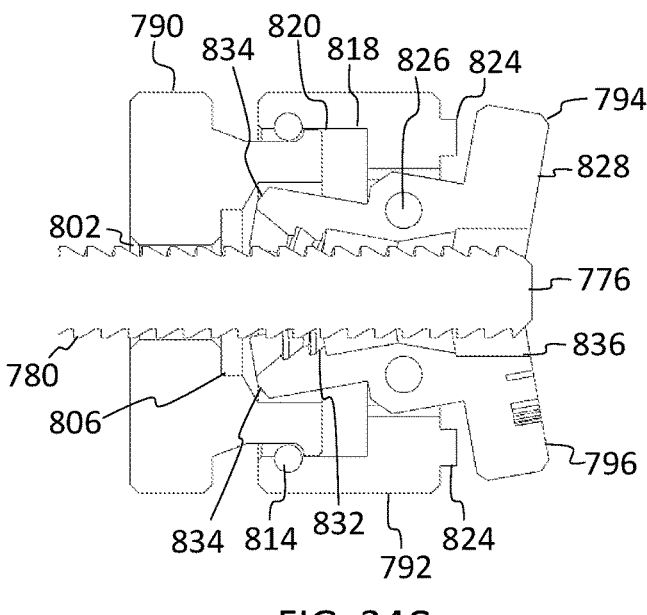

The locking ring 790 may include a cylindrical ring or band with an annular shape defining an opening or bore 802 therethrough. The ring 790 may have various cross-sectional profiles, including but not limited to circular, elliptical, square, or any other desired shape. The bore 802 has a central axis aligned with the central longitudinal axis A5. The bore 802 may include four areas: a reduced inner diameter section 804, stepped section 806, ramped edge 808, and enlarged inner diameter section 810. The reduced inner diameter section 804 may have a smooth inner surface sized and dimensioned to be slightly larger than the outer diameter of the shaft 776, thereby permitting free movement of the shaft 776 through the locking ring 790 in an unlocking position. The stepped section 806 has a diameter larger than the reduced diameter section 804 and is configured to receive the tips 834 of the female threads 794, 796 when in the engaged position (as shown in FIG. 34A). The ramped edge 808 is angled or sloped between the stepped section 806 and the enlarged diameter section 810. The enlarged inner diameter section 810 has the greatest diameter to permit pivoting of the female threads 794 into the disengaged position (as shown in FIG. 34C). The locking ring 790 may be retained to the central ring 792 with pins 814, allowing for translation of the central ring 792 and rotation of the central ring 792. The outer surface of the locking ring 790 may include a recess or groove 812 configured to receive connecting pins 814, which permit translation of the locking ring 790 relative to the central ring 792. The inner end of the locking ring 790 may terminate with radial projection 816, which fits inside central ring 792.

The locking ring 790 may be connected to the handle 722, for example, with a pin that allows for the central axis of the locking ring 790 to always be coincident to the central axis of the buttress thread 780. It will be appreciated that the locking ring 790 may be secured to handle 722 with any suitable mechanism. One or more springs may be attached to the handle 722 to provide a resting position of the handles 720, 722 as far apart as possible, and for the locking ring 790 to overlap the central ring 792 as much as possible. For example, a pair of leaf springs (not shown) may be located on an inner side of each handle 720, 722 to maintain the handles 720, 722 spaced apart and the distal ends 708, 712 in the closed position.

The central ring 792 may include a cylindrical ring or band with an annular shape defining an opening or bore 818 therethrough. The central ring 792 may have any suitable cross-sectional profile configured to engage with locking ring 790. The bore 818 has a central axis aligned with the central longitudinal axis A5. The bore 818 may include an enlarged inner diameter section 820 configured to receive the locking ring 790 and an inner reduced diameter section 822 configured to receive the female threads 794, 796. The base of central ring 792 includes projecting shoulders 824 configured to contact the female threads 794, 796 in the engaged position (shown in FIG. 34A).

The two female thread pieces 794, 796 may be retained to the central ring 792 with pivot pins 826, allowing for only pivoting about the pivot pins 826. The female threads 794, 796 may each include a pivoting body coupled to the central ring 792 via pivot pins 826. The pivoting body may have an L-shaped body including an outer base 828 and an inwardly projecting arm 830. The female threads 794, 796 are separated apart from one another to permit shaft 776 therethrough. An inner surface of each arm 830 defines teeth 832 configured to engage with the corresponding buttress thread 780 on shaft 776. The teeth 832 may be asymmetrical and sloped, such that when engaged with buttress thread 780, the teeth 832 limit movement to translation in a forward motion and prevent any backward translation. The tips 834 of each arm 830 are receivable in the stepped inner diameter area 806 of locking ring 790 when in the engaged position (shown in FIG. 34A). The tips 834 may be angled to interface with ramped portion 808 in locking ring 790. The ramped edge 808 in the locking ring 790 and angled tips 834 of female threads 794, 796 may help to prevent the female threads 794, 796 from getting stuck in the larger inner diameter 810 of the locking ring 790 when going from the disengaged position to the resting position within the smallest inner diameter 804 of the locking ring 790. On the opposite ends, the inner surfaces of each female thread 794, 796 may define sloped or slanted inner surfaces 836, which widen within base 828. The widened area may be configured to accept the female threads 794, 796 as the teeth 832 pivot out of engagement with buttress thread 780 (shown in FIG. 34C).

FIGS. 34A-34C show the cross section of the buttress thread 780 with the pivoting locking assembly 778 in a resting engaged position, a translated position, and a pivoted disengaged position, respectively. As shown in FIG. 34A, when the instrument 700 is in the resting engaged position, the locking ring 790 and central ring 792 are overlapping, causing the female thread pieces 794, 796 to sit in the smaller inner diameter 806 of the locking ring 790. This, along with an optional spring positioned between the central ring 792 and two female threads 794, 796, keeps the female threads 794, 796 engaged with the male threads 780, which prevents pivoting about the pivot pins 826 of the two female threads 794, 796. In this resting position, the two female threads 794, 796 are always engaged with the buttress thread 780.

As shown in FIG. 34B, when the two handles 720, 722 are squeezed together, a space is created between the locking ring 790 and central ring 792. The locking ring 790 translates outward and away from the central ring 792. The tips 834 of female threads 794, 796 withdraw from the reduced inner diameter 806 and enter the enlarged inner diameter 810 of the locking ring 790. The locking ring 790 translates outward until the radial projection 816 of the locking ring 790 contacts the locking ring connecting pin 814. When the locking ring 790 contacts the locking ring connecting pin 814, this allows the female threaded pieces 794, 796 to sit in the bigger inner diameter 820 of the locking ring 790, which permits pivoting of the two female threads 794, 796 about the female thread connecting pins 826.

As shown in FIG. 34C, further squeezing the handles 720, 722 together allows the female threads 794, 796 to disengage from the male buttress threads 780 and act as a ratcheting mechanism where the female threads 794, 796 may use the angle of the buttress thread 780 to act as a ramp to translate along the length of the shaft 776 of buttress thread 780. The profile of the buttress thread 780 limits the ratchet to only translation in a forward motion, as it prevents any backward translation. The shoulders 824 on the central ring 792 limit the inward pivot about the female thread connection pins 826 when the handles 720, 722 are being squeezed.

When the handles 720, 722 are released, the assembly may include a spring force to cause the two female threaded pieces 794, 796 to bias back into the engaged position when the assembly is at rest. The ramped edge 808 in the locking ring 790 and female threaded pieces 794, 796 may help to prevent the female threads 794, 796 from remaining in the larger inner diameter 810 of the locking ring 790 when going from the disengaged position to the engaged resting position within the smallest inner diameter 806 of the locking ring 790. The ramp 808 may allow for a smooth insertion of the female threaded pieces 794, 796 into the smallest inner diameter 806 of the locking ring 790.

Figure 35:
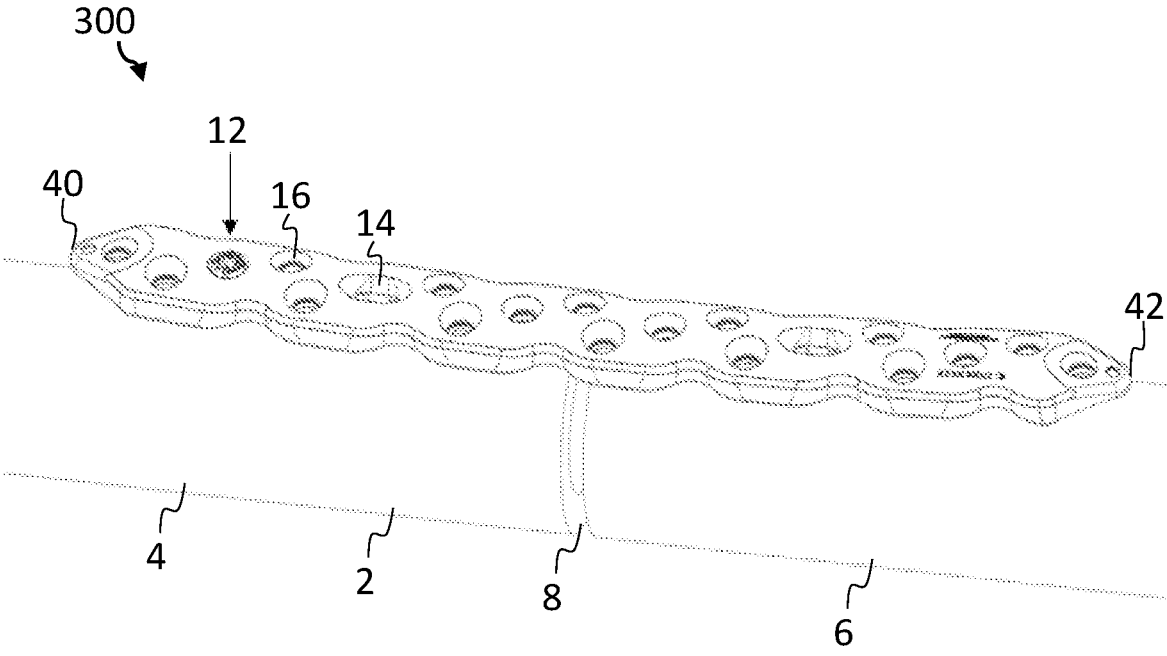
FIG. 35 shows a screw inserted into one end of the plate in a method for providing compression to a fracture according to one embodiment.

Turning now to FIGS. 35-44, methods for compressing and/or distracting a fracture through a plate 300 are shown. In one embodiment, steps for compressing bone fragment 6 to reduce the fracture 8 are shown in FIGS. 35-40. As shown in FIG. 35, compression of fracture 8 may be achieved by first fixing the plate 300 in place on one end of the fracture 8 using a screw 12 through a screw hole 16. The bone plate 300 may be positioned against the bone fragments 4, 6 and across the fracture 8. The bone plate 300 may be secured to the first bone fragment 4, for example, using a polyaxial locking screw 12 through any suitable polyaxial hole 16 configured to enter bone fragment 4. Although a broad straight plate 300 is exemplified in this embodiment, it will be appreciated that any suitable plate may be selected.

Figure 36:
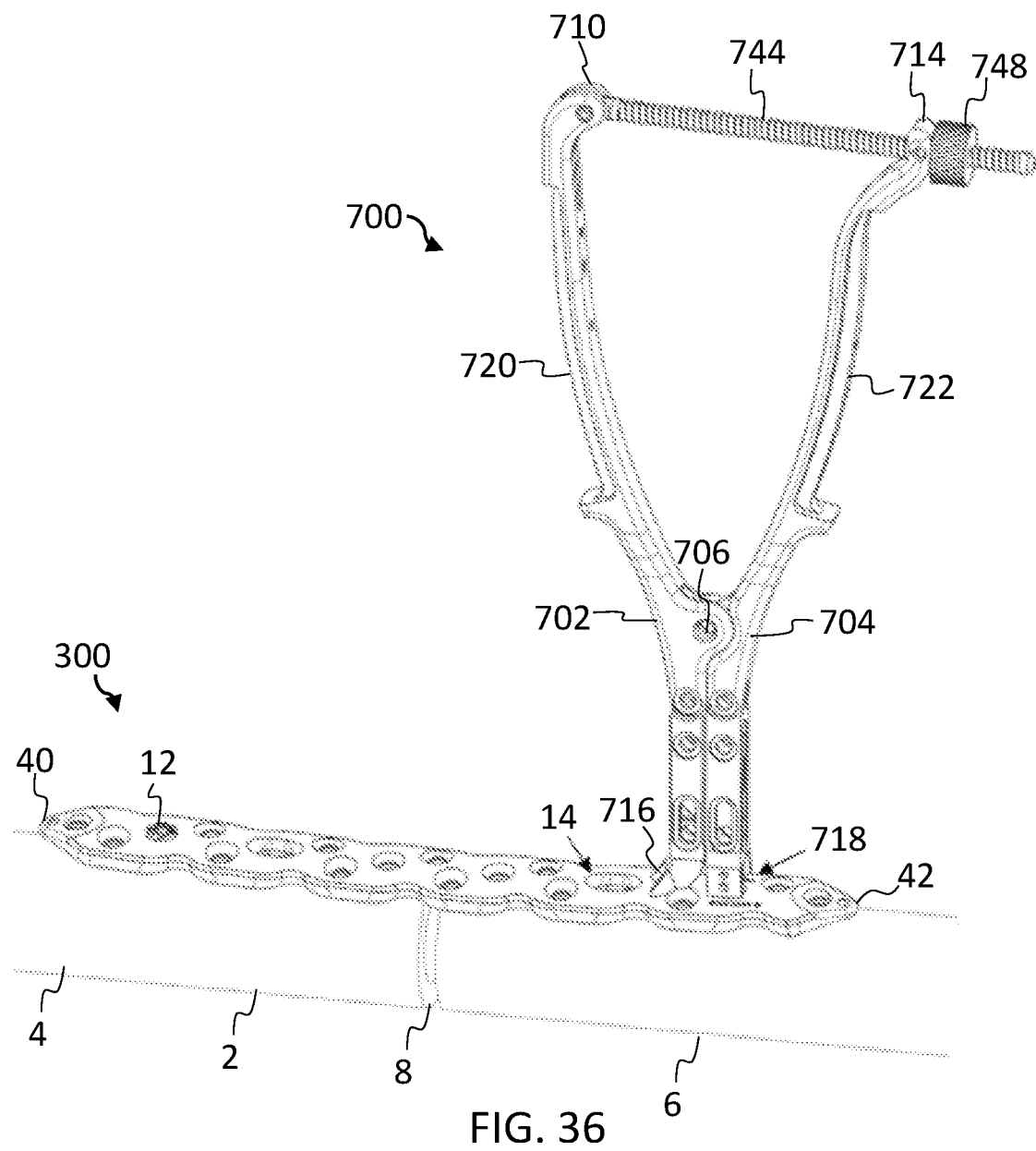
FIG. 36 shows the compression/distraction instrument hooked into the plate for providing compression to the fracture.
Figure 37:
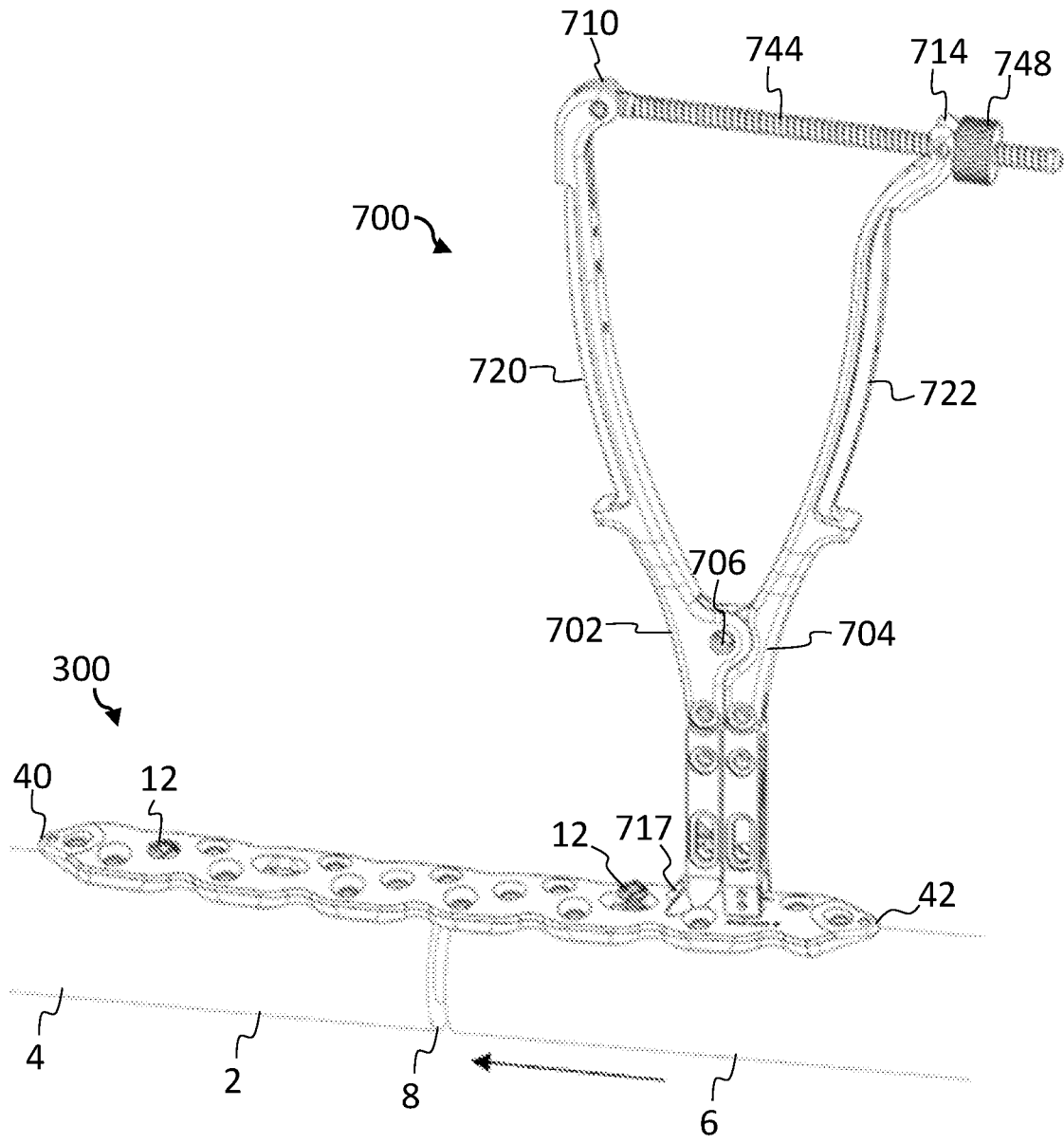
FIG. 37 shows a screw inserted into a compression slot nearest to the compression/distraction instrument for providing compression to the fracture.

As shown in FIG. 36, the user may then hook the compression/distraction instrument 700 under any screw hole 16 on the opposite side of the fracture 8. The translation arm 702 may be facing toward the fracture 8 positioned behind a compression slot 14 and the hook arm 704 may be facing away from the fracture 8. The hook 718 of instrument 700 may enter hole 16 and hook under the plate 300, thereby temporarily securing instrument 700 to plate 300. As shown in FIG. 37, the user may then insert another screw 12 into the compression slot 14 nearest to the opening 717 in the screw engaging projection 716 of the translation arm 702. The screw 12 may be secured to the second bone fragment 6 on the opposite side of fracture 8. The screw 12 may sit proud of the compression slot 14 such that the screw engaging projection 716 of instrument 700 may easily engage the head and/or shaft of the screw 12, thereby providing a temporary attachment to screw 12.

Figure 38:
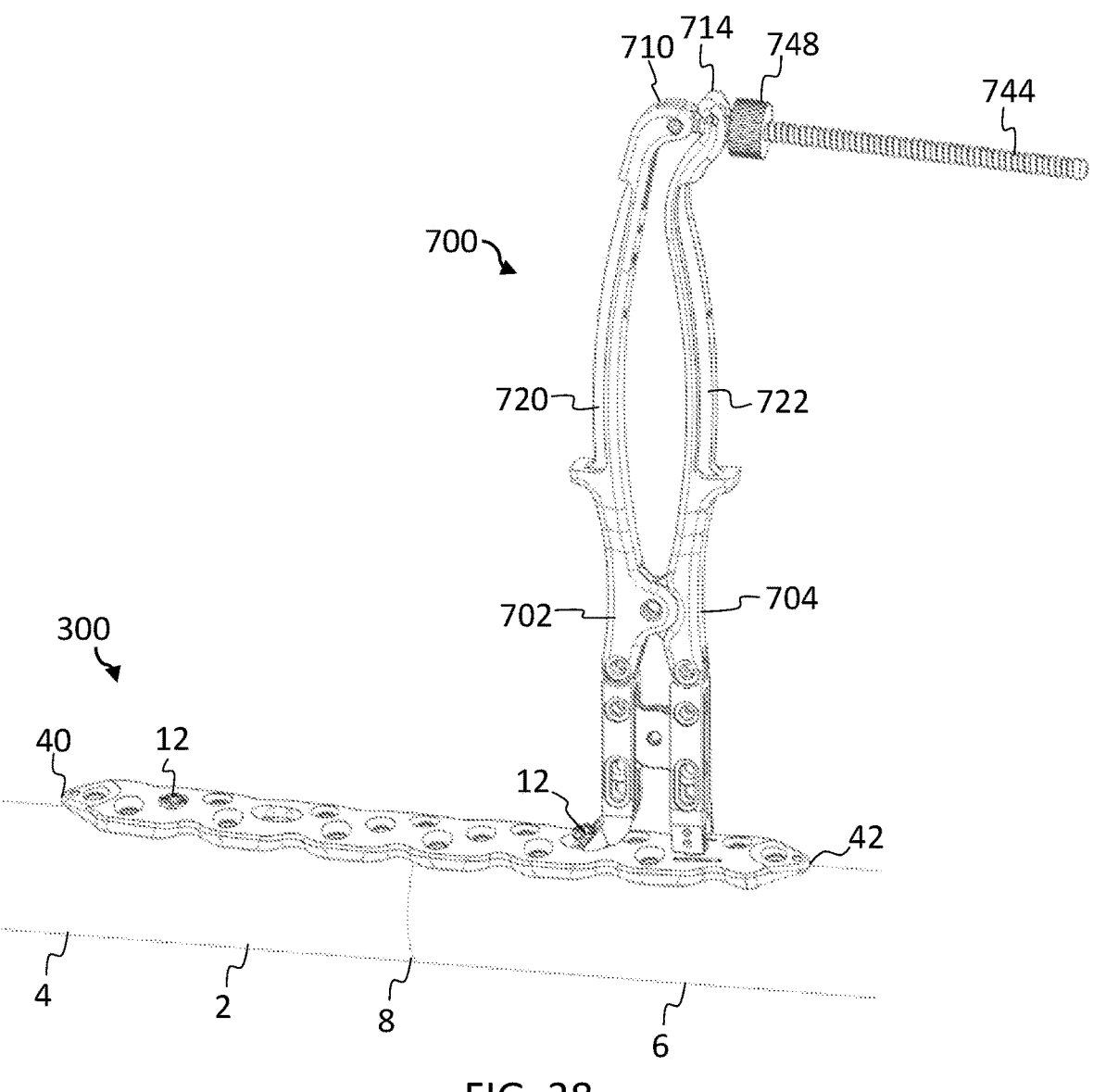
FIG. 38 shows a final position of the compression/distraction instrument for fracture compression.

As shown in FIG. 38, the user then compresses the handles 720, 722 of the compression/distraction instrument 700 to push on the screw 12 in the compression slot 14, resulting in a translation of the un-fixed side of the plate 300. When the handles 720, 722 of instrument 700 are squeezed together, the screw engaging projection 716 of arm 702 pushes against screw 12 and bone fragment 6 translates toward bone fragment 4, thereby reducing fracture 8. The translation may occur until one of the following conditions is met: (a) the desired amount of compression of the fracture 8 is achieved; (b) the large fragment screw 12 no longer has room to translate within the compression slot 14; or (c) the compression/distraction instrument 700 reaches its ending position as shown in FIG. 38.

Figure 39:
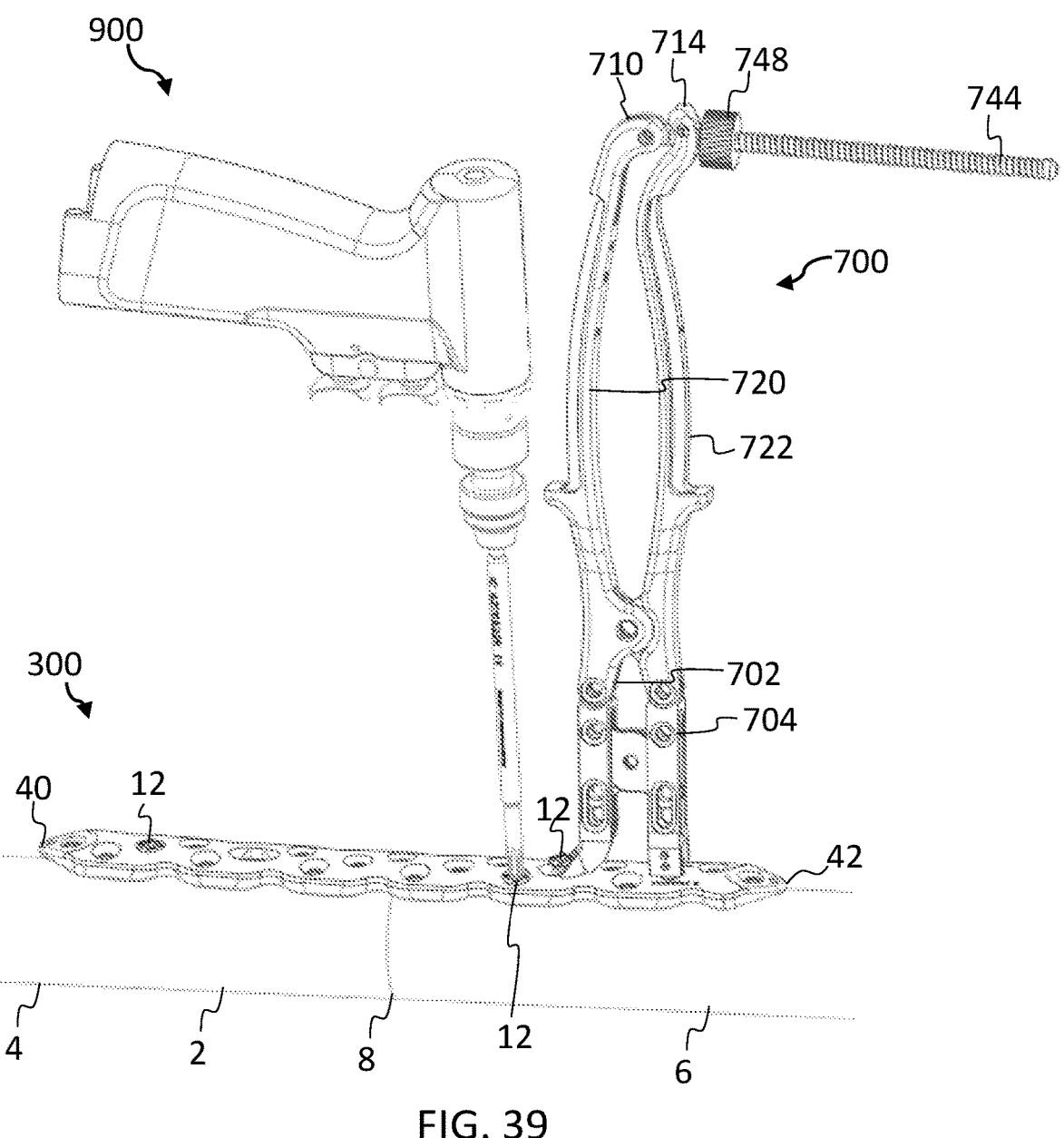
FIG. 39 shows a screw driver inserting a screw to maintain the compression to the fracture.
Figure 40:
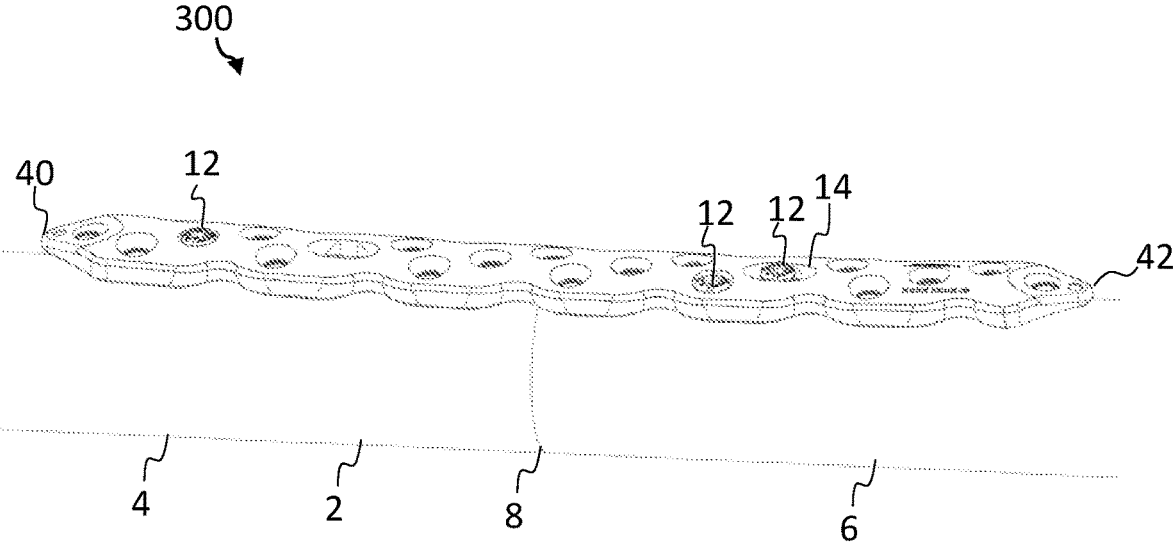
FIG. 40 shows the final bone reduction and implant placement compressing the fracture through the plate.

As shown in FIG. 39, the user may then fix the compression generated through the compression/distraction instrument 700 and plate 300 by inserting screw 12 into any of the holes 16 on the same side of the fracture 8 as the instrument 700. For example, an instrument 900, such as a screw driver, may be used to install third screw 12 into polyaxial hole 16 and into the second bone fragment 6. In this manner, the bone fragment 6 is secured relative to first bone fragment 4, thereby maintaining the reduction of fracture 8. When the plate 300 is fixed in place, the instrument 700 may be removed from plate 300, and the screw 12 in the compression slot 14 may be removed or fully seated as shown in FIG. 40. The surgeon may add additional screws 12 to plate 300 to further secure the fracture 8 and finish installing the plate 300.

Figure 41:
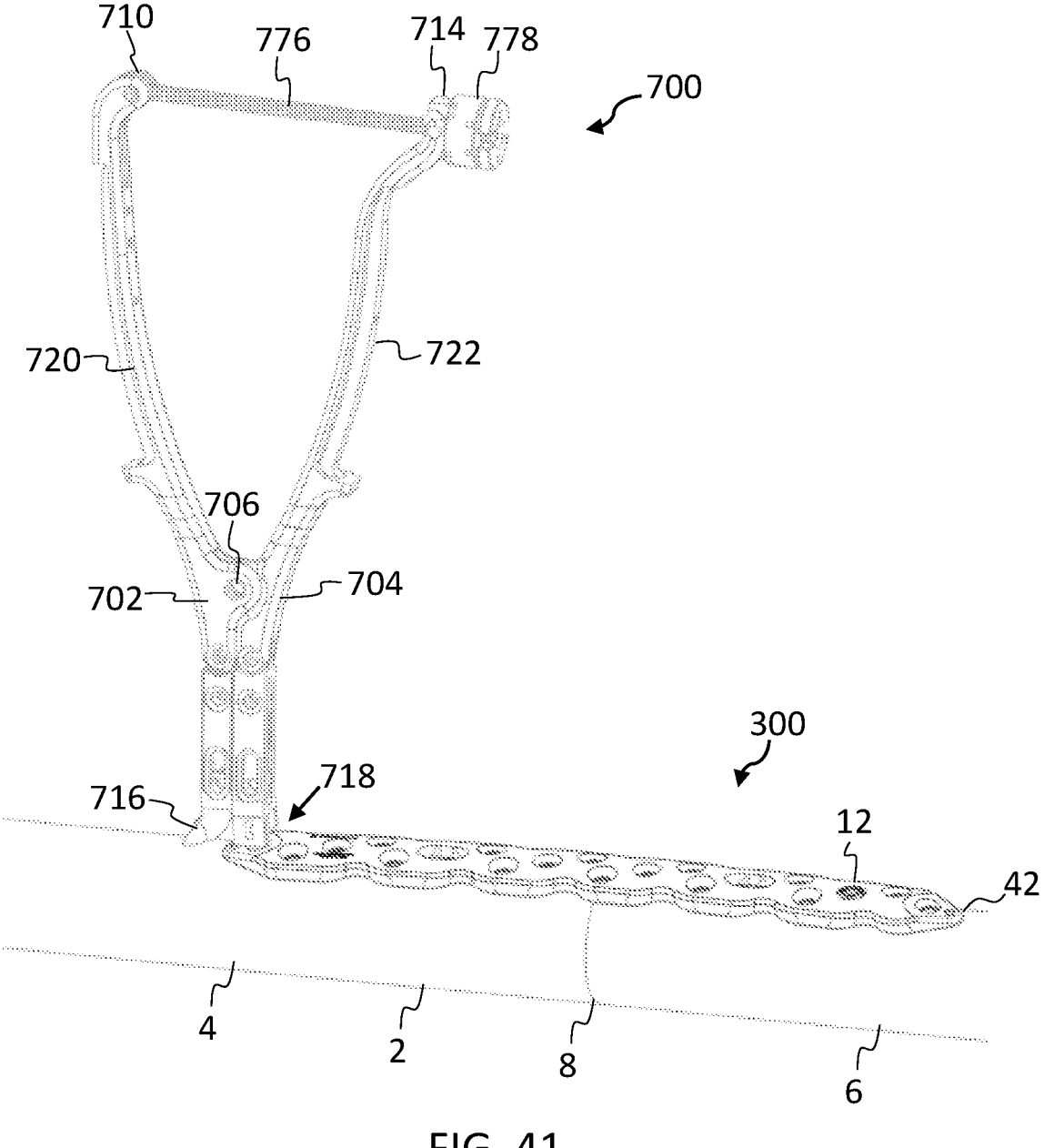
FIG. 41 shows the compression/distraction instrument hooked into the plate in a method for providing distraction to the fracture according to one embodiment.

In an alternative embodiment, the bone fragment 4 may be distracted to reduce the fracture 8. Steps for distracting bone fragment 4 to reduce the fracture 8 are shown in FIGS. 41-44. Distraction of the fracture 8 may be achieved by first fixing the plate 300 in place on one end of the fracture 8. For example, the bone plate 300 may be positioned against the bone fragments 4, 6 and across the fracture 8. The bone plate 300 may be secured to the second bone fragment 6, for example, using a polyaxial locking screw 12 through any suitable polyaxial hole 16 configured to enter bone fragment 6. As shown in FIG. 41, the user may then hook the compression/distraction instrument 700 under the hole 16 on the far end 40 of the plate 300 on the opposite side of the fracture 8. The translation arm 702 may be facing away from the fracture 8 and the hook arm 704 may be facing toward the fracture 8. The hook 718 of instrument 700 may enter hole 16 and hook under the plate 300, thereby temporarily securing instrument 700 to plate 300.

Figure 42:
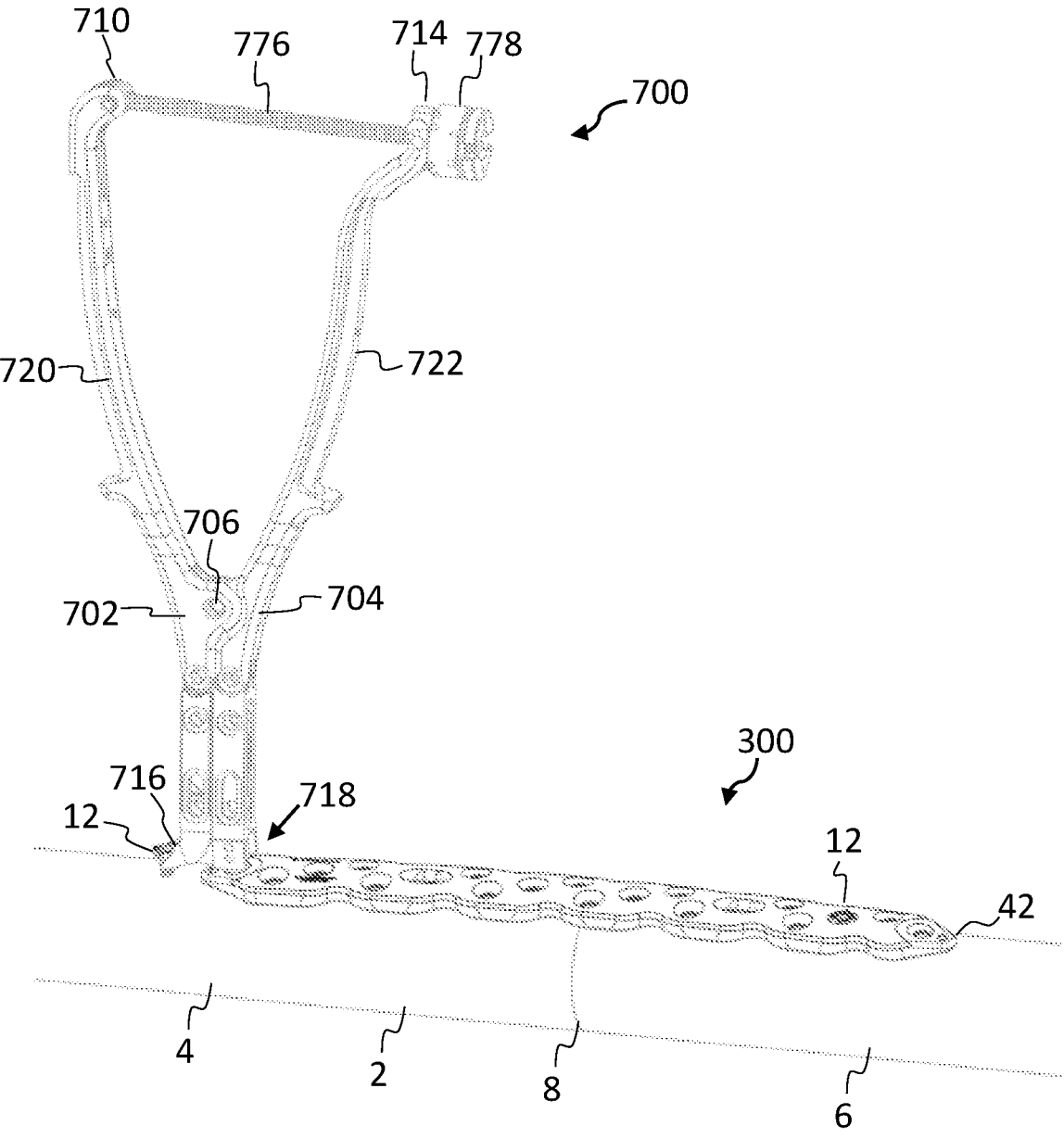
FIG. 42 shows a large fragment screw inserted into the bone, outside the plate, and close to the compression/distraction instrument for fraction distraction.
Figure 43:
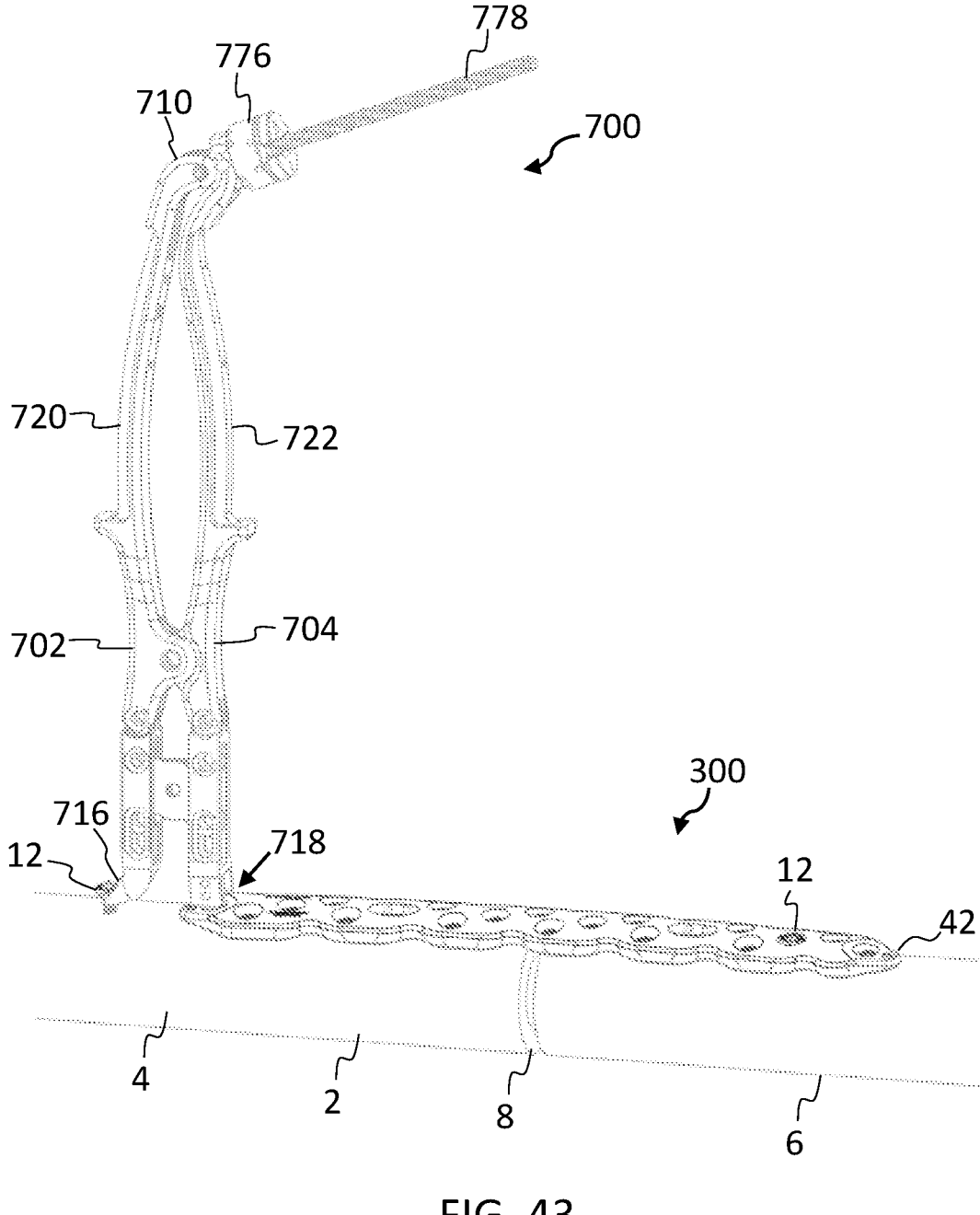
FIG. 43 shows the compression/distraction instrument in a final distraction position.

As shown in FIG. 42, the user may then insert a large fragment screw 12 into the bone 4 outside of the plate 300, close to the opening 717 in the screw engaging projection 716 of the translation arm 702. The second screw 12 may be secured to the bone fragment 4 on the opposite side of fracture 8. The screw 12 may sit proud of the bone 4 such that the screw engaging projection 716 of instrument 700 may easily engage the head or shaft of the screw 12, thereby providing a temporary attachment to screw 12. The user may then compress the handles 720, 722 of the instrument 700 to push on the screw 12, resulting in translation of the un-fixed side of the bone 4. When the handles 720, 722 of instrument 700 are squeezed together, the screw engaging projection 716 of arm 702 pushes against screw 12 and bone fragment 4 translates toward bone fragment 6, thereby reducing fracture 8. The translation may occur until one of the following conditions is met: (a) the desired amount of distraction of the fracture 8 is achieved; or (b) the compression/distraction instrument 700 reaches its ending position as shown in FIG. 43.

Figure 44:
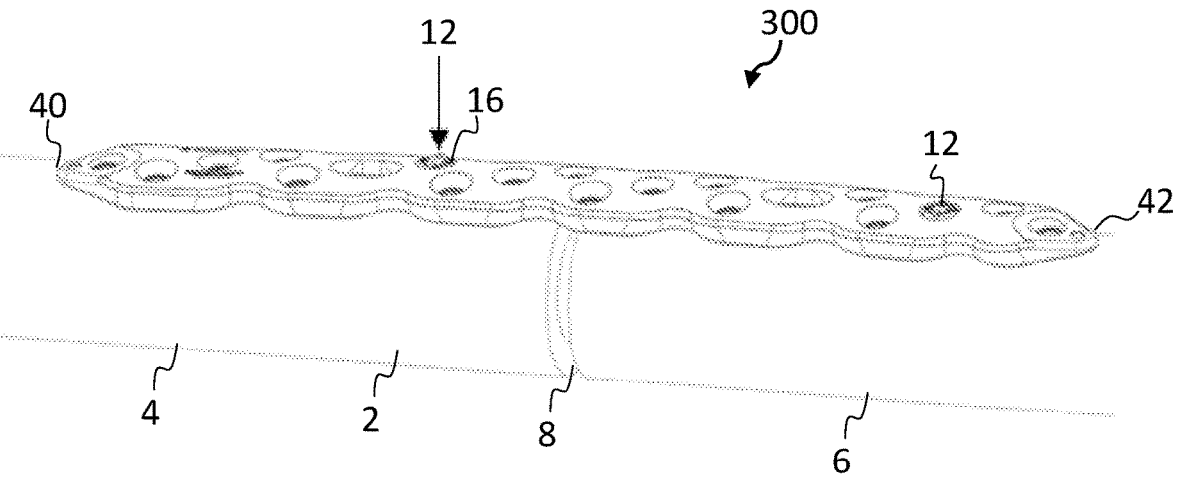
FIG. 44 shows the final bone reduction and implant placement by distracting outside of the plate.

As shown in FIG. 44, the user may then fix the distraction generated through the instrument 700 by inserting screw 12 into any of the holes 16 on the same side 4 of the fracture 8 as the compression/distraction instrument 700. For example, a screw driver 900 may be used to install locking screw 12 into polyaxial hole 16 and into the first bone fragment 4. In this manner, bone fragment 4 is secured relative to second bone fragment 6, thereby maintaining the reduction of fracture 8. When the plate 300 is fixed in place, the instrument 700 may be removed, and the screw 12 outside of the plate 300 may be fully seated, replaced with a shorter screw, or removed. The surgeon may add additional screws 12 to plate 300 to further secure the fracture 8 and finish installing the plate 300.

Figure 45:
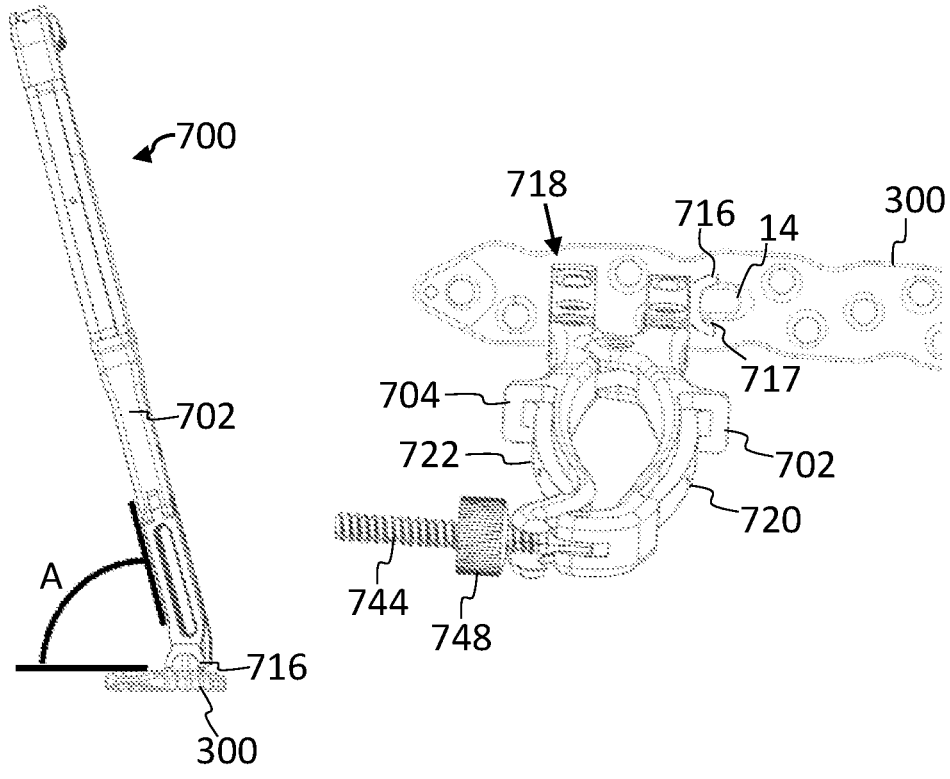
FIGS. 45A-45B show an instrument offset to provide increased implant visibility according to one embodiment.
Figure 46:
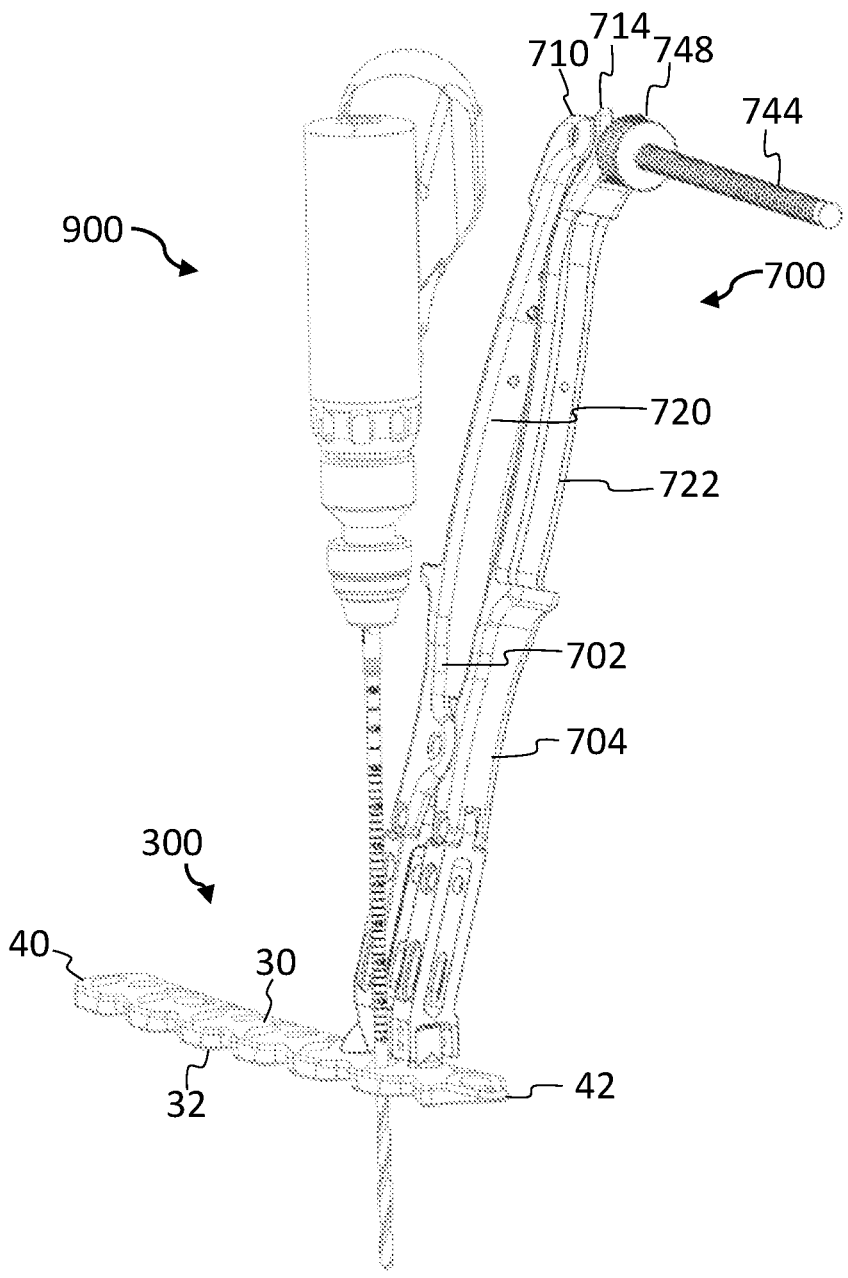
FIG. 46 shows increased space for instrumentation needed to fix compression or distraction generated by the compression/distraction instrument.

Turning now to FIGS. 45A-45B and 46, the compression/distraction instrument 700 may allow for increased visibility of the incision site and implant 300 by including an offset angle A between arms 702, 704 and plate 300. For example, the handles 720, 722 and arms 702, 704 of instrument 700, or a portion thereof, may lie in the same plane while the screw engaging projection 716 and hook 718 are angled. In this manner, offset angle A may help to facilitate visualization of the treatment site during distraction and compression. As shown in FIG. 46, this offset may also allow for increased space for instruments 900, such as drills, drill guides, drivers, and other instrumentation needed to fix the plate 300 in place after the compression/distraction instrument 700 is used.

The fracture reduction instrument allows for quick compression or distraction of the fracture, while maintaining a clear view of the incision and implant. In addition, the compression/distraction instrument allows for ample space to insert additional screws when the instrument is in place to fix the compression or distraction achieved. The instrument handles and locking member, including the buttress thread or ratchet assembly, are sufficiently out of the way from any soft tissue, allowing the user to have full functionality in operating the instrument.

It will be further understood that various changes in the details, materials, and arrangements of the parts which have been described and illustrated in order to explain the nature of this invention may be made by those skilled in the art without departing from the scope of the invention as expressed in the claims. One skilled in the art will appreciate that the embodiments discussed above are non-limiting. It will also be appreciated that one or more features of one embodiment may be partially or fully incorporated into one or more other embodiments described herein.

What is claimed is:

1. A bone stabilization system for reducing a fracture between two bone fragments, the system comprising:
    a bone plate having an elongate body extending between two ends, the bone plate having a shaft portion and a tapered region decreasing in thickness from the shaft to one end, a plurality of fastener openings defined therethrough including one polyaxial opening extending through the tapered region, and polyaxial openings and compression slots extending through the shaft portion; and
    a fracture reduction instrument having a translation arm and a hook arm pivotably coupled together, the translation arm has a screw engaging projection configured to engage a bone screw and the hook arm has a hook configured to engage the bone plate, wherein the fracture reduction instrument is configured to apply compression or distraction to the bone plate to reduce the fracture,
    wherein a guide wire hole is defined through the tapered region, and a swept cut connects the polyaxial opening to the guide wire hole on an underside of the bone plate.

2. The system of claim 1, wherein when the bone screw is positioned through the compression slot and the screw engaging projection of the instrument applies a force to the bone screw towards the fracture, compression is applied to the fracture, and when the bone screw is positioned outside of the bone plate and the screw engaging projection of the instrument applies a force to the bone screw, distraction is applied to the fracture.

3. The system of claim 1, wherein the fastener openings defined through the shaft portion form a mirrored repeating pattern about a central transverse plane of the bone plate.

4. The system of claim 1, wherein the fastener openings defined through the shaft portion form a repeating three-hole pattern arranged on a slope.

5. The system of claim 1, wherein the compression slots are aligned along a central longitudinal axis, and the polyaxial openings are aligned along first and second offset axes located above and below the central longitudinal axis, respectively.

6. The system of claim 1, wherein the bone plate includes a metaphyseal portion having a thin plate thickness, a diaphyseal portion having a thick plate thickness, and a transition region between the metaphyseal portion and the diaphyseal portion, wherein the metaphyseal portion and the transition region have polyaxial openings with a diameter smaller than the polyaxial openings in the diaphyseal portion.

\* \* \* \* \*